United States Patent
Thatcher et al.

(10) Patent No.: US 6,310,052 B1
(45) Date of Patent: *Oct. 30, 2001

(54) NITRATE ESTERS AND THEIR USE FOR NEUROLOGICAL CONDITIONS

(75) Inventors: Gregory R. J. Thatcher; Brian M. Bennett; James N. Reynolds; Roland J. Boegman; Khem Jhamandas, all of Kingston (CA)

(73) Assignee: Queen's University at Kingston, Kingston (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 66 days.

(21) Appl. No.: 09/267,379

(22) Filed: Mar. 15, 1999

Related U.S. Application Data

(63) Continuation-in-part of application No. 08/867,856, filed on Jun. 3, 1997, now Pat. No. 5,883,122, which is a continuation-in-part of application No. 08/658,145, filed on Jun. 4, 1996, now Pat. No. 5,807,847.

(51) Int. Cl.$^7$ .................. A61K 31/255; A61K 31/66; A61K 31/39; A61K 31/21
(52) U.S. Cl. ................. 514/129; 23/24; 23/439; 23/509; 23/517
(58) Field of Search ................ 514/129, 23, 24, 514/439, 517, 509

(56) References Cited

U.S. PATENT DOCUMENTS

| | | |
|---|---|---|
| 4,780,560 | 10/1988 | Kumonaka et al. . |
| 4,801,596 | 1/1989 | Simon et al. . |
| 4,863,949 | 9/1989 | Simon et al. . |
| 5,049,694 | 9/1991 | Bron et al. . |
| 5,234,956 | 8/1993 | Lipton . |
| 5,284,872 | 2/1994 | Sandrock et al. . |
| 5,428,061 | 6/1995 | Sandrock et al. . |
| 5,455,279 | 10/1995 | Lipton . |
| 5,621,000 | 4/1997 | Arena et al. . |
| 5,700,947 | 12/1997 | Soldato . |
| 5,780,495 | 7/1998 | Del Soldato . |
| 5,861,426 | 1/1999 | Del Soldato et al. . |

FOREIGN PATENT DOCUMENTS

| | | |
|---|---|---|
| 764461 | 8/1967 | (CA) . |
| 792246 | 8/1968 | (CA) . |
| 2158368 | 9/1994 | (CA) . |
| 0882716 A | 12/1998 | (EP) . |
| 51-125750 | 11/1976 | (JP) . |
| 01-304353 | 12/1989 | (JP) . |
| 7-26949 | 3/1995 | (JP) . |
| PCT/EP91/00290 | 2/1991 | (WO) . |
| PCT/US93/09019 | 9/1993 | (WO) . |
| WO 95/00477 | 1/1995 | (WO) . |
| WO 98/43621 A | 10/1998 | (WO) . |

OTHER PUBLICATIONS

Bulsson A., et al., "Deleterious and protective modulatory role of nitric oxide during focal cerebral ischaemia." *Journal of Cerebral Blood Flow and Metabolism*, 13:S166 (1993).

Lipton, S.A., et al., "Nitric oxide in the central nervous system." *Progress in Brain Research*, 103:359–364 (1994).

Manchester, K.S., et al., "Chronic administration of nitroglycerin decreases cerebral infarct size." Abstract, *Neurology* 43:A365 (1993).

Lipton, et al., "NO–related species can protect from focal cerebral ischemia/reperfusion" *Pharmacol. Cereb. Ishemia*, 1996, 6$^{th}$ Int. Symp.; pp. 183–191.

Lipton et al., "S–nitrosylation of NMDA receptor and caspases affords neuroprotection from NMDA receptor–mediated insults" *Pharmacol. Cereb. Ishemia*, 1999, Int. 7$^{th}$ Symp.; pp. 217–226.

Uchiyama–Tsuyuka, et al., "VA–045, a novel apovincaminic acid derivative attenuates neuronal injury induced by hypoxia or by excitatory amino acids in cultures of rat cortices" *Life Sci.*, 1996, 59(18):1571–1578.

Ramos–Zuniga, et al., "Neuroprotection in selective focal ischemia in rats by nitrates, an alternative redox manipulation on nitric oxide: Experimental Model" *Minim. Invas. Neurosurg.*, 1998, 41(3):152–160.

Abe, K., C. Takeyama, K. Yoshimura, "Effects of S–8510, a novel benzodiazepine receptor partial inverse agonist, on basal forebrain lesioning–induced dysfunction in rats." *Eur. J. Pharmacol.* 347 (1998) 145–152.

Arancio, O., E.R. Kandel, R.D. Hawkins, "Activity–dependent long–term enhancement of transmitter release by presynaptic 3',5'–cyclic GMP in cultured hippocampal neurons." *Nature* 376 (1995) 74–80.

Artz, J.D., K. Yang, J. Lock, C. Sanchez, B.M. Bennett, and G.R.J. Thatcher, "Reactivity of thionitrate esters: putative intermediates in nitrovasodilator activity." *Chem. Commun.* (1996) 927–928.

(List continued on next page.)

Primary Examiner—Raymond Henley, III
(74) Attorney, Agent, or Firm—Stephen J. Scribner; Carol Miernicki Steeg

(57) ABSTRACT

Compounds and methods for mitigating neurodegeneration, effecting neuroprotection and/or effecting cognition enhancement in a subject are described. Neurological or cognitive conditions are treated by administering to a subject an effective amount of a therapeutic compound comprising a nitrate ester, or a pharmaceutically acceptable salt or ester thereof.

44 Claims, 32 Drawing Sheets

OTHER PUBLICATIONS

Bak, A.W., W. McKnight, P. Li, P. Del Soldato, A. Calignano, G. Cirino, J.L. Wallace, "Cyclooxygenase–Independent Chemoprevention with an Aspirin Derivative in a Rat Model of Colonic Adenocarcinoma." Life Sci. 62 (1998) 367–373.

Barger, S.W., R.R. Fiscus, P. Ruth, F. Hofmann, M.P. Mattson, "Role of cyclic GMP in the regulation of neuronal calcium and survival by secreted forms of β–amyloid precursor protein." J. Neurochem. 64 (1995) 2087–2096.

Bennett, B.M., B.J. McDonald, R. Nigam, and W.C. Simon, "Biotransformation of organic nitrates and vascular smooth muscle cell function." Trends Pharmacol. Sci. 15 (1994) 245–249.

Bennett, B.M., B.J. McDonald, R. Nigam, P.G. Long, and W.C. Simon, "Inhibition of nitrovasodilator– and acetylcholine–induced relaxation and cyclic CMP accumulation by the cytochrome P–450 substrate, 7–ethoxyresorufin." Can. J. Physiol. Pharmacol. 70 (1992) 1297–1303.

Berge, S.M., L.D. Bighley, and D.C. Monkhouse, "Pharmaceutical Salts." J. Pharm. Sci. 66 (1977) 1–19.

Bernabeu, R., P. Schmitz, M.P. Faillace, I. Izquierdo, J.H. Medina, "Hippocampal cGMP and cAMP are differentially involved in memory processing in inhibitory avoidance learning." NeuroReport 7 (1996) 585–588.

Bernabeu, R., N. Schroder, J. Quevedo, M. Cammarota, I. Izquierdo, J.H. Medina, "Further evidence for the involvement of a hippocampal cGMP/cGMP–dependent protein kinase cascade in memory consolidation," NeuroReport 8 (1997) 2221–2224.

Bloeman, P.G.M., P.A.J. Henricks, L. van Bloois, M.C. van den Tweel, A.C. Bloem, F.P. Nijkamp, D.J.A. Crommelin, and G. Storm, "Adhesion molecules: a new target for immunoliposome–mediated drug delivery." FEBS Lett. 357 (1995) 140–144.

Briscoe, P., I. Caniggia, A. Graves, B. Benson, L. Huang, A.K. Tanswell, and B.A. Freeman, "Delivery of superoxide dismutase to pulmonary epithelium via pH–sensitive liposomes." Am. J. Physiol. (1995) 374–380.

Bullock, R., A. Zauner, J.J. Woodward, J. Myseros, S.C. Choi, J.D. Ward, A. Marmarou, H.F. Young, "Factors affecting excitatory amino acid release following severe human head injury." J. Neurosurg. 89 (1998) 507–518.

Cameron, D.R., A.M.P. Borrajo, B.M. Bennett, and G.R.J. Thatcher, "Organic nitrates, thionitrates, peroxynitrites, and nitric oxide: a molecular orbital study of $RXNO_2 \rightleftharpoons RXONO$ (X=O,S) rearrangement, a reaction of potential biological significance." Can. J. Chem. 73 (1995) 1627–1638.

Chan, P.H., M. Kawase, K. Murakami, S.F. Chen, Y. Li, B. Calagui, L. Reola, E. Carlson, and C.J. Epstein, "Overexpression of SOD1 in transgenic rats protects vulnerable neurons against ischemic damage after global cerebral ischemia and reperfusion." J. Neurosci. 18 (1998) 8292–8299.

Chen, J., T. Nagayama, K. Jin, R.A. Stetler, R.L. Zhu, S.H. Graham, and R.P. Simon. "Induction of caspase–3–like protease may mediate delayed neuronal death in the hippocampus after transient cerebral ischemia." J. Neurosci. 18 (1998) 4914–4928.

Chong, S., and H.–L. Fung, "Biochemical and pharmacological interactions between nitroglycerin and thiols. Effects of thiol structure on nitric oxide generation and tolerance reversal." Biochem. Pharm. 42 (1991) 1433–1439.

Cohen, G.M., "Caspases: the executioners of apoptosis." Biochem. J. 326 (1997) 1–16.

Du, Y., K.R. Bales, R.C. Dodel, E. Hamilton–Byrd, J.W. Horn, D.L. Czilli, L.K. Simmons, B. Ni, and S.M. Paul, "Activation of a caspase–3–related cysteine protease is required for glutamate–mediated apoptosis of cultured cerebellar granule neurons." Proc. Natl. Acad. Sci. 94 (1997) 11657–11662.

Endres, M., S. Namura, M. Shimizu–Sasamata, C. Waeber, L. Zhang, T. Gomez–Isla, B.T. Hyman, and M.A. Moskowitz, "Attenuation of delayed neuronal death after mild focal ischemia in mice by inhibition of the caspase family." J. Cereb. Blood Flow Metab. 18 (1998) 238–247.

Estevez, A.G., N. Spear, J.A. Thompson, T.L. Cornwell, R. Radi, L. Barbeito, and J.S. Beckman, "Nitric oxide–dependent production of cGMP supports the survival of rat embryonic motor neurons cultured with brain–derived neurotrophic factor." J. Neurosci. 18 (1998) 3708–3714.

Farinelli, S.E., D.S. Park, and L.A. Greene, "Nitric oxide delays the death of trophic factor–deprived PC12 cells and sympathetic neurons by a cGMP–mediated mechanism." J. Neurosci. 16 (1996) 2325–2334.

Fung, H.–L., "Nitrate therapy: is there an optimal substance and formulation?" Eur. Heart J. 12 (Supp A) (1991) 9–12.

Fung, H.–L., "Nitrate therapy: is there and optimal substance and formulation?" Eur. Heart J. 12 (Supp A) (1991) 9–12.

Furukawa, K., S.W. Barger, E.M. Blalock, and M.P. Mattson, "Activation of $K^+$ channels and suppression of neuronal activity by secreted β–amyloid precursor protein." Nature 379 (1996) 74–78.

Gaetani, P., A. Pasqualin, R. Rodriguez y Baena, E. Borasio, and F. Marzatico, "Oxidative stress in the human brain after subarachnoid hemorrhage." J. Neurosurg. 89 (1998) 748–754.

Goda, H., H. Ooboshi, H. Nakane, S. Ibayashi, S. Sadoshima, and M. Fujishima, "Modulation of ischemia–evoked release of excitatory and inhibitory amino acids by adenosine A1 receptor agonist." Eur. J. Pharmacol. 357 (1998) 149–155.

Gottron, F.J., H.S. Ying, and D.W. Choi, "Caspase inhibition selectively reduces the apoptotic component of oxygen–glucose deprivation–induced cortical neuronal cell death." Mol. Cell. Neurosci. 9 (1997) 159–169.

Haviv, R., L. Lindenboim, H. Li, J. Yuan, and R. Stein, "Need for caspases in apoptosis of trophic factor–deprived PC12 cells." J. Neurosci. Res. 50 (1997) 69–80.

Huang, F.P., L.F. Zhou, and G.Y. Yang, "Effects of mild hypothermia on the release of regional glutamate and glycine during extended transient focal cerebral ischemia in rats." Neurochem. Res. 23 (1998) 991–996.

Ibarrola, D., H. Seegers, A. Jaillard, M. Hommel, M. Decorps, and R. Massarelli, "The effect of eliprodil on the evolution of a focal cerebral ischaemia in vivo." Eur. J. Pharmacol. 352 (1998) 29–35.

Kim, Y.M., R.V. Talanian, and T.R. Billiar, "Nitric oxide inhibits apoptosis by preventing increases in caspase–3–like activity via two distinct mechanisms." J. Biol. Chem. 272 (1997) 31138–31148.

Kojda, G., M. Feelisch, and E. Noack, "Sulfhydryl–containing nitrate esters: a new class of nitric oxide donors." Cardiovasc. Drug Rev. 13 (1995) 275–288.

Lei, Sizhen Z., Z.–H. Pan, S.K. Aggarwal, H.–S.V. Chen, J. Hartman, N.J. Sucher, and S.A. Lipton, "Effect of Nitric Oxide Production on the Redox Modulatory Site of the NMDA Receptor–Channel Complex." Neuron. 8 (1992) 1087–1099.

Lipton, S.A., Y.–B. Choi, Z.–H. Pan, S. Z. Lei, H.–S.V. Chen, N.J. Sucher, J. Loscalzo, D.J. Singel and J.S. Stamler, "A redox–based mechanism for the neuroprotective and neurodestructive effects of nitric oxide and related nitroso–compounds." Nature 364 (1993) 626–632.

Lipton, S.A., "Prospects for clinically tolerated NMDA antagonists: open–channel blockers and alternative redox states of nitric oxide." Trends Neurol. Sci. 16 (1993) 527–532.

Louw, R., H.P.W. Vermeeren, J.J.A. Van Asten, and W.J. Ultée, "Reaction of Sulphides with Acyl Nitrates; a Simple and Rapid Method for Preparing Sulphoxides." J. Chem. Comm. (1976) 496–497.

Macdonald, R.L., and M. Stoodley, "Pathophysiology of cerebral ischemia." Neurol. Med. Chir. (Tokyo) 38 (1998) 1–11.

McDonald B.J. and B.M. Bennett, "Cytochrome P–450 mediated biotransformation of organic nitrates." Can. J. Physiol. Pharmacol. 68 (1990) 1552–1557.

McGuire J.J., D.J. Anderson and B.M. Bennett, "Inhibition of the Biotranformation and Pharmacological Actions of Glyceryl Trinitrate by the Flavoprotein Inhibitor, Diphenyleneiodonium Sulfate." J. Pharmacol. Exp. Ther. 271 (1994) 708–714.

Mizuno, A., K. Umemura, and M. Nakashima, "Inhibitory effect of MCI–186, a free radical scavenger, on cerebral ischemia folliwing rat middle cerebral artery occlusion." Gen. Pharmacol. 30 (1998) 575–578.

Morikawa, E., H. Mori, Y. Kiyama, M. Mishina, T. Asano, and T. Kirino, "Attenuation of Focal Ischemic Brain Injury in Mice Deficient in the ε1 (NR2A) Subunit of NMDA Receptor." J. Neurosci. 18 (1998) 9727–9732.

Namura, S., J. Zhu, K. Fink, M. Endres, A. Srinivasan, K.J. Tomaselli, J. Yuan, and M.A. Moskowitz, "Activiation and cleavage of caspase–3 in apoptosis induced by experimental cerebral ischemia." J. Neurosci. 18 (1998) 3659–3668.

Ni, B., X. Wu, Y. Su, D. Stephenson, E.B. Smalstig, J. Clemens, and S.M. Paul, "Transient global forebrain ischemia induces a prolonged expression of the caspase–3 mRNA in rat hippocampal CA1 pyramidal neurons." J. Cereb. Blood Flow Metab. 18 (1998) 248–256.

Nicholson, D.W., and N.A. Thornberry, "Caspases: killer proteases." Trends Biochem. Sci. 22 (1997) 301–306.

Nurse, S. and D. Corbett, "Neuroprotection After Several Days of Mild, Drug–Induced Hypothermia." J. Cereb. Blood Flow Metab. 16 (1996) 474–480.

O'Neill, M.J., A. Bond, P.L. Ornstein, M.A. Ward, C.A. Hicks, K. Hoo, D. Bleakman, and D. Lodge, "Decahydroisoquinolines: novel competitive AMPA/kainate antagonists with neuroprotective effects in global cerebral ischaemia." Neuropharmacol. 37 (1998) 1211–1222.

Ouellette, R.J., and R.J. Bertsch, "Formation of Nitrate Esters by the Oxidation of Alkenes and Cyclopropanes with Thallium (III) Nitrate in Pentane." J. Org. Chem. 41 (1976) 2782–2783.

Owais, M., G.C. Varshney, A. Choudhury, S. Chandra, and C.M. Gupta, "Chloroquine Encapsulated in Malaria–Infected Erythrocyte–Specific Antibody–Bearing Liposomes Effectively Controls Chloroquine–Resistant *Plasmodium berghei* infections in Mice." Antimicrob. Agents Chemother. 39 (1995) 180–184.

Pallarés, M., M. Darnaudéry, J. Day, M. Le Moal, and W. Mayo, "The neurosteroid pregnenolone sulfate infused into the nucleus basalis increases both acetylcholine release in the frontal cortex of amygdala and spatial memory." Neurosci. 87 (1998) 551–558.

Ranade, V.V., "Drug Delivery Systems. 1. Site–Specific Drug Delivery Using Liposomes as Carriers." J. Clin. Pharmacol. 29 (1989) 685–694.

Stewart, D.H., L.D. Hayward, and B.M. Bennett, "Differential biotransformation of the enantiomers of isoidide dinitrate in isolated rat aorta." Can. J. Physiol. Pharmacol. 67 (1989) 1403–1408.

Strejan, G.H., J.J. Gilbert, and J. St. Louis, "Suppression of Chronic–Relapsing Experimental Allergic Encephalomyelitis in Strain–13 Guinea Pigs by Administration of Liposome–Associated Myelin Basic Protein." J. Neuroimmunol. 7 (1984) 27–41.

Sydserff, S.G., A.J. Cross, K.J. West, and A.R. Green, "The effect of chlormethiazole on neuronal damage in a model of transient focal ischaemia." Br. J. Pharmacol. 114 (1995) 1631–1635.

Tagami, M., K. Yamagata, Y. Nara, H. Fujino. A. Kubota, F. Numano, and Y. Yamori, "Vitamin E prevents apoptosis in cortical neurons during hypoxia and oxygen reperfusion." Lab Invest. 78 (1998) 1415–1429.

Umemura, K., A. Shimakura, and M. Nakashima, "Neuroprotective effect of a novel AMPA receptor antagonist, YM90K, in a rat focal cerebral ishaemia." Brain Res. 773 (1997) 61–65.

Umezawa, F. and Y. Eto, "Liposome Targeting to Mouse Brain: Mannose as a Recognition Marker." Biochem. Biophys. Res. Commun. 153 (1988) 1038–1050.

Verrecchia C., A. Buisson, N. Lakhmeche, M. Plotkine, and R.G. Boulu, "Nitric Oxide and Cerebral Ischemia." Ann. N.Y. Acad. Sci. (1994) 341–347.

Wallace J.L., W. McKnight, P. Del Soldato, A.R. Baydoun, and G. Cirino, "Anti–Thrombotic Effects of a Nitric Oxide–releasing Gastric–sparing Aspirin Derivative." J. Clin. Invest. 96 (1995) 2711–2718.

Wu, J., Y. Wang, M.J. Rowan, and R. Anwyl, "Evidence for involvement of the cGMP–protein kinase G signaling sysem in the induction of long–term depression, but not long–term potentiation, in the dentate gyrus in vitro." J. Neurosci. 18 (1998) 3589–3596.

Yang, K., J.D. Artz, J. Lock, C. Sanchez, B.M. Bennett, A.B. Fraser, and G.R.J. Thatcher, "Synthesis of novel organic nitrate esters: guanylate cyclase activation and tissue relaxation." J. Chem. Soc., Perkin Trans. 1 (1996) 1073–1075.

Yang, Y.L., W.H. Pan, T.H. Chiu, and M.T. Lin, "Striatal glutamate release is important for development of ischemic damage to striatal neurons during rat heatstroke." Brain Res. 795 (1998) 121–127.

Yeates, R.A., "Possible mechanisms of activation of soluble guanylate cyclase by organic nitrates." Arzneim–Forsch./Drug Res. 42(II) (1992) 1314–1317.

Yeates, R.A., H. Laufen, and M. Leitold, "The reaction between organic nitrates and sulfhydryl compounds. A possible model system for the activation of organic nitrates." Mol. Pharm. 28 (1985) 555–559.

Zanzinger, J., M. Feelisch, and E. Bassenge, "Novel organic nitrates are potent dilators of large coronary arteries with reduced development of tolerance during long–term infusion in dogs: role of the sulfhydryl moiety." J. Cardiovas. Pharm. 23 (1994) 772–778.

| DEA (μM) | 0 | 25 | 100 |
|---|---|---|---|
| GABA (μM) | 20 | 20 | 20 |

15 min 250 nA
75 nA

| tBuSNO (μM) | 0 | 44 | 0 | 0 |
|---|---|---|---|---|
| GTN (μM) | 0 | 0 | 44 | 0 |
| GABA (μM) | 20 | 20 | 20 | 20 |

NITRATE ESTERS AND THEIR USE FOR NEUROLOGICAL CONDITIONS

RELATED APPLICATIONS

This application is a continuation-in-part of our application Ser. No. 08/867,856, filed Jun. 3, 1997 and issued Mar. 16, 1999 as U.S. Pat. No. 5,883,122, which is in turn a continuation-in-part of our application Ser. No. 08/658,145, filed Jun. 4, 1996 and issued Sep. 15, 1998 as U.S. Pat. No. 5,807,847, the disclosures of both being hereby incorporated by reference in their entirety.

FIELD OF THE INVENTION

This invention relates to nitrate esters and use thereof in effecting neuroprotection, mitigating neurodegeneration and/or effecting cognition enhancement. More particularly, this invention relates to organic nitrates having therapeutic utility as neuroprotective agents and/or cognition enhancers. The invention still more particularly relates to nitrate esters bearing a sulfur or phosphorus atom β or γ to a nitrate group and their congeners which have therapeutic utility as neuroprotective agents and/or cognition enhancers.

BACKGROUND OF INVENTION

The nitrate ester glyceryl trinitrate (GTN) or nitroglycerin, has been used as a vasodilator in the treatment of angina pectoris for over a hundred years, and the dominant contemporary belief is that GTN exerts its therapeutic effect through in vivo release of nitric oxide (NO). Other organic nitrates, such as isosorbide dinitrate, have also been identified as effective and clinically important vasodilators. NO itself has been identified as Endothelium Derived Relaxing Factor (EDRF) and several classes of compounds, for example nitrosothiols, in addition to organic nitrates, have been proposed as NO donors or NO prodrugs. Well-known examples of these classes of compounds and one nitrate, GTN itself, have been suggested to demonstrate neurotoxic or neuroprotective effects by dint of interactions with the redox modulatory site of the N-methyl-D-aspartate (NMDA) excitatory amino acid receptor. Thus GTN is firstly a potent vasodilator and secondly possesses potential neuroprotective properties. Several attempts have been made to increase the efficacy or potency of alternative organic nitrates as vasodilators relative to GTN, for example, by incorporation of propanolamine or cysteine functionalities. However, no attempt has been made to separately regulate the vasodilatory and neuroprotective effects of GTN. Indeed, postural hypotension, weakness and other signs of cerebral ischemia are adverse effects, associated with the vasodilatory effects of GTN and observed in treatment, which are highly contraindicative of GTN itself, and by extrapolation GTN derivatives (1,2,3-trinitratopropane derivatives), as clinically useful neuroprotective therapeutic agents.

OBJECTS AND SUMMARY OF THE INVENTION

In as much as the potent vasodilatory effects of organic nitrates may prove (a) deleterious to, or alternatively (b) synergistic with the neuroprotective effects of GTN, it is postulated herein that regulation of these two effects is required for development of new and useful neuroprotective therapeutic agents. Further, it is postulated that such regulation may be achieved through use of an appropriate organic nitrate, such as, for example, nitrate esters incorporating sulfur-containing or phosphorus-containing functionalities into the structure of the nitrate esters or through use of their congeners. Interaction of organic nitrates with amino acid neurotransmitter receptors, including the NMDA receptor, will provide examples of compounds with neuroprotective properties, but modulation of the γ-aminobutyric acid type A (GABA$_A$) receptor response will provide examples of organic nitrates capable of cognition enhancement. Stimulation of cerebral soluble guanylyl cyclase (GCase) by organic nitrates, in particular selectively over arterial GCase, will provide examples of compounds with neuroprotective properties. Organic nitrates bearing antioxidant functionalities and those capable of inhibiting apoptosis will also provide examples of compounds with neuroprotective properties. These postulates are based, in part, on bioassay data on such compounds. Thus, there is a need for synthetic organic nitrates, such as, for example, nitrate esters containing sulfur or phosphorous functionalities or their congeners, as new and useful therapeutic agents for use in effecting neuroprotection, mitigating neurodegeneration and/or effecting cognition enhancement. It will be appreciated, therefore, that these compounds can be used for treatment conditions including but not limited to: stroke; Parkinson's disease; Alzheimer's disease; Huntington's disease; multiple sclerosis; amylotrophic lateral sclerosis; AIDS-induced dementia; epilepsy; alcoholism; alcohol withdrawal; drug-induced seizures; viral/bacterial/fever-induced seizures; trauma to the head; hypoglycemia; hypoxia; myocardial infarction; cerebral vascular occlusion; cerebral vascular hemorrhage; hemorrhage; environmental excitotoxins of plant, animal and marine origin; dementias if all type, trauma, drug-induced brain damage, aging.

It is an object of the present invention to provide provide novel organic nitrates, including aliphatic nitrate esters bearing a sulfur or phosphorus moiety β or γ to a nitrate group, or congeners thereof. Another object of the present invention is to provide methods for making such novel organic nitrates. Another object of the invention is to provide methods for effecting neuroprotection, mitigating neurodegeneration and/or effecting cognition enhancement employing organic nitrates. Another object of the present invention is to provide novel drugs as neuroprotective agents. Yet another object of the present invention is to provide novel drugs for use in cognition enhancement.

This invention provides novel compounds, methods and pharmaceutical compositions which are useful in the treatment of neurological disorders requiring mitigation of neurodegeneration, neuroprotection and/or cognition enhancement. Methods of the invention involve administering to a subject in need thereof a therapeutic compound which provides neuroprotection or cognition enhancement. Accordingly, the compositions and methods of the invention are useful for effecting neuroprotection or cognition enhancement in disorders in which neurotoxic damage occurs. The methods of the invention can be used therapeutically to treat conditions including but not limited to: stroke; Parkinson's disease; Alzheimer's disease; Huntington's disease; multiple sclerosis; amylotrophic lateral sclerosis; AIDS-induced dementia; epilepsy; alcoholism; alcohol withdrawal; drug-induced seizures; viral/bacterial/fever-induced seizures; trauma to the head; hypoglycemia; hypoxia; myocardial infarction; cerebral vascular occlusion; cerebral vascular hemorrhage; hemorrhage; environmental excitotoxins; dementias of all type, trauma, drug-induced brain damage, and aging or can be used prophylactically in a subject susceptible or predisposed to these conditions. In certain embodiments, a therapeutic compound used in the method of the invention preferably can interact with GCase effecting neuroprotection and/or cognition enhancement. In other embodiments, a therapeutic compound used in the method of the invention preferably can modulate glutamate and/or non-glutamate neuroreceptor interactions effecting neuroprotection and/or cognition enhancement.

The invention relates to organic nitrates, i.e., nitrate esters. In one aspect, the invention provides a method including the step of administering to a subject an effective amount of a therapeutic compound having the formula (Formula I):

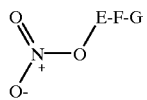

wherein E, F, G are organic radicals which may contain inorganic counterions, such that neurodegeneration is mitigated in the subject.

In another aspect, the invention provides a method including the step of administering to a subject an effective amount of a therapeutic compound having the formula (Formula I):

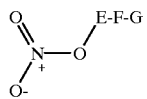

wherein E, F, G are organic radicals which may contain inorganic counterions, such that cognition enhancement is effected.

In a further aspect, the invention provides use of therapeutic compounds that mitigate neurodegeneration, effect neuroprotection and/or effect cognition enhancement in a subject to which the therapeutic compound is administered, the compounds having the formula (Formula II):

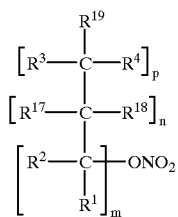

in which: m and n and p are integers from 0 to 10;

$R^{3,17}$ are each independently hydrogen, a nitrate group, or A;

$R^{1,4}$ are each independently hydrogen or A;

where A is selected from: a substituted or unsubstituted aliphatic group (preferably a branched, or straight-chain aliphatic moiety having from 1 to 24 carbon atoms in the chain, which optionally contains O, S, $NR^6$ and unsaturations in the chain, optionally bearing from 1 to 4 hydroxy, nitrate, amino or aryl, or heterocyclic groups; an unsubstituted or substituted cyclic aliphatic moiety having from 3 to 7 carbon atoms in the aliphatic ring, which optionally contains O, S, $NR^6$ and unsaturations in the ring, optionally bearing from 1 to 4 hydroxy, nitrate, or amino or aryl, or heterocyclic groups; an unsubstituted or substituted aliphatic moiety constituting a linkage of from 0 to 5 carbons, between $R^1$ and $R^3$ and/or between $R^{17}$ and $R^4$, which optionally contains O, S, $NR^6$ and unsaturations in the linkage, and optionally bearings from 1 to 4 hydroxy, nitrate, amino or aryl, or heterocyclic groups); a substituted or unsubstituted aliphatic group (preferably a branched, cyclic or straight-chain aliphatic moiety having from 1 to 24 carbon atoms in the chain), containing carbonyl linkages (e.g. C=O, C=S, C=NOH), which optionally contains O, S, $NR^6$ and unsaturations in the chain, optionally bearing from 1 to 4 hydroxy, nitrate, amino or aryl, or heterocyclic groups; a substituted or unsubstituted aryl group; a heterocyclic group; amino (including alkylamino, dialkylamino (including cyclic amino, diamino and triamino moieties), arylamino, diarylamino, and alkylarylamino); hydroxy; alkoxy; a substituted or unsubstituted aryloxy;

$R^2$, $R^5$, $R^{18}$, $R^{19}$ are optionally hydrogen, A, or X—Y;

where X is F, Br, Cl, $NO_2$, $CH_2$, $CF_2$, O, NH, NMe, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_2HM$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, C(O), $C(O)R^{12}$, $C(O)(OR^{13})$, $PO_2H$, $PO_2M$, $P(O)(OR^{14})$, $P(O)(R^{13})$, SO, $SO_2$, $C(O)(SR^{13})$, $SR^5$, $SSR^7$ or $SSR^5$;

Y is F, Br, Cl, $CH_3$, $CF_2H$, $CF_3$, OH, $NH_2$, $NHR^6$, $NR^6R^7$, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_2HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, $C(O)R^{12}$, $C(O)(OR^{13})$, $C(O)(SR^{13})$, $SR^5$, $SSR^7$ or $SSR^5$, or does not exist;

$R^6$, $R^7$, $R^8$, $R^9$, $R^{10}$, $R^{11}$, $R^{12}$, $R^{13}$, $R^{14}$, $R^{15}$, $R^{16}$ are the same or different alkyl or acyl groups containing 1–24 carbon atoms which may contain 1–4 $ONO_2$ substituents; or $C_1$–$C_6$ connections to $R^1$–$R^4$ cyclic derivatives, or are each independently hydrogen, a nitrate group, or W;

M is H, $Na^+$, $K^+$, $NH_4^+$, $N^+H_kR^{11}_{(4-k)}$ where k is 0–3, or other pharmaceutically acceptable counterion;

and with the proviso that, when m=n=p=1; $R^{19}$, $R^2$, $R^{18}$, $R^1$=H; $R^{17}$, $R^3$ are nitrate groups; that $R^4$ is not H or $C_1$–$C_3$ alkyl.

Preferred therapeutic compounds for use in the invention include compounds in which $R^{19}$ X—Y. In some preferred embodiments: $R^{19}$ is X—Y and $R^5$, $R^6$, $R^8$, $R^9$, $R^{10}$, $R^{12}$, $R^{13}$, $R^{14}$, $R^{15}$, $R^{16}$ are the same or different alkyl groups containing 1–24 carbon atoms which may contain 1–4 $ONO_2$ substituents, or $C_1$ or $C_2$ connections to $R^1$–$R^3$ in cyclic derivatives; $R^1$ and $R^3$ are the same or different and selected from H, $C_1$–$C_4$ alkyl chains, which may inlude one O, linking $R^1$ and $R^3$ to form pentosyl, hexosyl, cyclopentyl, or cycohexyl rings, which rings optionally bear hydroxyl substituents; $R^2$ and $R^4$ are the same or different and selected from H, a nitrate group, $C_1$–$C_4$ alkyl optionally bearing 1–3 nitrate group, and acyl groups (—$C(O)R^5$); and $R^7$, $R^{11}$ are the same or different $C_1$–$C_8$, alkyl or acyl.

In certain embodiments in which $R^{19}$ is X—Y, m, p=1, and n=0.

In other embodiments in which $R^{19}$ is X—Y, X is selected from: $CH_2$, O, NH, NMe, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, C(O), $C(O)R^{12}$, $C(O)(OR^{13})$, $PO_2M$, $P(O)(OR^{16})$, $P(O)(R^{13})$, SO, $SO_2$, $C(O)(SR^{13})$, and $SSR^4$.

In other embodiments in which $R^{19}$ is X—Y, Y is selected from CN, $N_2H_2R^{13}$, $N_2HR^{13}R^{14}$, $N_3$, SCN, $SCN_2H_2(R^{15})_2$, $SC(O)N(R^{15})_2$, $SC(O)NHR^{15}$, $SO_3M$, $SR^4$, $SO_2M$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, $C(O)R^{12}$, $C(O)(SR^{13})$, $SR^5$, $SSR^5$, or does not exist.

In certain embodiments, X and/or Y contain a sulfur-containing functional group. In some embodiments, a compound of the invention according to Formula II comprises a heterocyclic functionality, more preferably, a nucleoside or nucleobase. In further embodiments, a compound of the invention comprises a carbocyclic functionality, more preferably, a steroidal or carbohydrate moiety.

In another aspect, a therapeutic compound which is employed in methods of the invention is represented by the formula (Formula III):

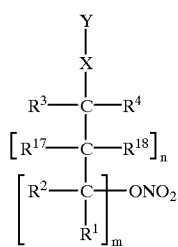

in which: m is 1–10; $R^{1-18}$, X, and Y have the meaning as defined above. In some embodiment, $R^6$–$R^{16}$ are the same or different alkyl or acyl groups containing 1–24 carbon atoms which may contain 1–4 $ONO_2$ substituents, or $C_1$–$C_6$ connections to $R^1$–$R^4$ in cyclic derivatives. In certain preferred embodiments, $R^{18}$ is A and n=1.

In another aspect, the invention provides novel compounds useful for mitigating neurodegeneration, effecting neuroprotection and/or effecting cognition enhancement which are represented by the structure of Formula 3.

In a further aspect, a therapeutic compound according to the invention is represented by the formula (Formula IV):

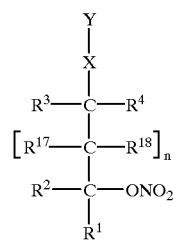

in which: $R^3$, $R^1$=H; n, $R^2R^{4-18}$, X, and Y have the meaning as defined above. In certain preferred embodiments, X is $CH_2$ or does not exist, and Y is selected from: F, Br, Cl, $CH_3$, $CF_2H$, $CF_3$, OH, $NH_2$, $NHR_6$, $NR_6R_7$, CN, NHOH, $N_2H_3$, $N_2H_2R_{13}$, $N_2HR_{13}R_{14}$, $N_3$, S, SCN, $SCN_2H_2(R_{15})_2$, $SCN_2H_3(R_{15})$, $SC(O)N(R_{15})_2$, $SC(O)NHR_{15}$, $SO_3M$, SH, $SR_7$, $SO_2M$, $S(O)R_8$, $S(O)_2R_9$, $S(O)OR_8$, $S(O)_2OR_9$, $PO_2HM$, $PO_3M_2$, $P(O)(OR_{15})(OR_{16})$, $P(O)(OR_{16})(OM)$, $P(O)(R_{15})(OR_8)$, $P(O)(OM)R_{15}$, $CO_2M$, $CO_2H$, $CO_2R_{11}$, $C(O)R_{12}$, $C(O)(OR_{13})$, $C(O)(SR_{13})$, $SR_5$, $SSR_7$ and $SSR_5$. In certain embodiments, $R_2$ and $R_4$ are optionally H, a nitrate group or a connection to $R_5$–$R_{16}$ in cyclic derivatives.

By one particular aspect of this invention there is provided an aliphatic nitrate ester containing at least one nitrate group, in which a S or P atom is situated β or γ to a nitrate group, or congeners thereof, having the general formula (Formula IV*):

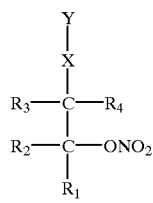

where X is $CH_2$, O, NH, NMe, CN, NHOH, $N_2H_3$, $N_2H_2R_{13}$, $N_2HR_{13}R_{14}$, $N_3$, S, SCN, $SCN_2H_2(R_5)_2$, $SCN_2H_3(R_5)$, $SC(O)N(R_5)_2$, $SC(O)NHR_5$, $SO_3M$, SH, $SR_7$, $SO_2M$, $S(O)R_8$, $S(O)_2R_9$, $S(O)OR_8$, $S(O)_2OR_9$, $PO_3M_2$, $P(O)(OR_5)(OR_6)$, $P(O)(OR_6)(OM)$, $P(O)(R_5)(OR_8)$, $P(O)(OM)R_5$, $CO_2M$, $CO_2H$, $CO_2R_{11}$, C(O), $C(O)R_{12}$, $C(O)(OR_{13})$, $PO_2M$, $P(O)(OR_{14})$, $P(O)(R_{13})$, SO, $SO_2$, $C(O)(SR_{13})$, $SR_4$, or $SSR_4$;

Y is SCN, $SCN_2H_2(R_5)_2$, $SC(O)NHR_5$, $SC(O)N(R_5)_2$, $SR_4$, $SR_{10}$, $SSR_{10}$, $SO_2M$, $SO_3M$, $PO_3HM$, $PO_3M_2$, $P(O)(OR_5)(OR_6)$, or $P(O)(OR_6)(OM)$, CN, $N_3$, $N_2H_2R_{13}$, $N_2HR_{13}R_{14}$, $CO_2M$, $CO_2H$, $CO_2R_{11}$, $C(O)R_{12}$, $C(O)(SR_{13})$, or does not exist;

$R_5$, $R_6$, $R_8$, $R_9$, $R_{10}$, $R_{12}$, $R_{13}$, $R_{14}$, $R_{15}$, $R_{16}$, are the same or different alkyls containing 1–12 carbon atoms which may contain 1–4 $ONO_2$ substituents or $C_1$ or $C_2$ connections to $R_1$–$R_3$ in cyclic derivatives;

$R_7$, $R_{11}$ are $C_1$–$C_8$, alkyl or acyl;

$R_2$ and $R_4$ are the same or different and selected from H, $OHO_2$, $C_1$–$C_4$ alkyl optionally bearing 1–3 nitrate groups, and acyl groups (—$C(O)R_{10}$);

$R_1$ and $R_3$ are the same or different and selected from H, $C_1$–$C_4$ alkyl and chains, which may rings optionally bear hydroxyl substituents; and M is H, $Na^+$, K include one O, linking $R_1$ and $R_3$ to form pentosyl, hexosyl, cyclopentyl or cycohexyl rings, which $^+$, $NH_4^+$ or $N^+H_AR_{17(4-n)}$ where n is 0–3;

with the proviso that, when X is O, Y is not $COR_{12}$; and with the proviso that, when $R_3$ is H, $R_6$ is not ethyl or n-butyl;

and pharmaceutically acceptable salts thereof.

The invention further provides a pharmaceutical composition comprising an effective amount of nitrate ester of Formula IV*, in admixture with a physiologically acceptable carrier therefor. The invention still further provides a method for effecting neuroprotection in a subject in need thereof comprising administering to said subject an effective amount of a nitrate ester of Formula IV*.

In yet another aspect of the invention, compounds according to the invention are represented by the formula (Formula V):

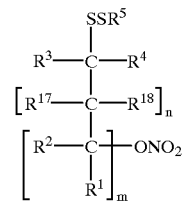

where m, n, $R^{1-18}$, X, and Y have the meaning as defined above.

In another aspect, the invention provides methods for preparing organic nitrates represented by the structure of Formula V.

The therapeutic compounds of the invention are administered to a subject by a route which is effective for mitigating neurodegeneration, effecting neuroprotection and/or effecting cognition enhancement. Suitable routes of administration include sublingual, oral, buccal, transdermal, nasal, subcutaneous, intravenous, intramuscular and intraperitoneal injection. Preferred routes of administration are intravenous, subcutaneous and transdermal administration, particularly for effecting neuroprotection. In addition, for effecting cognition enhancement, oral administration may be preferred. The therapeutic compounds can be administered with a pharmaceutically acceptable vehicle.

The invention also provides methods for treating a disease state associated with neurodegeneration by administering to a subject an effective amount of a therapeutic compound having a formula as set forth above, such that a disease state associated with neurodegeneration is treated.

The invention provides methods for effecting neuroprotection and/or cognition enhancement by administering to a subject an effective amount of a therapeutic compound having a formula described above, such that neuroprotection and/or cognition enhancement is effected.

The invention further provides pharmaceutical compositions for treating neurodegeneration. The pharmaceutical compositions include a therapeutic compound of the invention in an amount effective to mitigate neurodegeneration in admixture with a pharmaceutically acceptable carrier therefor.

The invention also provides packaged pharmaceutical compositions for treating neurodegeneration. The packaged pharmaceutical compositions include a therapeutic compound of the invention and instructions for using the pharmaceutical composition for treatment of neurodegeneration.

DETAILED DESCRIPTION OF INVENTION

Figure 1:
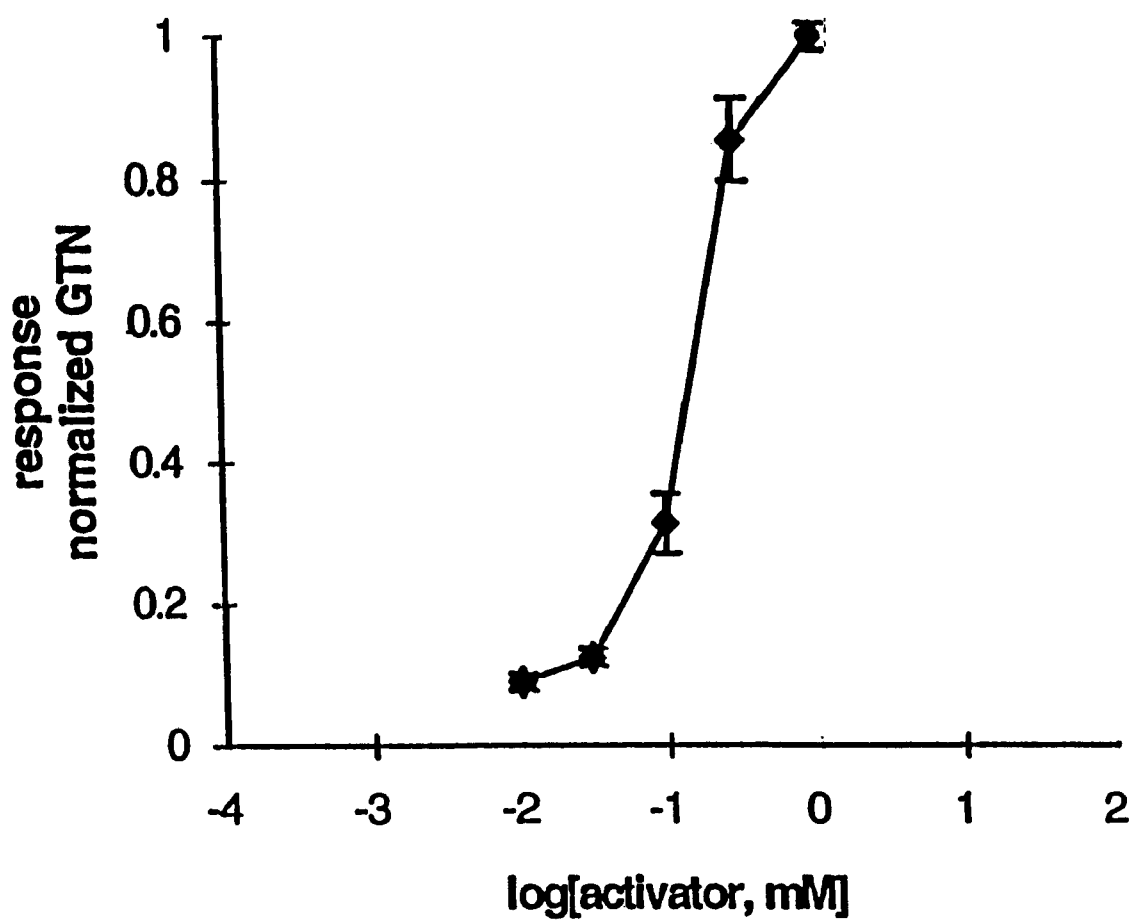
FIG. 1 is a graph showing the effects of GTN with added L-cysteine (2 mM) on soluble guanylyl cyclase (GCase) activity in rat aorta homogenate. Bars represent the mean ± standard errors calculated separately for each point.

This invention pertains to methods and compositions useful for treating neurodegeneration. The methods of the invention involve administering to a subject a therapeutic compound which effects neuroprotection and/or cognition enhancement. Neuroprotection and/or cognition enhancement can be effected, for example, by modulating an interaction with guanylyl cyclase (GCase), a glutamate or non-glutamate neuroreceptor or attenuating free radical damage. GCase is the enzyme responsible for cGMP production in various areas of the brain.

According to certain aspects of the invention, neurodegeneration is mitigated by stimulating cerebral GCase. One of the major targets for organic nitrates is GCase activation, resulting in the production of cGMP. Experimental evidence obtained in a number of in vitro model systems supports the notion that elevated levels of cGMP help to prevent apoptotic (programmed) cell death. Thus, a cGMP-dependent mechanism significantly increases the aurvival of trophic factor-deprived PC12 cells and rat sympathetic neurons (Farinelli et al., 1996), and of primary cultures of rat embryonic motor neurons (Estevez et al., 1998). The mechanism of action for organic nitrates in preventing apoptotic cell death may be inhibition of caspase-3 activation indirectly through elevations in cGMP levels or directly via protein S-nitrosylation of the enzyme by an NO-intermediate (Kim et al., 1997). Caspase-3 is a member of the cysteine protease family of enzymes that are essential for the execution step in apoptosis (Cohen, 1997; Nicholson and Thornberry, 1997). Activation of caspase-3 is required for apoptotic cell death in trophic factor-deprived PC12 cells (Haviv et al., 1997) and in glutamate-mediated apoptotic cell death of cultured cerebellar granule neurons (Du et al., 1997). In animal models of cerebral ischemia, caspase-3 activity is induced and may be responsible for the apoptotic component of delayed neuronal cell death (Chen et al., 1998; Namura et al., 1998; Ni et al., 1998). Inhibitors of caspase-3 significantly decrease the apoptotic component of delayed neuronal cell death in response to ischemic injury both in vitro (Gottron et al., 1997) and in vivo (Endres et al., 1998). A secreted region of the Alzheimer's disease β-amyloid precursor protein lowers intracellular calcium levels and provides neuroprotective effects on target cells through increases in cGMP levels and activation of protein kinase G (Barger et al., 1995; Furukawa et al., 1996). In preferred embodiments of the methods of the invention, nitrated molecules that have the capacity to activate GCase directly or via release of an NO-containing intermediate are used to modulate GCase activity.

According to certain other aspects of the invention, cognition enhancement (e.g., improved memory performance) is achieved by stimulating cerebral GCase. Several lines of experimental evidence support the notion that GCase and cGMP are involved in the formation and retention of new information. cGMP has been directly implicated in both long-term potentiation (LTP) and long-term depression (LTD), which are proposed cellular models for learning and memory (Arancio et al., 1995; Wu et al., 1998). In animal models, elevation of hippocampal cGMP levels leading to increased protein kinase G activity has been shown to be important for retention and consolidation of new learning (Bernabeu et al., 1996, 1997). Thus, stimulation of cerebral GCase activity is expected to improve learning and memory performance in individuals in whom cognitive abilities are impaired by injury, disease, or aging.

We have shown that novel organic nitrate esters have differential effects to activate soluble GCase and to cause cGMP accumulation in vascular and brain tissue. There is a clear dissociation between the vascular relaxation effects of organic nitrate esters and ability to effect neuroprotection. Activation of GCase and accumulation of cGMP have been shown to be important in the neuroprotection of hippocampal brain slices subjected to a period of in vitro ischemia.

Cerebral ischemia results in marked increases in the release of the excitatory amino acid glutamate in the affected brain region (Bullock et al., 1998; Huang et al., 1998; Yang et al., 1998). In both humans (Bullock et al., 1998) and experimental animals (Huang et al., 1998; Goda et al., 1998; Yang et al., 1998), the amount of glutamate released during ischemia is positively correlated with the extent of brain injury. In experimental animal models of cerebral ischemia, decreased release of glutamate during ischemia (Goda et al., 1998) or blockade of glutamate receptors with antagonists (Ibarrola et al., 1998; O'Neill et al., 1998; Umemura et al., 1997) significantly reduces the extent of brain injury. However, these interventions are only effective when given prior to or during the ischemic insult. To be broadly useful, a therapeutic intervention is preferably effective when administered after the period of ischemia. We have designed a class of novel organic nitrate esters having high efficacy in effecting neuroprotection in vivo in models of transient global and focal cerebral ischemia when given after the ischemic insult. It will be appreciated, therefore, that these organic nitrates can be used for treatment of conditions including but not limited to: stroke, Parkinson's disease; Alzheimer's disease; Huntington's disease; multiple sclerosis; amylotrophic lateral sclerosis; AIDS-induced dementia; epilepsy; alcoholism; alcohol withdrawal; drug-induced seizures; viral/bacterial/fever-induced seizures; trauma to the head; hypoglycemia; hypoxia; myocardial infarction; cerebral vascular occlusion; cerebral vascular hemorrhage; hemorrhage; environmental excitotoxins of plant, animal and marine origin; and the like.

The direct effects of organic nitrates on amino acid neurotransmitter receptors has been tested using the Xenopus oocyte expression system and two-electrode voltage-clamp recording methods. Organic nitrates were found to have direct, modulatory effects on $GABA_A$ receptor function (see Working Examples below). These allosteric modulatory effects of organic nitrates were not shared by direct NO-generating compounds, indicating a novel mechanism of action for organic nitrates to interact with $GABA_A$ receptors. In behavioural models of learning and memory, drugs which decrease $GABA_A$ receptor function improve performance on learning and memory tasks (Venault et al., 1992). Thus, the behavioural effect of organic nitrates, developed to act as modulators of $GABA_A$ receptor function, will be to improve memory performance and cognition in patient populations. It will be appreciated, therefore, that these organic nitrates can be used for treatment of conditions including but not limited to: stroke; dementias of all type; trauma; drug-induced brain damage; and aging.

According to certain aspects of the invention, neurodegeneration is mitigated by inhibition of free radical damage. Reoxygenation and reperfusion after a period of ischemia contributes significantly to the development of brain injury. Oxygen radicals, especially superoxide and peroxynitrite, formed in the period after an ischemic event may initiate processes such as breakdown of membrane lipids (lipid peroxidation), leading to loss of cell membrane integrity and inhibition of mitochondrial function (Macdonald and Stoodley, 1998; Gaetani et al, 1998). Oxidative stress is also believed to be one factor involved in initiation of apoptotic neuronal cell death (Tagami et al., 1998). In experimental animal models of ischemic brain injury, free radical scavengers and enhanced activity of superoxide dismutase have been found to reduce the extent of neuronal injury and cell death (Chan et al., 1998; Mizuno et al., 1998; Tagami et al., 1998). In preferred embodiments of the methods of the invention, nitrated molecules which have the capacity to inhibit production of free radicals and/or which act as free radical scavengers are used to attenuate the brain injury that occurs after a period of cerebral ischemia. It will be appreciated by those skilled in the art, that any organic nitrate in which vasodilatory potency is reduced and neuroprotective potency increased, represents a new and useful therapeutic agent for use in neuroprotection, particularly in treatment of conditions including but not limited to: stroke; Parkinson's disease; Alzheimer's disease; Huntington's disease; multiple sclerosis; amylotrophic lateral sclerosis; AIDS-induced dementia; epilepsy; alcoholism; alcohol withdrawal; drug-induced seizures; viral/bacterial/fever-induced seizures; trauma to the head; hypoglycemia; hypoxia; myocardial infarction; cerebral vascular occlusion; cerebral vascular hemorrhage; hemorrhage; environmental excitotoxins of plant, animal and marine origin. GTN itself, proposed as a neuroprotective agent, has no clinical utility as a neuroprotective agent in therapy owing to its extraordinarily high vasodilatory potency. Similarly, by extrapolation, 1,2,3-trinitratopropane (GTN) derivatives are not expected to have clinical utility as neuroprotective agents in therapy owing to their especially high vasodilatory potency.

It will additionally be appreciated by those skilled in the art, that the use in therapy of any organic nitrate in cognition enhancement, represents a new and useful treatment for cognition enhancement, particularly in treatment of conditions including but not limited to: stroke; dementias of all type, trauma, drug-induced brain damage, and aging.

"Mitigating neurodegeneration" as use herein involves effecting neuroprotection, inhibiting or preventing neurodegeneration, and/or ameliorating the manifestations or impact of neurodegeneration. Such amelioration includes effecting cognition enhancement, as is quantified by tests known in the art (e.g., Venault et al. 1992, incorporated herein by reference), "Modulating" a biological process as used herein (for example, modulating the activity of the non-glutamate neuroreceptors), encompasses both increasing (positively modulating) and decreasing (negatively modulating) such activity, and thus inhibition, potentiation, agonism, and antagonism of the biological process.

In particular, the therapeutic compounds of the invention comprise at least one nitrate group. The nitrate groups(s) can optionally be covalently bound to a carrier moiety or molecule (e.g., an aromatic group, an aliphatic group, peptide, steroid, nucleoside, peptidomimetic, steroidomimetic, or nucleoside analogue, or the like). In addition to functioning as a carrier for the nitrate functionality, the carrier moiety or molecule can enable the compound to traverse biological membranes and to be biodistributed preferentially, without excessive or premature metabolism. Further, in addition to functioning as a carrier for the nitrate functionality, the carrier moiety or molecule can enable the compound to exert amplified neuroprotective effects and/or cognition enhancement through synergism with the nitrate functionality.

In one aspect, the invention provides a method of treating a neurological condition and/or preventing an undesirable mental condition (e.g., memory loss) including the step of administering to a subject an effective amount of a therapeutic compound capable of mitigating neurodegeneration which has at least one nitrate group. In one embodiment, the therapeutic compound is capable of effecting neuroprotection. In another embodiment of the invention, the therapeutic compound is capable of effecting cognition enhancement. The therapeutic compound has the formula (Formula I):

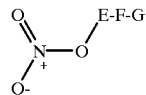

wherein E, F, G are organic radicals which may contain inorganic counterions; so that a neurological condition is treated.

In another aspect, the invention provides a pharmaceutical composition including a physiologically acceptable carrier and a compound having the formula (Formula I):

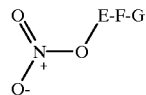

wherein: E, F, G are organic radicals which may contain inorganic counterions; such that neurodegeneration is mitigated. The composition is employed for mitigating neurodegeneration, effecting neuroprotection and/or effecting cognition enhancement.

In another aspect, therapeutic compounds of the invention that effect neuroprotection and/or effect cognition enhancement in a subject to which the therapeutic compound is administered have the formula (Formula II):

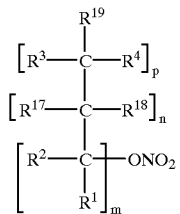

in which, m, n, p are integers from 0 to 10; $R^{3,17}$ are each independently hydrogen, a nitrate group, or A; $R^{1,4}$ are each independently hydrogen or A, where A is selected from: a substituted or unsubstituted aliphatic group (preferably a branched, or straight-chain aliphatic moiety having from 1 to 24 carbon atoms in the chain, which optionally contains O, S, $NR^6$ and unsaturations in the chain, optionally bearing from 1 to 4 hydroxy, nitrate, amino or aryl, or heterocyclic groups; an unsubstituted or substituted cyclic aliphatic moiety having from 3 to 7 carbon atoms in the aliphatic ring, which optionally contains O, S, $NR^6$ and unsaturations in the ring, optionally bearing from 1 to 4 hydroxy, nitrate, amino or aryl, or heterocyclic groups; an unsubstituted or substituted aliphatic moiety constituting a linkage of from 0 to 5 carbons, between $R^1$ and $R^3$ and/or between $R^{17}$ and $R^4$, which optionally contains O, S, $NR^6$ and unsaturations in the linkage, and optionally bearing from 1 to 4 hydroxy, nitrate, amino or aryl, or heterocyclic groups); a substituted or unsubstituted aliphatic group (preferably a branched, cyclic or straight-chain aliphatic moiety having from 1 to 24 carbon atoms in the chain), containing carbonyl linkages (e.g., C=O, C=S, C=NOH), which optionally contains O, S, $NR^6$ and unsaturations in the chain, optionally bearing from 1 to 4 hydroxy, nitrate, amino or aryl, or heterocyclic groups; a substituted or unsubstituted aryl group; a heterocyclic group; amino (including alkylamino, dialkylamino (including cyclic amino, diamino and triamino moieties), arylamino, diarylamino, and alkylarylamino); hydroxy; alkoxy; a substituted or unsubstituted aryloxy; $R^2$, $R^5$, $R^{18}$, $R^{19}$ are optionally hydrogen, A, or X-Y; where X is F, Br, Cl, $NO_2$, $CH_2$, $CF_2$, O, NH, NMe, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_2HM$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, C(O), $C(O)R^{12}$, $C(O)(OR^{13})$, $PO_2H$, $PO_2M$, $P(O)(OR^{14})$, $P(O)(R^{13})$, SO, $SO_2$, $C(O)(SR^{13})$, $SR^5$, $SSR^7$ or $SSR^5$; Y is F, Br, Cl, $CH_3$, $CF_2H$, $CF_3$, OH, $NH_2$, $NHR^6$, $NR^6R^7$, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_2HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, $C(O)R^{12}$, $C(O)(OR^{13})$, $C(O)(SR^{13})$, $SR^5$, $SSR^7$ or $SSR^5$, or does not exist; $R^6$, $R^7$, $R^8$, $R^9$, $R^{10}$, $R^{11}$, $R^{12}$, $R^{13}$, $R^{14}$, $R^{15}$, $R^{16}$ are the same or different alkyl or acyl groups containing 1–24 carbon atoms which may contain 1–4 $ONO_2$ substituents; or $C_1$–$C_6$ connections to $R^1$–$R^4$ in cyclic derivatives; or are each independently hydrogen, a nitrate group, or A; M is H, $Na^+$, $K^+$, $NH_4^+$, $N^+H_kR^{11}_{(4-k)}$ where k is 0–3, or other pharmacuetically acceptable counterion.

Pharmaceutical compositions comprising a compound of Formula II in admixture with a pharmaceutically acceptable carrier therefor are provided by the invention. The invention further provides methods of mitigating neurodegeneration, effecting neuroprotection and/or effecting cognition enhancement in a subject comprising the step of administering a compound of Formula II to a subject such that said mitigation and/or said neuroprotection an/or cognition enhancement occurs.

According to this aspect of the invention, preferred therapeutic compounds for effecting neuroprotection and/or cognition enhancement in a subject to which the compound is administered include compounds in which $R^{19}$ is X-Y. In some preferred embodiments: $R^{19}$ is X-Y and $R^5$, $R^6$, $R^8$, $R^9$, $R^{10}$, $R^{12}$, $R^{13}$, $R^{14}$, $R^{15}$, $R^{16}$ are the same or different alkyl groups containing 1–24 carbon atoms which may contain 1–4 $ONO_2$ substituents, or $C_1$ or $C_2$ connections to $R^1$–$R^3$ in cyclic derivatives; $R^1$ and $R^3$ are the same or different and selected from H, $C_1$–$C_4$, alkyl chains, which may inlude one O, linking $R^1$ and $R^3$ to form pentosyl, hexosyl, cylcopentyl, or cyclohexyl rings, which rings optionally bear hydroxyl substituents; $R^2$ and $R^4$, are the same or different and selected from H, a nitrate group, $C_1$–$C_4$ alkyl optionally bearing 1–3 nitrate group, and acyl groups (—$C(O)R^5$); and $R^7$, $R^{11}$ are the same or different $C_1$–$C_8$, alkyl or acyl.

In certain embodiments in which $R^{19}$ is X-Y, m, p=1, and n=0. In other embodiments in which $R^{19}$ is X-Y, X is selected from: $CH_2$, O, NH, NMe, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, C(O), $C(O)R^{12}$, $C(O)(OR^{13})$, $PO_2M$, $P(O)(OR^{14})$, $P(O)(R^{13})$, SO, $SO_2$, $C(O)(SR^{13})$, $SSR^4$. In certain other embodiments in which $R^{19}$ is X-Y, Y is selected from CN, $N_2H_2R^{13}$, $N_2HR^{13}R^{14}$, $N_3$, SCN, $SCN_2H_2(R^{15})_2$, $SC(O)N(R^{15})_2$, $SC(O)NHR^{15}$, $SO_3M$, $SR^4$, $SO_2M$, $PO_3HM$, $PO_2M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, $C(O)R^{12}$, $C(O)(SR^{13})$, $SR^5$, $SSR^5$, or does not exist. In some embodiments, X and/or Y contains a sulfur-containing functional group. In certain embodiments, the compound of the invention comprises a heterocyclic functionality, more preferably, a nucleoside or nucleobase. In other embodiments, the compound of the invention comprises a carbocyclic functionality, more preferably, a steroidal or carbohydrate moiety.

In another aspect of the invention, a therapeutic compound of the invention is represented by the formula (Formula III):

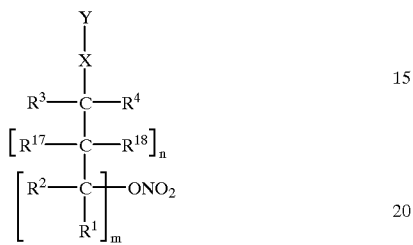

in which: m, n are 1–10; $R^{1-18}$, X, and Y have the meaning as defined above. In certain preferred embodiments, $R^6$–$R^{16}$ are the same or different alkyl or acyl groups containing 1–24 carbon atoms which may contain 1–4 $ONO_2$ substituents, or $C_1$–$C_6$ connections to $R^1$–$R^4$ in cyclic derivatives. In certain preferred embodiments, $R^{18}$ is A and m=n=1.

Pharmaceutical compositions comprising a compound of Formula III in admixture with a pharmaceutically acceptable carrier therefor are provided by the invention. The invention further provides methods of mitigating neurodegeneration, effecting neuroprotection and/or effecting cognition enhancement in a subject comprising the step of administering a compound of Formula III to a subject such that said mitigation and/or said neuroprotection and/or cognition enhancement occurs.

Examples and preferred embodiments of compounds of the invention according to Formula III are set forth below:

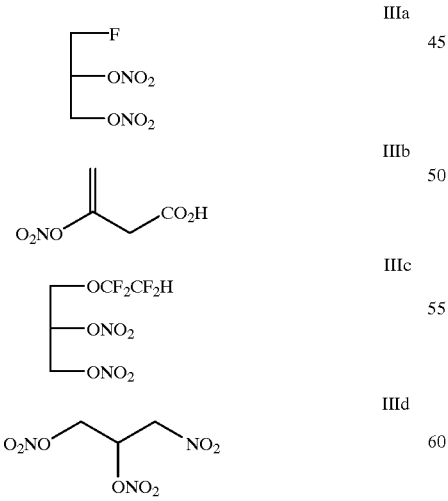

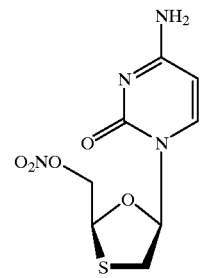

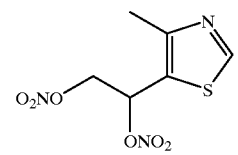

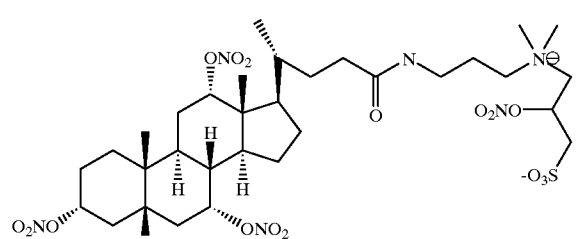

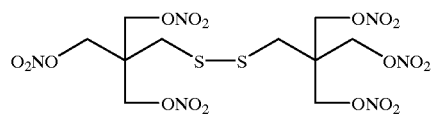

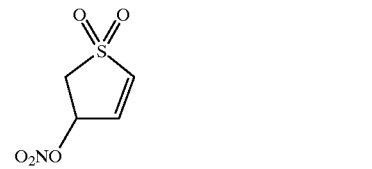

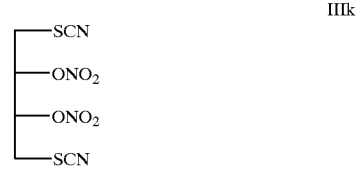

-continued

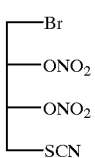

IIIl

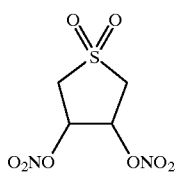

IIIm

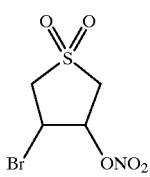

IIIn

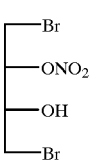

IIIo

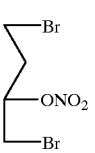

IIIp

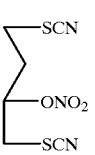

IIIq

In another aspect of the invention, a therapeutic compound of the invention can be represented by the formula (Formula IV):

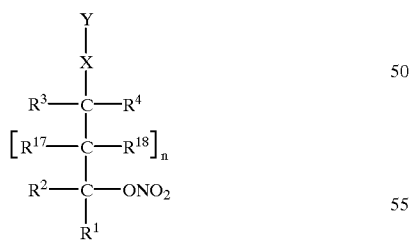

in which n=0, X is $CH_2$ or does not exist, and Y is selected from F, Br, Cl, $CH_3$, $CF_2H$, $CF_3$, OH, $NH_2$, $NHR_6$, $NR_6R_7$, CN, NHOH, $N_2H_3$, $N_2H_2R_{13}$, $N_2HR_{13}R_{14}$, $N_3$, S, SCN, $SCN_2H_2(R_{15})_2$, $SCN_2H_3(R_{15})$, $SC(O)N(R_{15})_2$, $SC(O)NHR_{15}$, $SO_3M$, SH, $SR_7$, $SO_2M$, $S(O)R_8$, $S(O)_2R_3$, $S(O)OR_8$, $S(O)_2OR_9$, $PO_2HM$, $PO_3M_2$, $P(O)(OR_{15})(OR_{16})$, $P(O)(OR_{16})(OM)$, $P(O)(R_{15})(OR_8)$, $P(O)(OM)R_{15}$, $CO_2M$, $CO_2H$, $CO_2R_{11}$, $C(O)R_{12}$, $C(O)(OR_{13})$, $C(O)(SR_{13})$, $SR_5$, $SSR_7$ or $SSR_5$. $R_2$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are as defined above. In certain preferred embodiments, $R_2$ and $R_4$ are optionally H, a nitrate group or a connection to $R_5$–$R_{16}$ in cyclic derivatives.

Pharmaceutical compositions comprising a compound of Formula IV in admixture with a pharmaceutically acceptable carrier therefor are provided by the invention. The invention further provides methods of mitigating neurodegeneration, effecting neuroprotection and/or effecting cognition enhancement in a subject comprising the step of administering a compound of Formula IV to a subject such that said mitigation and/or said neuroprotection and/or cognition enhancement occurs.

Examples and preferred embodiments of compounds of the invention according to Formula IV are set forth below:

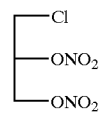

IVa 3

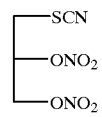

IVb 5

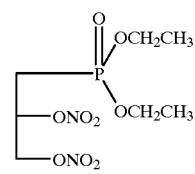

IVc 8

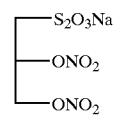

IVd 9

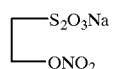

IVe 10

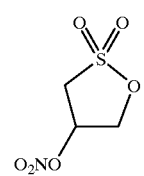

IVf 16

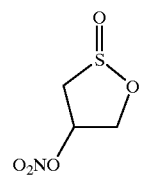

IVg 17

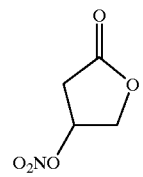

IVh 18

-continued

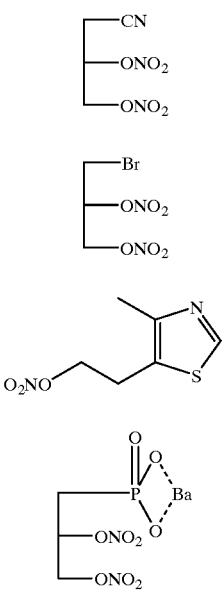

IVi

IVj

IVk 61

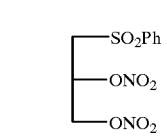

IVl

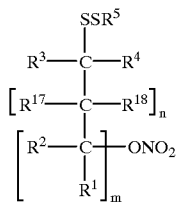

IVm

In yet another aspect of the invention, a compound of the invention can be represented by the formula (Formula V):

$$\begin{matrix} & SSR^5 \\ R^3-& C-R^4 \\ \left[R^{17}-& C-R^{18}\right]_n \\ \left[R^2-& C-ONO_2\right] \\ & R^1 \end{matrix}_m$$

in which $R_2$ is optionally H or a connection to $R_5$ in cyclic derivatives, $R_4$ is H or a nitrate group, and $R_5$ is as described above.

Pharmaceutical compositions comprising a compound of Formula V in admixture with a pharmaceutically acceptable carrier therefor are provided by the invention. The invention further provides methods of mitigating neurodegeneration, effective neuroprotection and/or effecting cognition enhancement in a subject comprising the step of administering a compound of Formula V to a subject such that said mitigation and/or said neuroprotection and/or cognition enhancement occurs.

Examples and preferred embodiments of compounds of the invention according to formula V (Formulae Va–c) are set forth below:

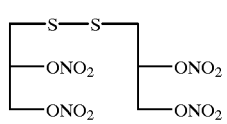

Va 15

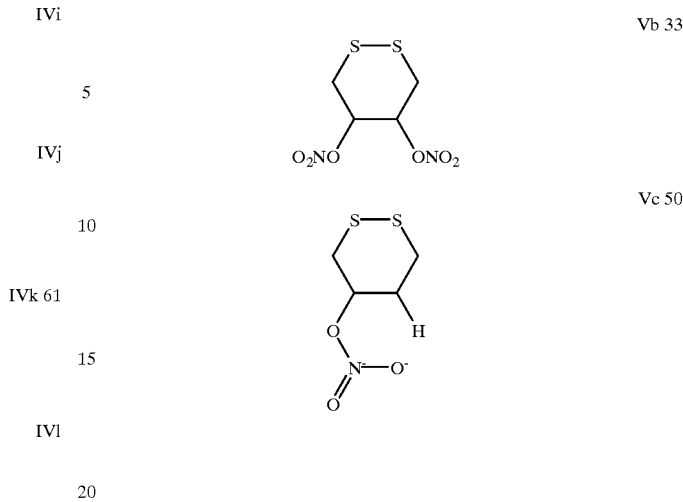

Table 1 lists data determined for compounds of the invention per art-recognized characterization techniques.

TABLE 1

| | $^1$H NMR | $^{13}$C NMR |
|---|---|---|
| IIIa | (CDCl$_3$): 5.34–5.57(1H, dm, $^3J_{HF}$20.6), 4.53–4.87(4H, superposition several multiplets, O$_2$NO—C$\underline{H}_2$ + C$\underline{H}_2$F, $^2J_{HF}$ 46.7, $^4J_{HF}$ 0.66) | (CDCl$_3$): 79.47(d, $^1J_{CF}$ 177), 76.73(d, $^2J_{CF}$ 20.6), 67.84 (d, $^3J_{CF}$ 6.87) |
| IIIb | (CDCl$_3$): δ | (CDCl$_3$): δ |
| IIIc | (CDCl$_3$): δ 5.7(1H, t, $^2J_{HF}$ 54), 5.45(1H, m), 4.5–4.9 (2H, m), 4.15–4.35(1H, m) | (CDCl$_3$): δ 75.55, 68.05, 60.76 |
| IIId | (CDCl$_3$): δ 5.46(1H, m), 4.80–4.87 (1H, dd, J 3.5, 12.9), 4.65–4.72(1H, dd, J 6.2, 12.9), 3.7–3.8(2H, m) | (CDCl$_3$): δ 77.24, 68.57, 39.86 |
| IIIf | (CDCl$_3$) δ 8.72(s, 1H), 5.38(t, 1H), 4.6(d, 2H), 2.45(s, 3H) | — |
| IIIg | (DMSOd$_6$) C$\underline{H}$ONO$_2$ only: δ 4.8–5.8 | (DMSOd$_6$) $\underline{C}$ONO$_2$ only: δ 85.68, 84.17, 82.47, 76.50 |
| IIIh | (CD$_3$OD) δ 4.85(3H, m), 3.5(1H, m) | (CD$_3$OD) δ 70.61, 36.74 |
| IIIi | (CDCl$_3$): δ 6.95(dd, 1H), 6.71 (dd, 1H), 6.09(m, 1H), 3.80(dd, 1H), 3.32(dd, 1H) | (CDCl$_3$: δ 137.9, 132.5, 76.6, 52.9 |
| IIIj | (CDCl$_3$): δ 5.62(2H, m), 3.60(4H, m) | (CDCl$_3$): δ 77.87, 25.22 |
| IIIk | (CD$_3$CN): δ 3.45(m, 2H), 5.72(m, 2H) | (CD$_3$CN): δ 79.98, 28.87 |
| IIIl | — | (CD$_3$CN): δ 79.48, 33.45, 28.47 |
| IIIm | (DMSOd$_6$): δ 5.97(m, 2H), 3.80(m, 4H) | (DMSOd$_6$): δ 78.84, 52.60 |
| IIIn | (CDCl$_3$): δ 5.73(m, 1H), 4.62 (m, 1H), 3.96–3.77(m, 1H), 3.58–3.32(m, 1H) | (CDCl$_3$): δ 81.47, 57.85, 53.50, 38.75 |
| IIIo | — | (CDCl$_3$): δ 81.24, 69.79, 33.26, 27.24 |
| IIIp | (CDCl$_3$): δ 5.36(m, 1H), 3.11–3.60 (m, 4H), 2.33(m, 2H) | (CDCl$_3$): δ 78.92, 33.66, 30.64, 27.36 |
| IIIq | (CDCl$_3$): δ 5.47(m, 1H), 3.53–3.05 (m, 4H), 2.29(m, 2H) | (CDCl$_3$): δ 81.32, 37.12, 32.97, 30.98 |
| IVi | (CDCl$_3$): δ 5.45(1H, m), 4.83 (1H, dd), 4.65(1H, dd), 2.9(2H, m) | (CD$_3$OD): δ 116.44, 75.37, 71.20, 19.19 |
| IVk | (CDCl$_3$) δ 8.55(s, 1H), 4.55(t, 2H), 3.15(t, 2H), 2.37(s, 3H) | (CDCl$_3$) δ 150.9, 150.7, 125.3, 72.53, 24.47, 15.18 |
| IVm | (CDCl$_3$): δ 7.5–8.0(arom, 5H), 5.7(1H, m), 4.94(1H, dd), 4.62(1H, dd), 3.5(2H, m) | (CDCl$_3$): δ 135.45, 134.79, 129.81, 27.95, 73.08, 70.04, 54.73 |
| Vb | (CDCl$_3$) δ 5.56(m, 2H), 3.38–2.95(m, 4H) | (CD$_3$OD) δ 85.93, 32.77 |
| Vc | (CDCl$_3$): δ 5.85–5.91(1H, m), 4.50–4.58(1H, m), 3.22–3.29(1H, | (CDCl$_3$): δ 87.6, 74.96, 36.20, 31.54 |

TABLE 1-continued

| $^1$H NMR | $^{13}$C NMR |
|---|---|
| dd, J 5.47, 12.78), 2.97–3.05(1H, dd, J 4.6, 11.88), 2.82–2.90 (1H, dd, J 2.87, 12.78), 2.74–2.83(1H, dd, J 3.15, 11.9) | |

Methods for preparing organic nitrates represented by the structures of Formula III are provided by the invention and taught herein, particularly in the Working Examples below.

It will be noted that the structure of some of the compounds of this invention includes asymmetric carbon atoms. It is to be understood accordingly that the isomers (e.g., enantiomers, diastereomers) arising from such asymmetry are included within the scope of this invention. Such isomers can be obtained in substantially pure form by classical separation techniques and by asymmetric synthesis. For the purposes of this application, unless expressly noted to the contrary, a compound shall be construed to include both the R and S stereoisomers at each stereogenic center.

In certain embodiments, a therapeutic compound of the invention comprises a cation (i.e., in certain embodiments, one of X or Y includes a cation, e.g., in the compound of formula IVd). If the cationic group is a proton, then the compound is considered an acid. If the proton is replaced by a metal ion or its equivalent, the compound is a salt. Pharmaceutically acceptable salts of the therapeutic compound are within the scope of the invention. For example, M can be a pharmaceutically acceptable alkali metal (e.g., Li, Na, K), ammonium alkaline earth metal (e.g. Ca, Ba, Mg), higher valency cation, or polycationic counter ion (e.g., polyammonium cation) (see e.g., Berge et al., 1977). It will be appreciated that the stoichiometry of an anionic portion of the compound to a salt-forming cation will vary depending on the charge of the anionic portion of the compound and the charge of the counterion. Preferred pharmaceutically acceptable salts include a sodium, potassium, or calcium salt, but other salts are also contemplated within their pharmaceutically acceptable range.

The therapeutic compound of the invention can be administered in a pharmaceutically acceptable vehicle. As used herein "pharmaceutically acceptable vehicle" includes any and all solvents, excipients, dispersion media, coatings, antibacterial and antifungal agents, isotonic and absorption delaying agents, and the like which are compatible with the activity of the compound and are physiologically acceptable to the subject. An example of the pharmaceutically acceptible vehicle is buffered normal saline (0.15 M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

Carrier or substituent moieties useful in the present invention may also include moieties which allow the therapeutic compound to be selectively delivered to a target organ. For example, delivery of the therapeutic compound to the brain may be enhanced by a carrier moiety using either active or passive transport (a "targeting moiety"). Illustratively, the carrier molecule may be a redox moiety, as described in, for example, U.S. Pat. Nos. 4,540,654 and 5,389,623, both to Bodor. These patents disclose drugs linked to dihydropyridine moieties which can enter the brain, where they are oxidized to a charged pyridinium species which is trapped in the brain. Thus drugs accumulate in the brain. Other carrier moieties include compounds, such as amino acids or thyroxine, which can be passively or actively transported in vivo. Such a carrier moiety can be metabolically removed in vivo, or can remain intact as part of an active compound. Structural mimics of amino acids (and other actively transported moieties) including peptidomimetics, are also useful in the invention. As used herein, the term "peptidomimetic" is intended to include peptide analogues which serve as appropriate substitutes for peptides in interactions with, for example, receptors and enzymes. The peptodomimetic must possess not only affinity, but also efficacy and substrate function. That is, a peptidomimetic exhibits functions of a peptide, without restriction of structure to amino acid constituents. Peptidomimetics, methods for their preparation and use are described in Morgan et al. (1989), the contents of which are incorporated herein by reference. Many targeting moieties are known, and include, for example, asialoglycoproteins (see e.g., Wu, U.S. Pat. No. 5,166,320) and other ligands which are transported into cells via receptor-mediated endocytosis (see below for further examples of targeting moieties which may be covalently or non-covalently bound to a target molecule).

In the methods of the invention, neurodegeneration in a subject is mitigated, and/or neuroprotection and/or cognition enhancement is effected, by administering a therapeutic compound of the invention to the subject. The term "subject" is intended to include living organisms in which the particular neurological condition to be treated can occur. Examples of subjects include humans, apes, monkeys, cows, sheep, goats, dogs, cats, mice, rats, and transgenic species thereof. As would be apparent to a person of skill in the art, the animal subjects employed in the working examples set forth below are reasonable models for human subjects with respect to the tissues and biochemical pathways in question, and consequently the methods, therapeutic compounds and pharmaceutical compositions directed to same. As evidenced by Mordenti (1986) and similar articles, dosage forms for animals such as, for example, rats can be and are widely used directly to establish dosage levels in therapeutic applications in higher mammals, including humans.

In particular, the biochemical cascade initiated by cerebral ischemia is generally accepted to be identical in mammalian species (Mattson and Scheff, 1994; Higashi et al., 1995). In light of this, pharmacological agents that are neuroprotective in animal models such as those described herein are believed to be predictive of clinical efficacy in humans, after appropriate adjustment of dosage. Specifically, there are comparable memory-deficit patterns between brain-damaged rats and humans, which indicates that the rat can serve as an excellent animal model to evaluate the efficacy of pharmacological treatments or brain damage upon memory (Kesner, 1990). The only approved drug for the clinical treatment of occlusive stroke in humans is tissue plasminogen activator, which is administered at a dose of 0.9 mg/kg by intravenous injection (Wittkowsky, 1998). This drug is also effective in protecting the rat brain subjected to cerebral ischemia by occlusion of the middle cerebral artery, when administered at a dose of 10 mg/kg intravenously (Jiang et al., 1998). Thus, the rat model of focal cerebral ischemia used in the development of the novel organic nitrate esters described herein has been shown to be shown to be predictive of clinical efficacy with at least one other class of pharmacological agents.

As would also be apparent to a person skilled in the art, the invention further encompasses methods of the invention employed ex vivo or in vitro. For example, the Working Examples describe studies utilizing tissue homogenates according to the invention. Furthermore, diagnostic tests or studies of efficacy of selected compounds may conveniently be performed ex vivo or in vitro, including in animal models. Such tests, studies and assays are within the scope of the invention.

Administration of the compositions of the present invention to a subject to be treated can be carried out using known procedures, at dosages and for periods of time effective to mitigate neurodegeneration, and/or to effect neuroprotection and/or cognition enhancement in the subject. An effective amount of the therapeutic compound necessary to achieve a therapeutic effect may vary according to factors such as the amount of neurodegeneration that has already occurred at the clinical site in the subject, the age, sex, and weight of the subject, and the ability of the therapeutic compound to mitigate neurodegeneration and/or to effect neuroprotection and/or cognition enhancement in the subject. Dosage regimens can be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention (e.g., Va) is between 0.5 and 500 mg/kg of body weight per day. In an aqueous composition, preferred concentrations for the active compound (i.e., the therapeutic compound that can mitigate neurodegeneration and/or effect neuroprotection and/or cognition enhancement) are between 5 and 500 mM, more preferably between 10 and 100 mM, and still more preferably between 20 and 50 mM.

The therapeutic compounds of the invention can be effective when administered orally. Accordingly, a preferred route of administration is oral administration. Alternatively, the active compound may be administered by other suitable routes such as transdermal, subcutaneous, intraocular, intravenous, intramuscular or intraperitoneal administration, and the like (e.g., by injection). Depending on the route of administration, the active compound may be coated in a material to protect the compound from the action of acids, enzymes and other natural conditions which may inactivate the compound.

The compounds of the invention can be formulated to ensure proper distribution in vivo. For example, the blood-brain barrier (BBB) excludes many highly hydrophilic compounds. To ensure that the therapeutic compounds of the invention cross the BBB, they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., Ranade et al., 1989). Exemplary targeting moieties include folate and biotin (see, e.g., U.S. Pat. No. 5,416,016 to Low et al.); mannosides (Umezawa et al., 1988); antibodies (Bloeman et al., 1995; Owais et al., 1995); and surfactant protein A receptor (Briscoe et al., 1995). In a preferred embodiment, the therapeutic compounds of the invention are formulated in liposomes; in a more preferred embodiment, the liposomes include a targeting moiety.

Delivery and in vivo distribution can also be affected by alteration of an anionic group of compounds of the invention. For example, anionic groups such as phosphonate or carboxylate can be esterified to provide compounds with desirable pharmacokinetic, pharmacodynamic, biodistributive, or other properties. Exemplary compounds include IVI and pharmaceutically acceptable salts or esters thereof.

To administer the therapeutic compound by other than parenteral administration, it may be necessary to coat the compound with, or co-administer the compound with, a material to prevent its inactivation. For example, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally (e.g., intramuscularly, intravenously, intraperitoneally, intraspinally, or intracerebrally). Dispersions can be prepared in glycerol, liquid polyethylene glycols, and mixtures thereof and in oils. Under ordinary conditions of storage and use, these preparations may contain a preservative to prevent the growth of microorganisms. Pharmaceutical compositions suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, liquid polyethylene glycol, and the like), suitable mixtures thereof, and vegetable oils. The proper fluidity can be maintained, for example, by the use of a coating such as lecithin, by the maintenance of the required particle size in the case of dispersion, and by the use of surfactants.

Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filter sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient (i.e., the therapeutic compound) optionally plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of neurological conditions in subjects.

Therapeutic compositions can be administered in time-release or depot form, to obtain sustained release of the therapeutic compounds over time. The therapeutic compounds of the invention can also be administered transdermally (e.g., by providing the therapeutic compound, with a suitable carrier, in patch form).

Active compounds are administered at a therapeutically effective dosage sufficient to mitigate neurodegeneration and/or to effect neuroprotection and/or cognition enhancement in a subject. A "therapeutically effective dosage" preferably mitigates neurodegeneration by about 20%, more preferably by about 40%, even more preferably by about 60%, and still more preferably by about 80% relative to untreated subjects. The ability of a compound to mitigate neurodegeneration can be evaluated in model systems that may be predictive of efficacy in mitigating neurodegeneration in human diseases, such as animal model systems known in the art (including, e.g., the method of transient middle cerebral artery occlusion in the rat) or by in vitro methods, (including, e.g., the assays described herein).

It will be appreciated that the ability of a compound of the invention to mitigate neurodegeneration will, in certain embodiments, be evaluated by observation of one or more symptoms or signs associated with neurodegeneration in vivo. Thus, for example, the ability of a compound to mitigate neurodegeneration may be associated with an observable improvement in a clinical manifestation of the underlying neurodegeneration-related disease state or condition, or a slowing or delay in progression of symptoms of the condition. Thus, monitoring of clinical manifestations of disease can be useful in evaluating the neurodegeneration-mitigating efficacy of a compound of the invention.

The method of the invention is useful for treating neurodegeneration associated with any disease in which neurodegeneration occurs. Clinically, neurodegeneration can be associated with conditions including but not limited to: stroke; Parkinson's disease; Alzheimer's disease; Huntington's disease; multiple sclerosis; amylotrophic lateral sclerosis; AIDS-induced dementia; epilepsy; alcoholism; alcohol withdrawal; drug-induced seizures; viral/bacterial/fever-induced seizures; trauma to the head; hypoglycemia; hypoxia; myocardial infarction; cerebral vascular occlusion; cerebral vascular hemorrhage; hemorrhage; environmental excitotoxins of plant; animal and marine origin; dementias of all type; trauma; drug-induced brain damage; and aging; or result from surgical procedures such as cardiac bypass.

Novel compounds according to the invention can be synthesized by methods set forth herein (see, e.g., Working Examples) or in our patents U.S. Pat. No. 5,807,847 and U.S. Pat. No. 5,883,122. Various compounds for use in the methods of the invention are commercially available and/or can be synthesized by standard techniques. In general, nitrate esters can be prepared from the corresponding alcohol, oxirane or alkene by standard methods, that include: nitration of alcohols and oxiranes, mixed aqueous/organic solvents using mixtures of nitric and sulfuric acid and/or their salts, with temperature control (see Yang et al., 1996); nitration of alcohols and oxiranes in acetic anhydride using nitric acid or its salts with or without added acid catalyst, with temperature control (see, e.g., Louw et al., 1976); nitration of an alcohol with a nitronium salt, e.g. a tetrafluoroborate; nitration of an alkene with thallium nitrate in an appropriate solvent (see Ouellette et al., 1976).

The following Examples further illustrate the present invention and are not intended to be limiting in any respect. Those skilled in the art will recognize, or be able to ascertain using no more than routine experimentation, numerous equivalents to the specific procedures described herein. Such equivalents are considered to be within the scope of this invention and are covered by the claims.

Working Examples

Example 1

Characterization of guanylyl cyclase activation

Figure 2:
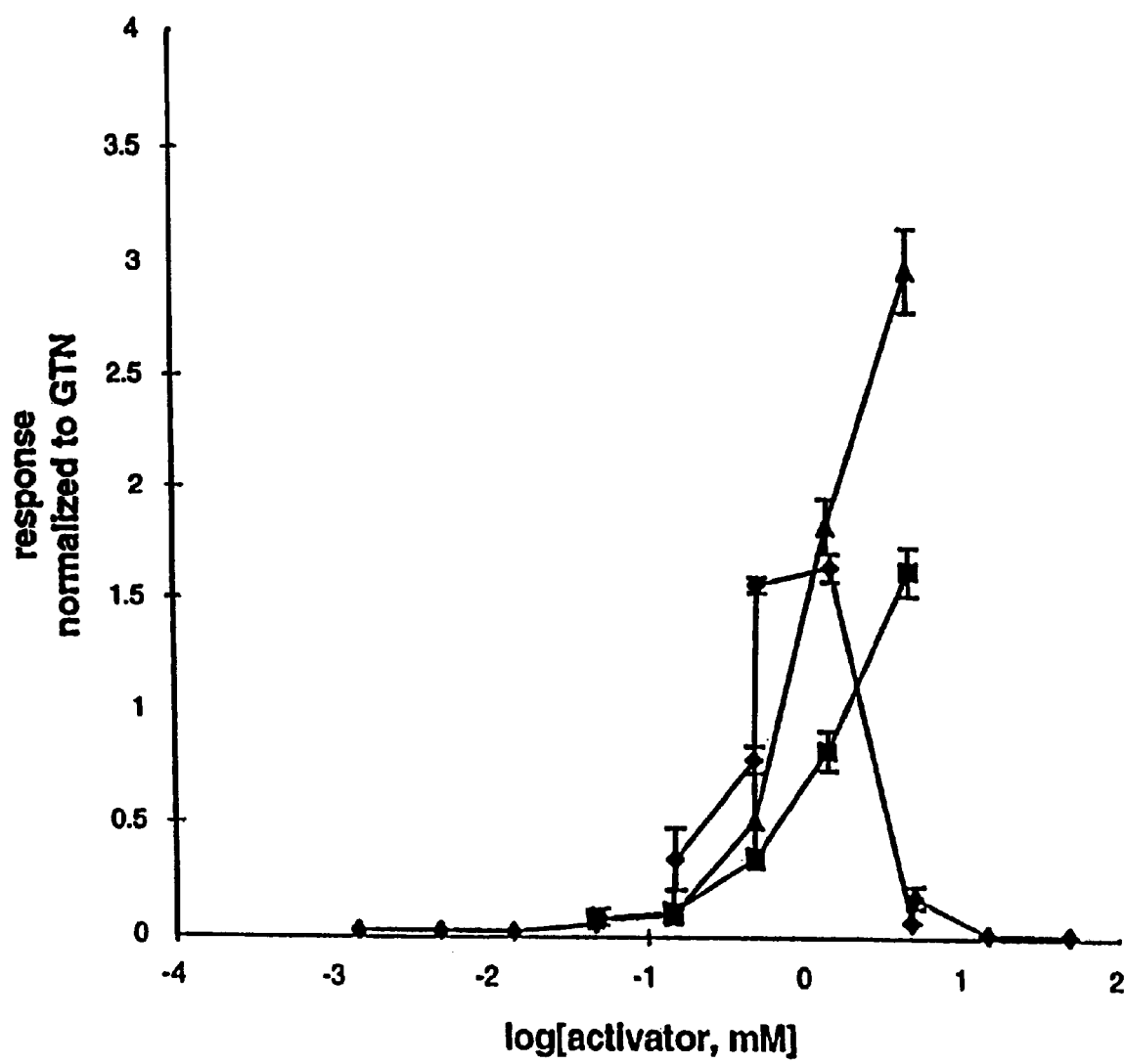
FIG. 2 is a graph showing the effect of IVd neat (diamonds); with added L-cysteine (2 mM, triangles); with added dithiothreitol (2 mM, DTT, squares); on soluble GCase activity in rat aorta homogenate normalized to the maximal GTN response. Bars represent the mean ± standard errors calculated separately for each point.
Figure 3:
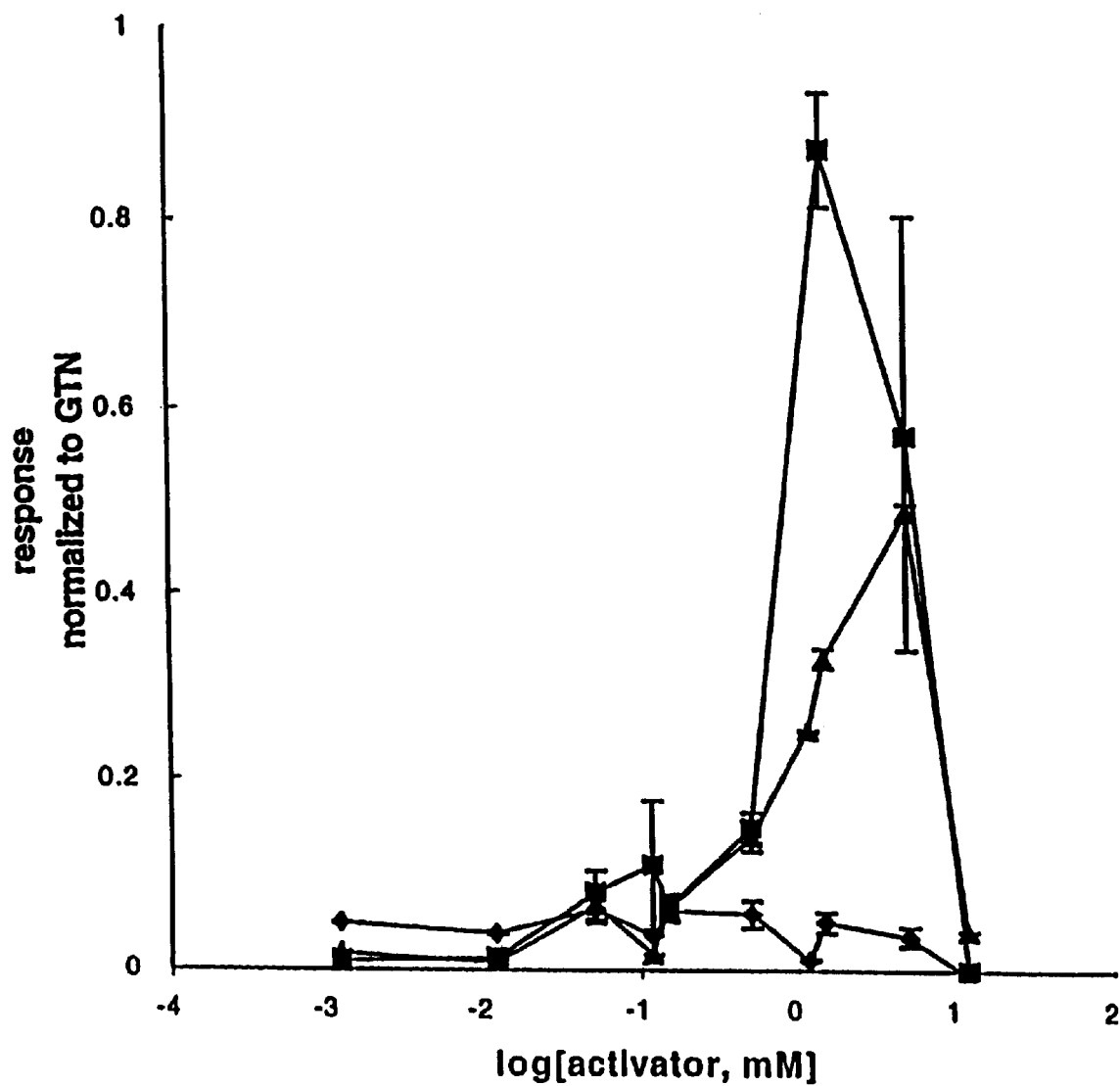
FIG. 3 is a graph showing the effect of IVg neat (diamonds); with added L-cysteine (2 mM, triangles); with added dithiothreitol (2 mM, DTT, squares); on soluble GCase activity in rat aorta homogenate, normalized to the maximal GTN response. Bars represent the mean ± standard errors calculated separately for each point.
Figure 4:
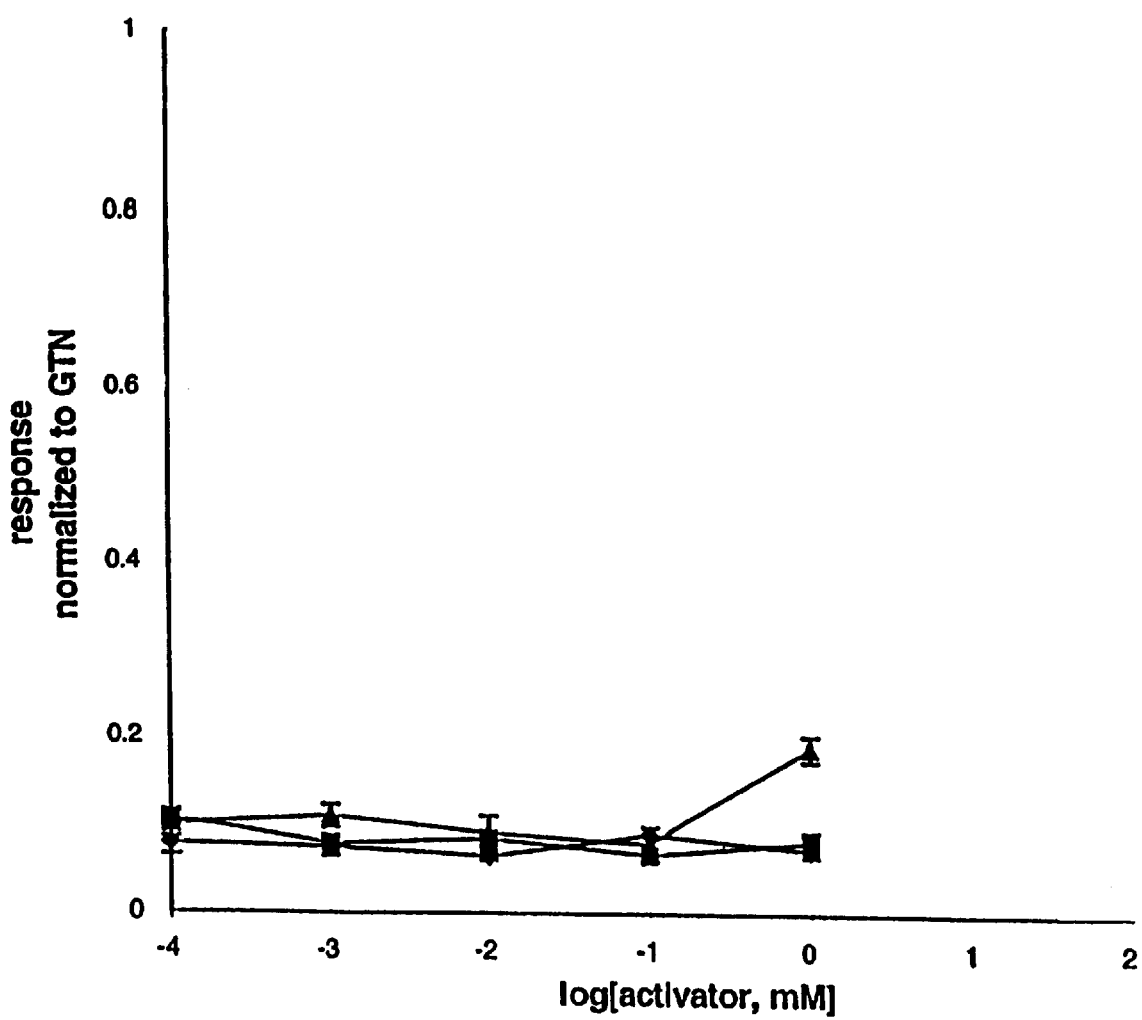
FIG. 4 is a graph showing the effects of IVb neat (diamonds); with added L-cysteine (2 mM, triangles); with added dithiothreitol (2 mM, DTT, squares); on soluble GCase activity in rat aorta homogenate, normalized to maximal GTN response. Bars represent the mean ± standard errors calculated separately for each point.
Figure 5:
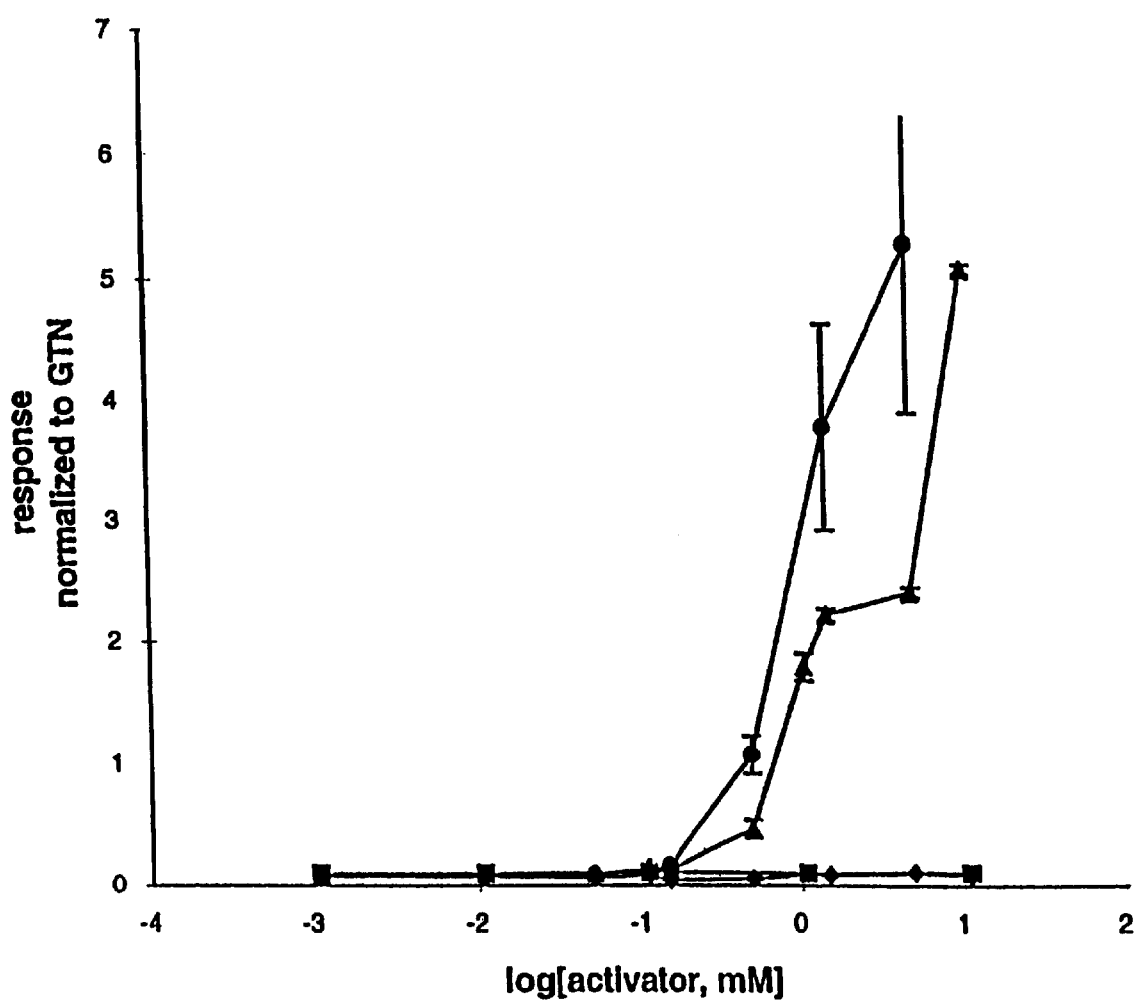
FIG. 5 is a graph showing the effect of IVf neat (diamonds); with added L-cysteine (2 mM, triangles; 5 mM circles); with added dithiothreitol (2 mM, DTT, squares); on soluble GCase activity in rat aorta homogenate, normalized to maximal GTN response. Bars represent the ± standard errors calculated separately for each point.
Figure 6:
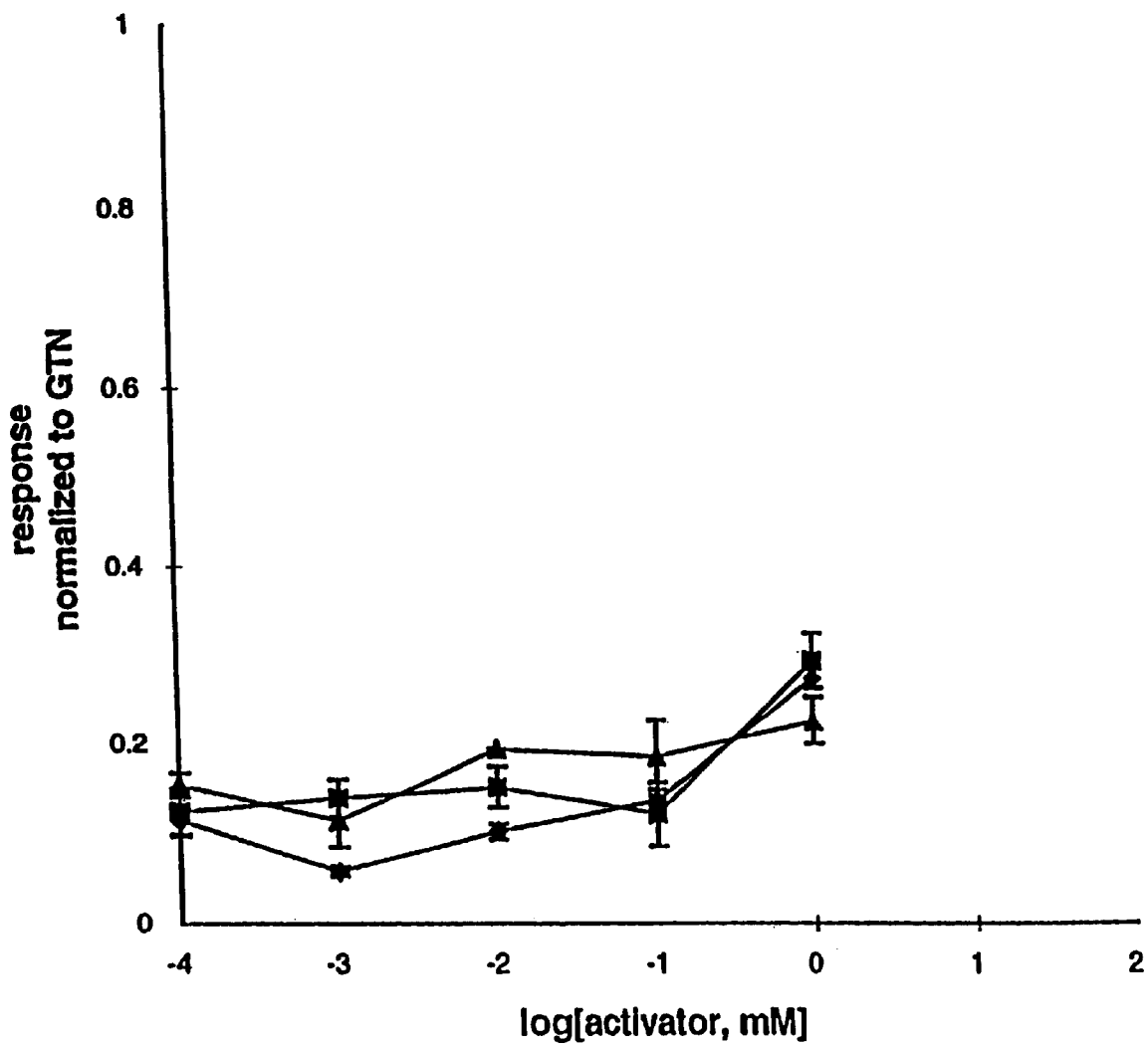
FIG. 6 is a graph showing the effects of IVe neat (diamonds); with added L-cysteine (2 mM, triangles); with added dithiothreitol (2 mM, DTT, squares); on soluble GCase activity in rat aorta homogenate, normalized to maximal GTN response. Bars represent the mean ± standard errors calculated separately for each point.
Figure 7:
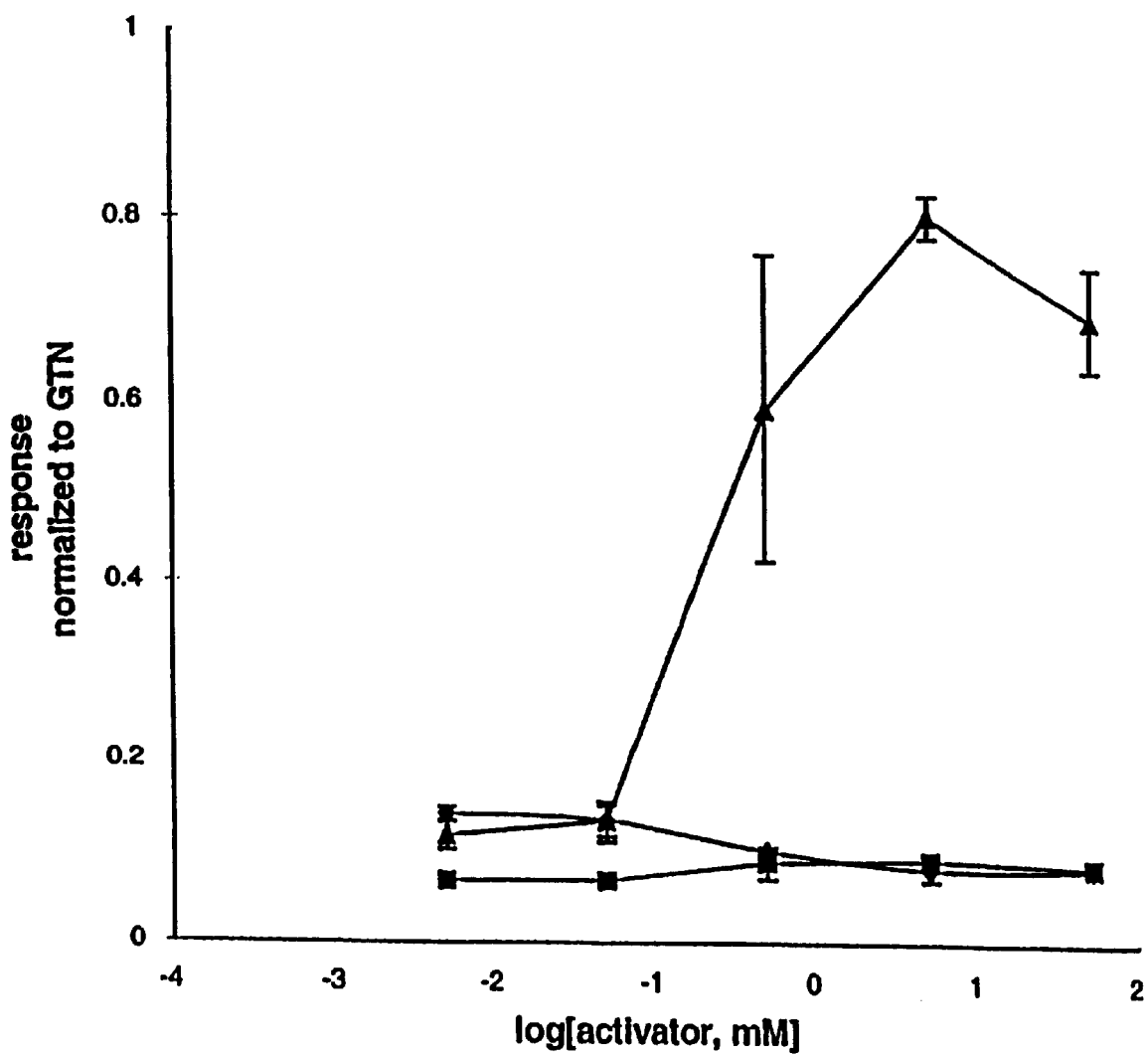
FIG. 7 is a graph showing the effect of IVj neat (diamonds); with added L-cysteine (2 mM, triangles); with added dithiothreitol (2 mM, DTT, squares); on soluble GCase activity in rat aorta homogenate, normalized to maximal GTN response. Bars represent the mean ± standard errors calculated separately for each point.
Figure 8:
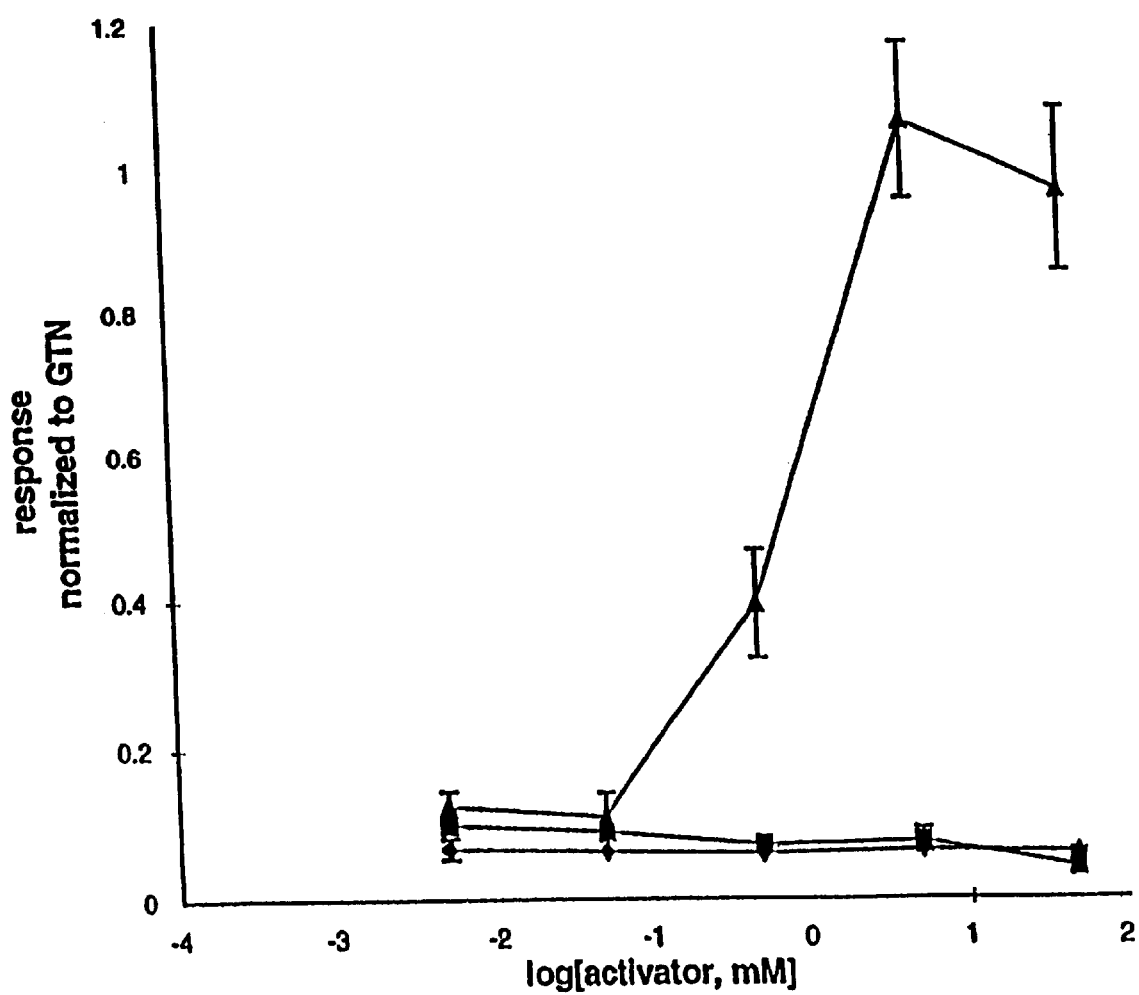
FIG. 8 is a graph showing the effect of IVa neat (diamonds); with added L-cysteine (2 mM, triangles); with added dithiothreitol (2 mM, DTT, squares); on soluble GCase activity in rat aorta homogenate, normalized to maximal GTN response. Bars represent the mean ± standard errors calculated separately for each point.

Activation of soluble guanylyl cyclase (GCase) by nitrates IIIm, IVa, IVb, IVd, IVe, IVf, IVg, IVj, Va, Vb, and GTN was assayed employing partially purified enzyme freshly prepared from the 105,000 g supernatant fraction of rat aorta homogenates, using the radioimmunoassay method described by Bennett et al. (1992), the disclosure of which is incorporated herein by reference. Dose-response curves were obtained for GCase activation by nitrates IVa, IVb, IVd, IVe, IVf, IVg, IVj, and GTN in the presence and absence of cysteine and dithiothretol (DTT; both 2 mM). In all cases, data were normalized to the maximal GTN response carried out in identical GCase preparations. Experimental incubations were performed at 37° C. for 10 min. The data from these curves are summarized in FIGS. 1–8, which give: concentrations of nitrates required to give a response equivalent to the maximal response seen for GTN+cysteine; the maximal response measured for each nitrate, and; where applicable, potency. The GCase assay data show that IVd activates GCase, with a submillimolar $EC_{50}$ in the absence of any added thiol, in contrast to GTN which requires added cysteine (FIGS. 1,2). Compounds IVd and IVg also activate GCase in the presence of DTT in contrast to GTN (FIGS. 2,3). Activation of GCase by IVb was cysteine-dependent and the response was very low ($EC_{50}$>1 mM) (FIG. 4). Activation of GCase by compound IVf was cysteine-dependent and much greater than that achieved by GTN (FIG. 5). Activation of GCase by compound IVe was very low under all conditions tested (FIG. 6). Activation of GCase by compounds IVj and IVa was cysteine-dependent and approximately equivalent to GTN (FIGS. 7,8). Relative to GTN itself, a wide range of potencies was observed for the nitrate esters of the invention. No activation of GCase by glycerol mononitrates was observed in this assay at the concentrations of nitrate employed.

Figure 9:
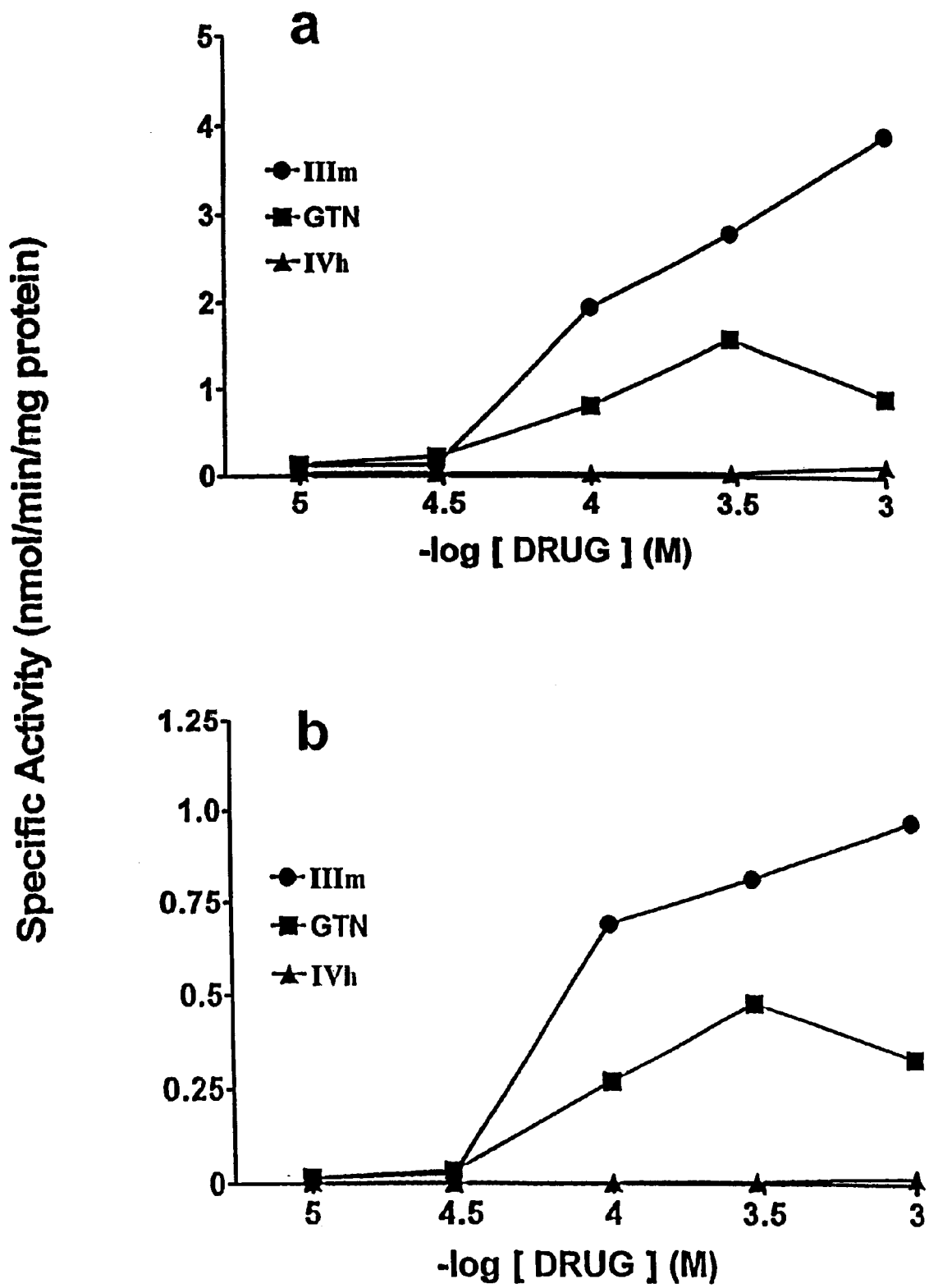
FIG. 9 is a graph showing a comparison of GTN (squares), IIIm (circles) and IVh (triangles) with added L-cysteine (1 mM) on soluble GCase activity in rat aorta homogenate (a), and rat hippocampus homogenate (b). Data points represent the mean of duplicate determinations carried out in identical GCase preparations.
Figure 10:
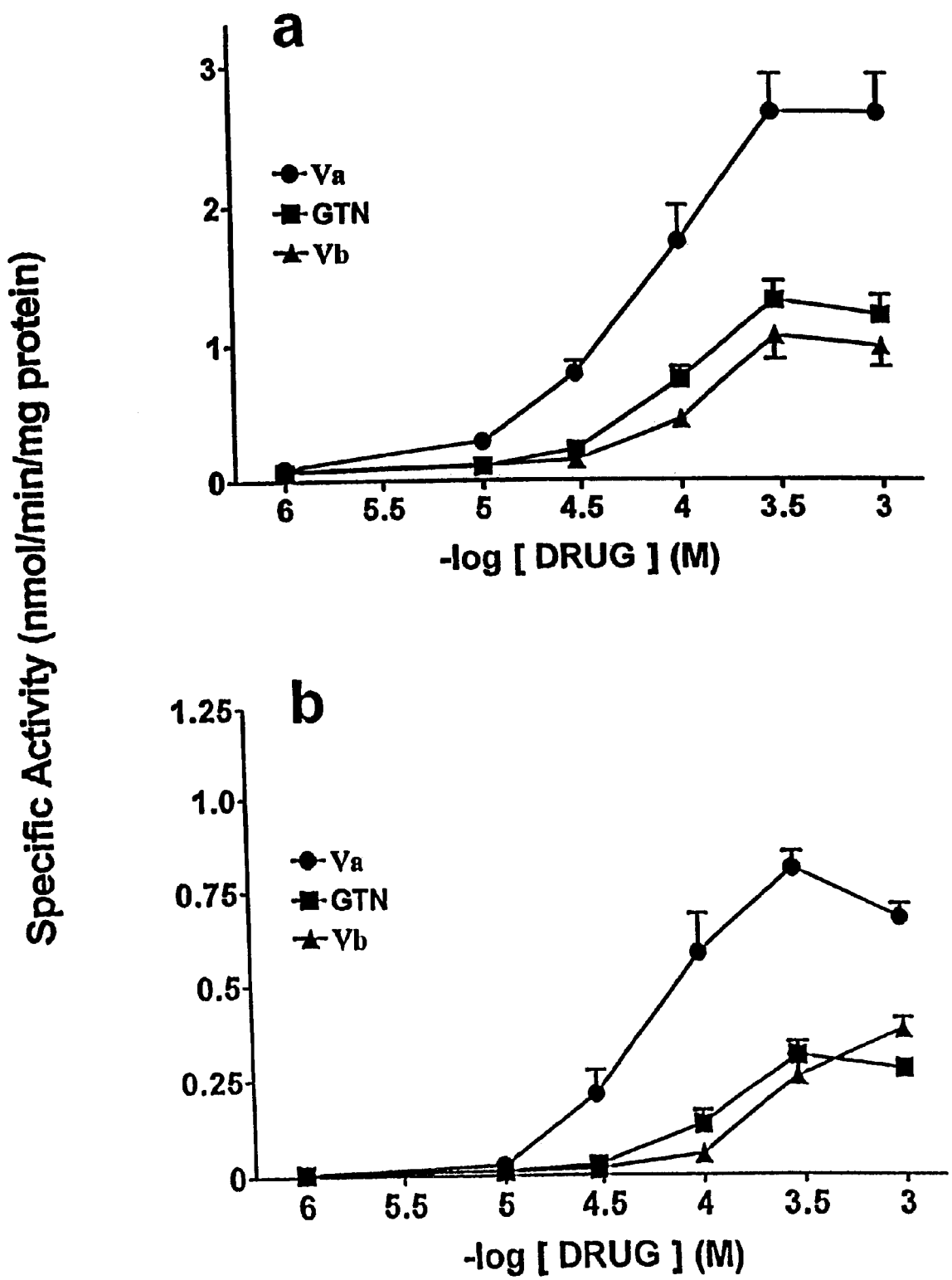
FIG. 10 is a graph showing a comparison of GTN (squares), Va (circles) and Vb (triangles) with added L-cysteine(1 mM) on soluble GCase activity in rat aorta homogenate homogenate (a), and rat hippocampus homogenate (b). Data points represent the mean ± standard errors calculated separately for each point (n=8–11).

To test for potential differences in GCase activation by nitrates, the effects of IIIm, IVh, Va, Vb, and GTN were assayed in brain and vascular tissue. IVh had no effect on GCase activity in either rat aorta or rat hippocampus (FIG. 9). IIIm had greater efficacy to stimulate GCase activity compared to GTN in both rat aorta and rat hippocampus (FIG. 9). Vb was found to be equivalent to GTN in efficacy and potency for activation of GCase in both rat aorta and rat hippocampus (FIG. 10). Va was found to have greater efficacy, but equal potency, to GTN in rat aorta (FIG. 10a). In contrast, Va had greater efficacy and greater potency to stimulate GCase in rat hippocampus (FIG. 10b). These data illustrate that nitrates have differential effects on GCase activation that are dependent on both structure of the compound and the tissue assayed for GCase activity, supporting the notion that neuroprotective and cardiovascular effects of nitrates are separable.

Example 2

Characterization of cyclic GMP accumulation

Figure 11:
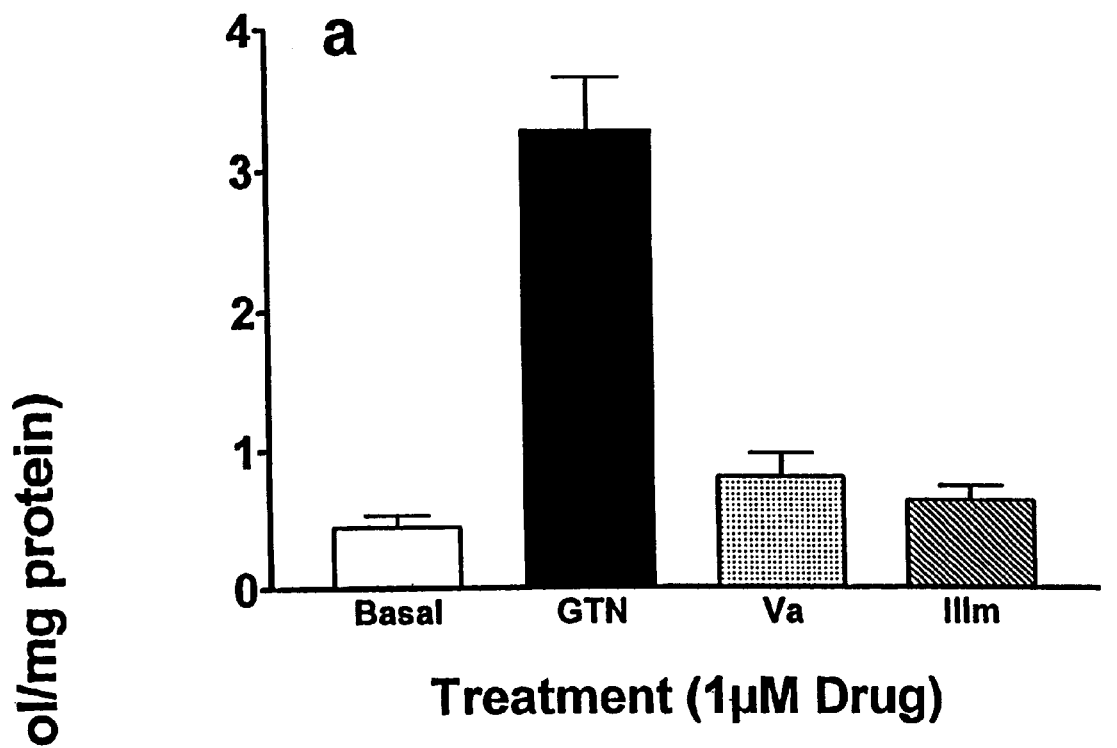
FIG. 11 is a graph showing a comparison of cyclic GMP accumulation in isolated rat aorta induced by diluent (Basal, open bar), GTN (filled bar), Va (stippled bar), or IIIm (hatched bar). Segments of rat aorta were exposed to diluent, 1 $\mu$M drug (a), or 10 $\mu$M drug (b) for 1 min. and cyclic GMP content determined by radioimmunoassay. Data are the mean ± standard errors (a, n=8; b, n=5).
Figure 11:
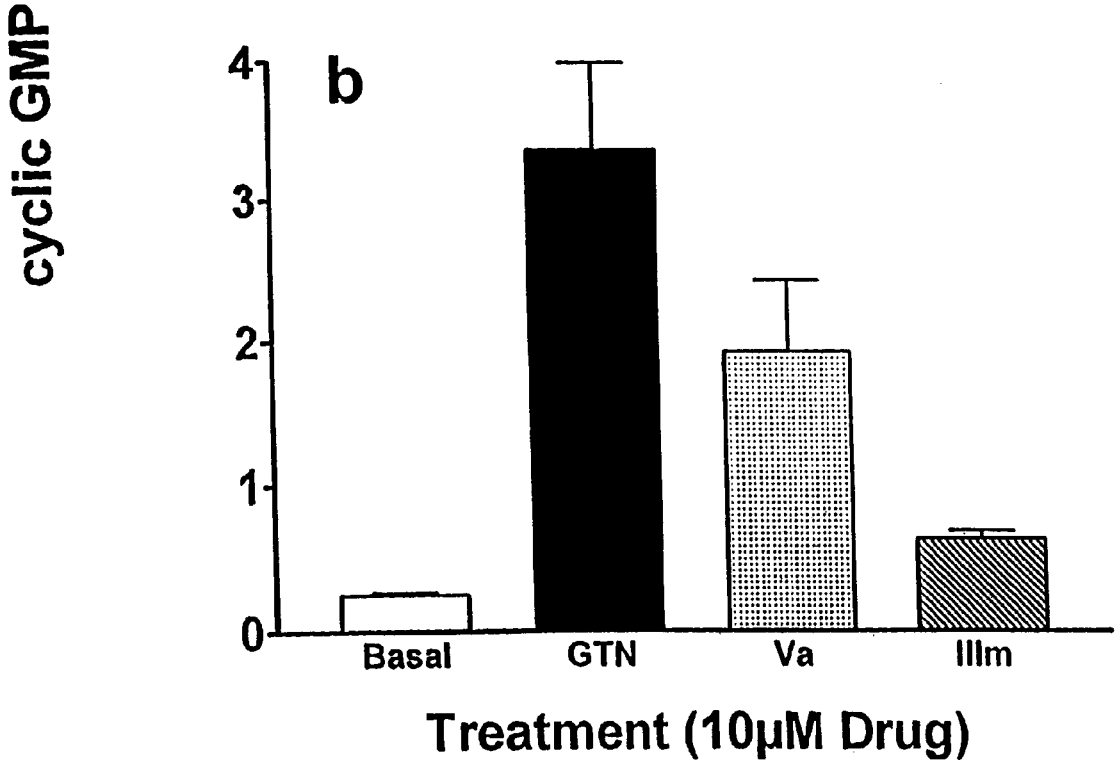
Figure 12:
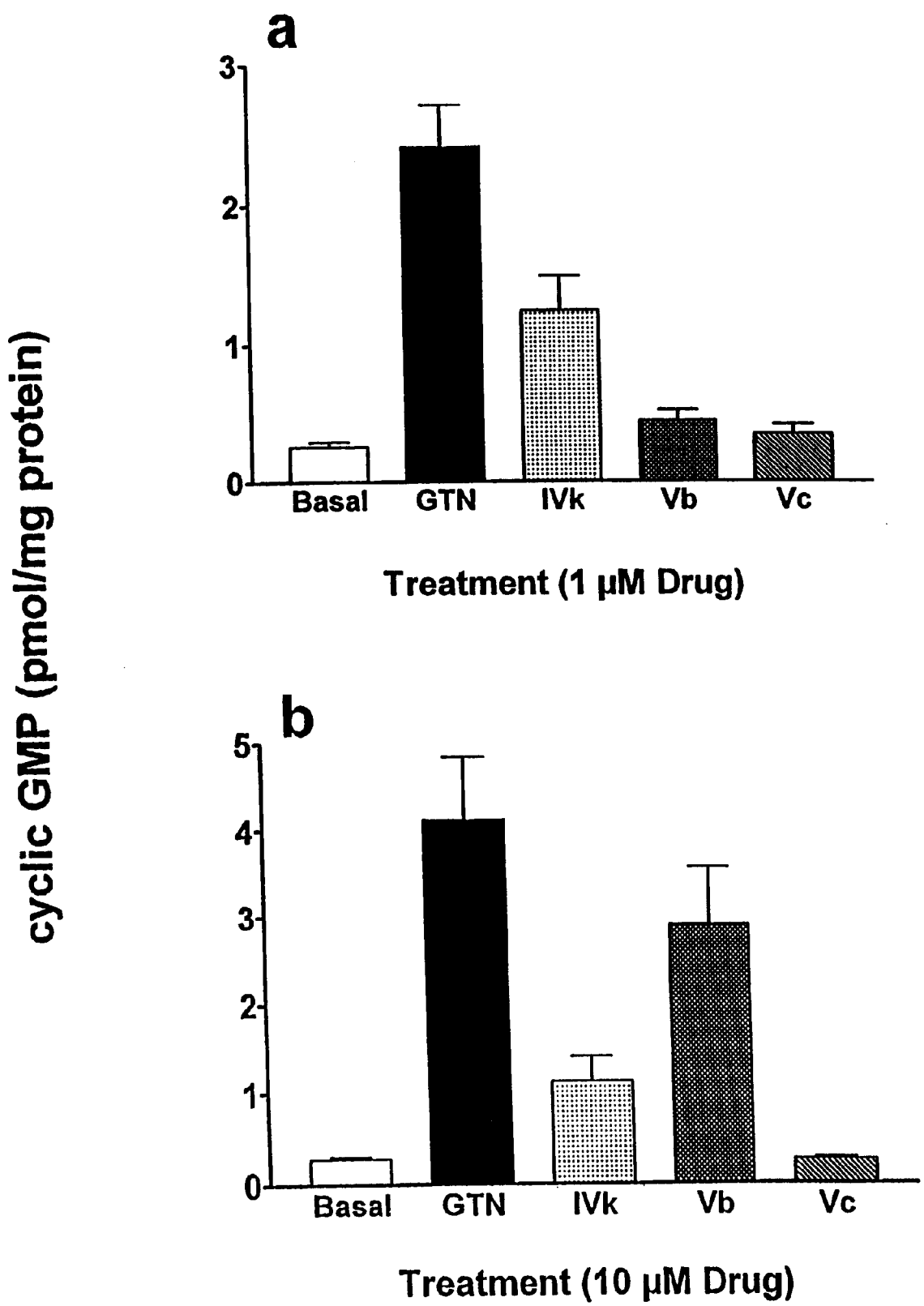
FIG. 12 is a graph showing a comparison of cyclic GMP accumulation in isolated rat aorta induced by diluent (Basal, open bar), GTN (filled bar), IVk (stippled bar), Vb (cross-hatched bar), or Vc (hatched bar). Segments of rat aorta were exposed to diluent, 1 $\mu$M drug (a), or 10 $\mu$M drug (b) for 1 min and cyclic GMP content determined by radioimmunoassay. Data are the mean ± standard errors (a, n=5; b, n=4).

In order to extend the GCase data further, the effects of nitrates Va, IIIm, Vb, Vc, and IVk on cyclic GMP accumulation in intact isolated rat aorta were examined (FIGS. 11,12). Thoracic aortic strips were prepared from male Sprague-Dawley rats (Charles-River, Canada) as described in McGuire et al. (1994) and Stewart et al. (1989), both incorporated herein by reference. Tissues were contracted submaximally with phenylephrine (0.1 $\mu$M) and exposed to various concentrations of drug for 1 min. Cyclic GMP accumulation was determined using the radioimmunoassay method described in Bennett et al. (1992). At concentrations of 1 $\mu$M and 10 $\mu$M, GTN and IVk significantly increased cGMP accumulation (FIGS. 11,12). At a concentration of 1 $\mu$M, Va, IIIm, Vb, and Vc did not significantly increase cyclic GMP accumulation (FIGS. 11a, 12a). At a concentration of 10 $\mu$M, Va, Vb, and IVk significantly increased cyclic GMP accumulation, whereas IIIm and Vc did not (FIGS. 11b, 12b).

Figure 13:
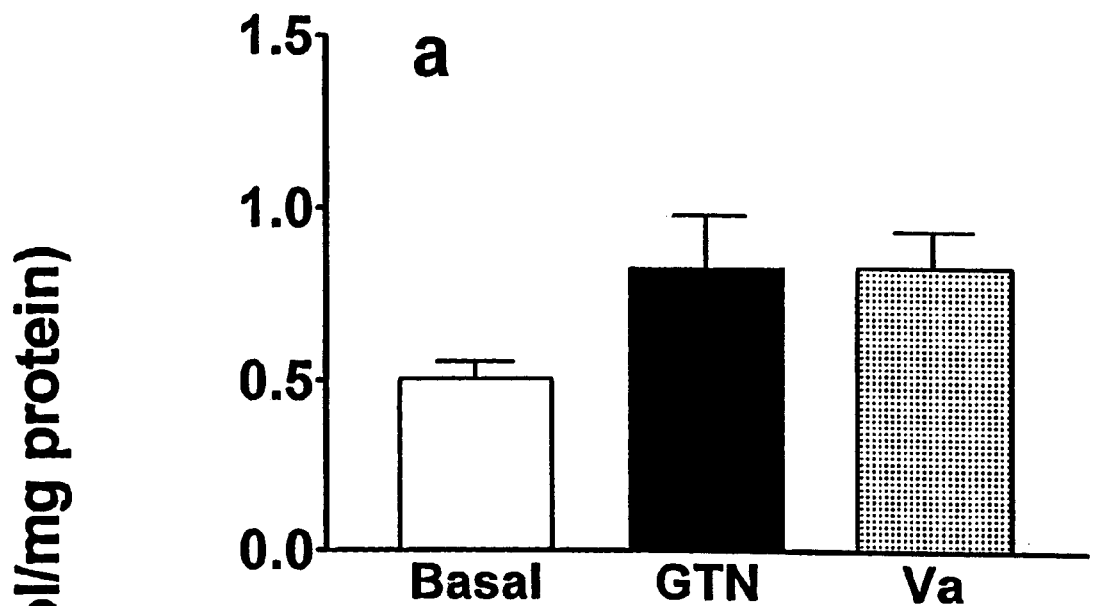
FIG. 13 is a graph showing cyclic GMP accumulation in rat hippocampal slices induced by diluent (Basal, open bar), GTN (filled bar), and Va (stippled bar). Sections of rat hippocampus (400 $\mu$m) were prepared and exposed to diluent, 10 $\mu$M drug (a) or 100 $\mu$M drug (b) for 3 min and cyclic GMP content determined by radioimmunoassay. Data are the mean ± standard errors (a, n=4; b, n=5).
Figure 13:
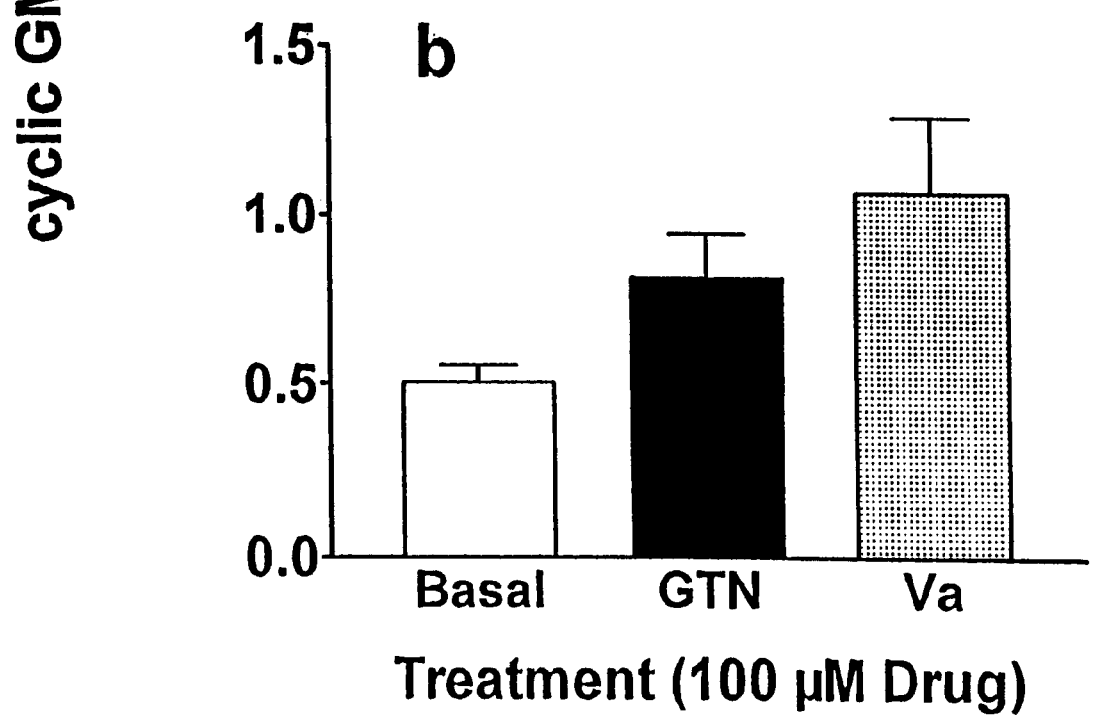

Sections of rat hippocampus (400 $\mu$m) were prepared and incubated in oxygenated Krebs solution at 37° C. After a 60-min equilibration period, the brain slices were stimulated with different concentrations of Va or GTN for 3-min. Cyclic GMP accumulation was determined as described above for aortic strips. FIG. 13 shows that Va causes a concentration-dependent increase in the tissue levels of cGMP in rat hippocampal brain slices in vitro and that, at high concentration (100 $\mu$M), Va is more effective than GTN in elevating cGMP levels in hippocampal brain slices in vitro. These data are in very good agreement with the differential effects of Va and GTN on hippocampal GCase activity shown in FIG. 10b.

Example 3

Characterization of relaxation of isolated blood vessels

Figure 14:
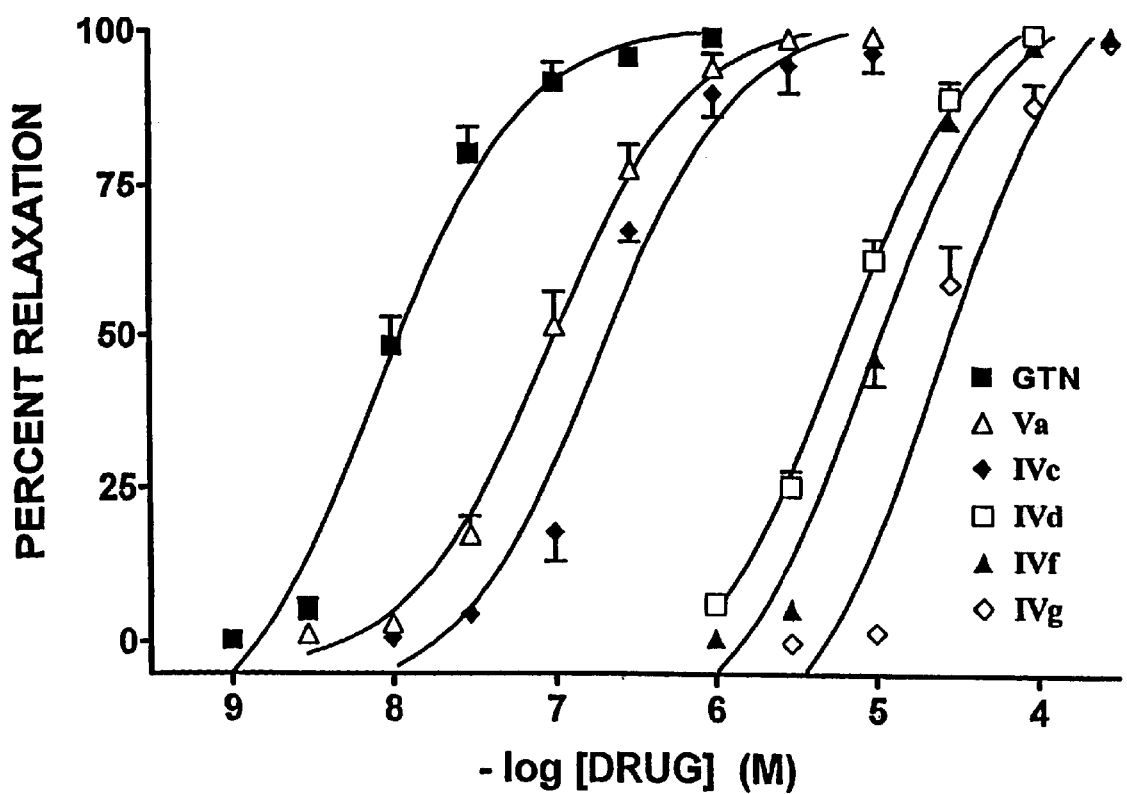
FIG. 14 is a graph showing a comparison of relaxation of isolated rat aorta induced by GTN (squares), Va (open triangles), compound IVc (diamonds), compound IVd (open squares), compound IVf (triangles), and compound IVg (open diamonds). Data points represent the mean ± standard errors (n=5–8).
Figure 15:
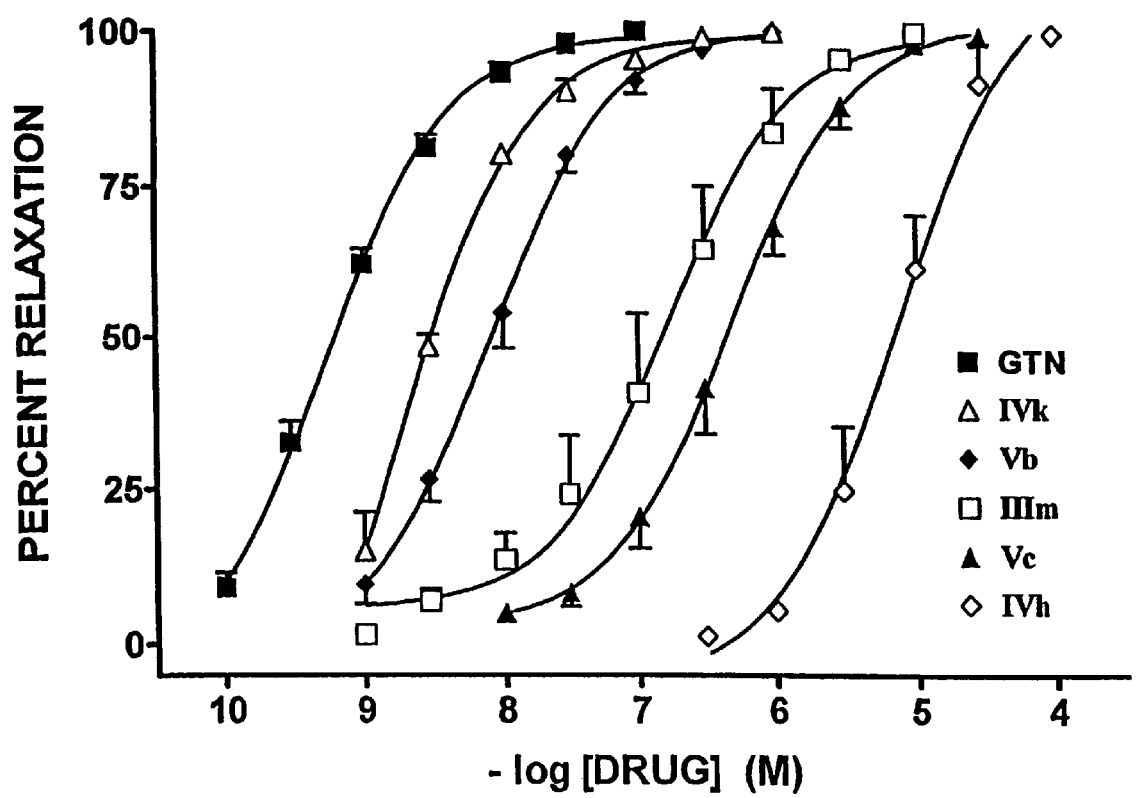
FIG. 15 is a graph showing a comparison of relaxation of isolated rat aorta induced by GTN (squares), IVk (open triangles), Vb (diamonds), IIIm (open squares), Vc (triangles), and IVh (open diamonds). Data points represent the mean±standard errors (N=3–8).
Figure 16:
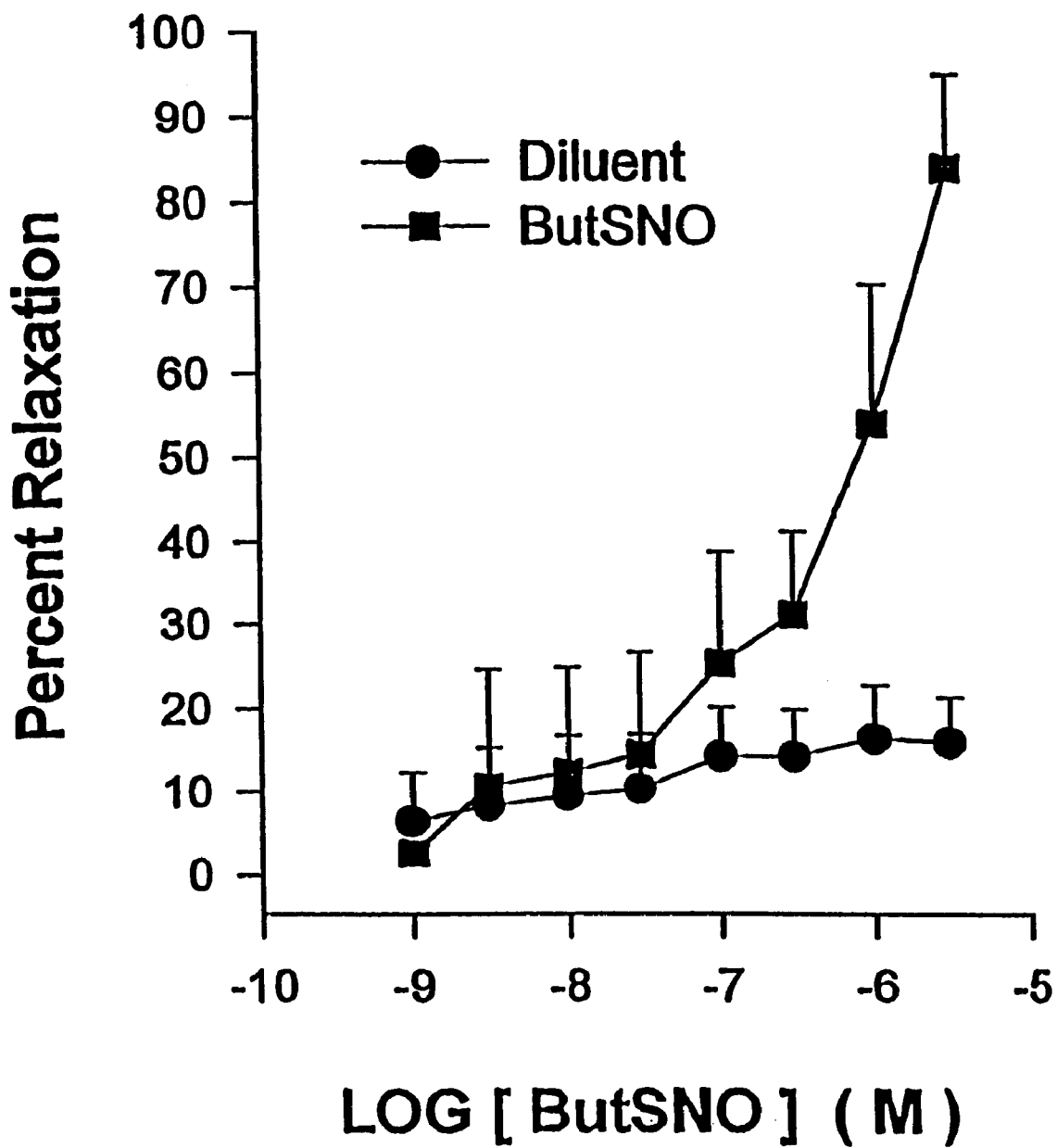
FIG. 16 is a graph showing relaxation induced by t-Bu nitrosothiol in isolated rat aorta. Data points represent the mean±standard deviation (n=3).
Figure 17:
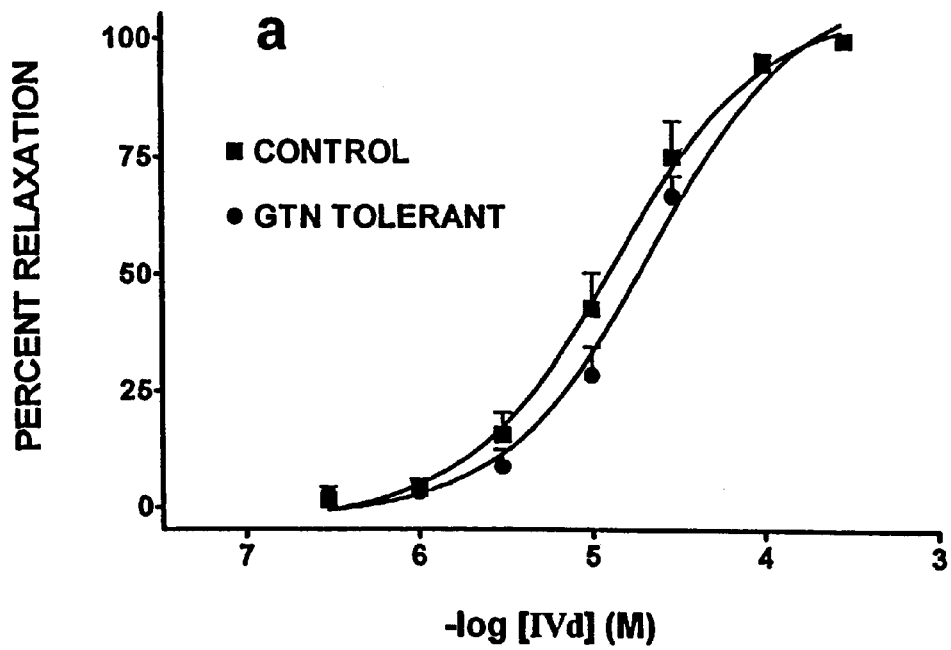
FIG. 17 is a graph showing relaxation induced by compound Ivd (a) and IVc (b) in untreated (squares) and GTN-tolerant (triangles) isolated rat aorta. Aortae were made tolerant by treatment with 0.5 mM GTN for 30 min. Data points represent the mean±standard deviation (N=3–6).
Figure 17:
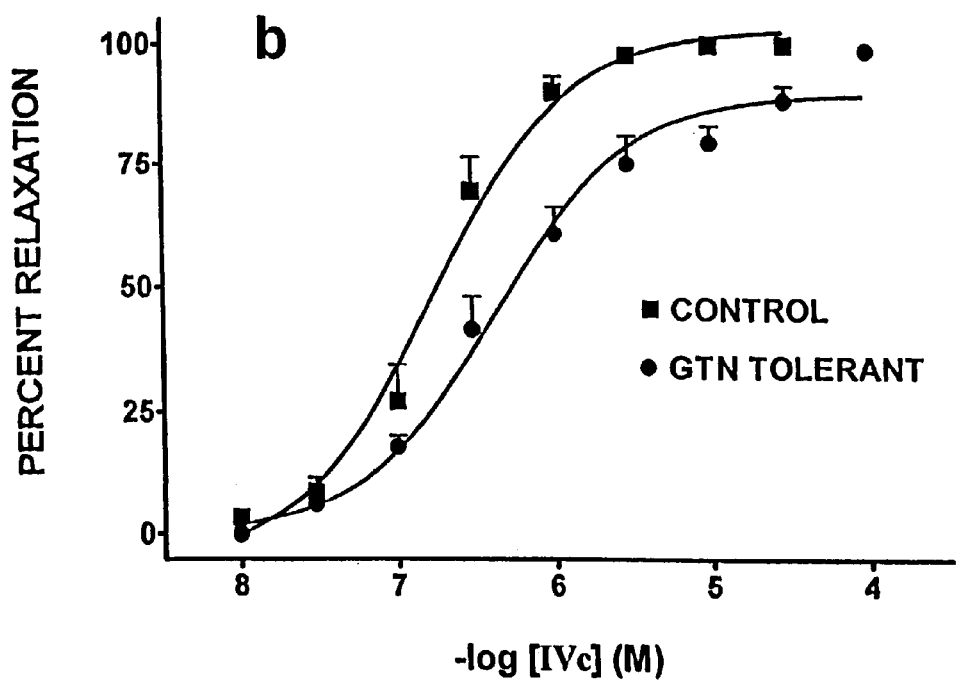

In order to extend the GCase data, the relaxing effects of nitrates IIIm, IVc, IVd, IVf, IVg, IVh, IVk, Va, Vb, and Vc on rat aortic tissue were examined. Thoracic aortic strips were prepared from male Sprague-Dawley rats (Charles-River, Canada) as described in McGuire et al. (1994), and Stewart et al. (1989). Tissues were contracted submaximally with phenylephrine (0.1 $\mu$M) and exposed to various concentrations of nitrovasodilator to obtain concentration-response curves. In this intact tissue assay, all of the nitrates were observed to cause relaxation of the tissue with a maximal relaxant response equal to that obtained with GTN. However, the compounds differed in potency with $EC_{50}$ (effective concentration for 50% of the subjects) values of 7.87 nM, 94.3 nM, 6.59 $\mu$M, 25.2 $\mu$M, 11.0 $\mu$M, 0.203 $\mu$M, for GTN and compounds Va, IVd, IVg, IVf, and IVc, respectively (FIG. 14). In another series of experiments, the $EC_{50}$ values for relaxation were 0.61 nM, 3.19 nM, 8.40 nM, 0.153 $\mu$M, 0.437 $\mu$M and 6.89 $\mu$M for GTN, IVk, Vb, IIIm, Vc, and IVh, respectively (FIG. 15). The $EC_{50}$ value for a nitrosothiol (tert-butyl nitrosothiol, FIG. 16) was 11.2 $\mu$M. Compounds IVd and IVc were tested for their ability to cause vascular relaxation in tissues that had been made tolerant to the relaxant effect of GTN. GTN tolerance was induced by incubating tissues with high concentrations of GTN (0.5 mM GTN for 30 min). Under these conditions, the maximal relaxant effects of IVd (FIG. 17a) and IVc (FIG. 17b) were not significantly different from their effects for untreated tissue. The $EC_{50}$ for relaxation was increased approximately threefold, but the difference was not statistically significant.

Example 4

Characterization of blood pressure changes in the whole animal

Figure 18:
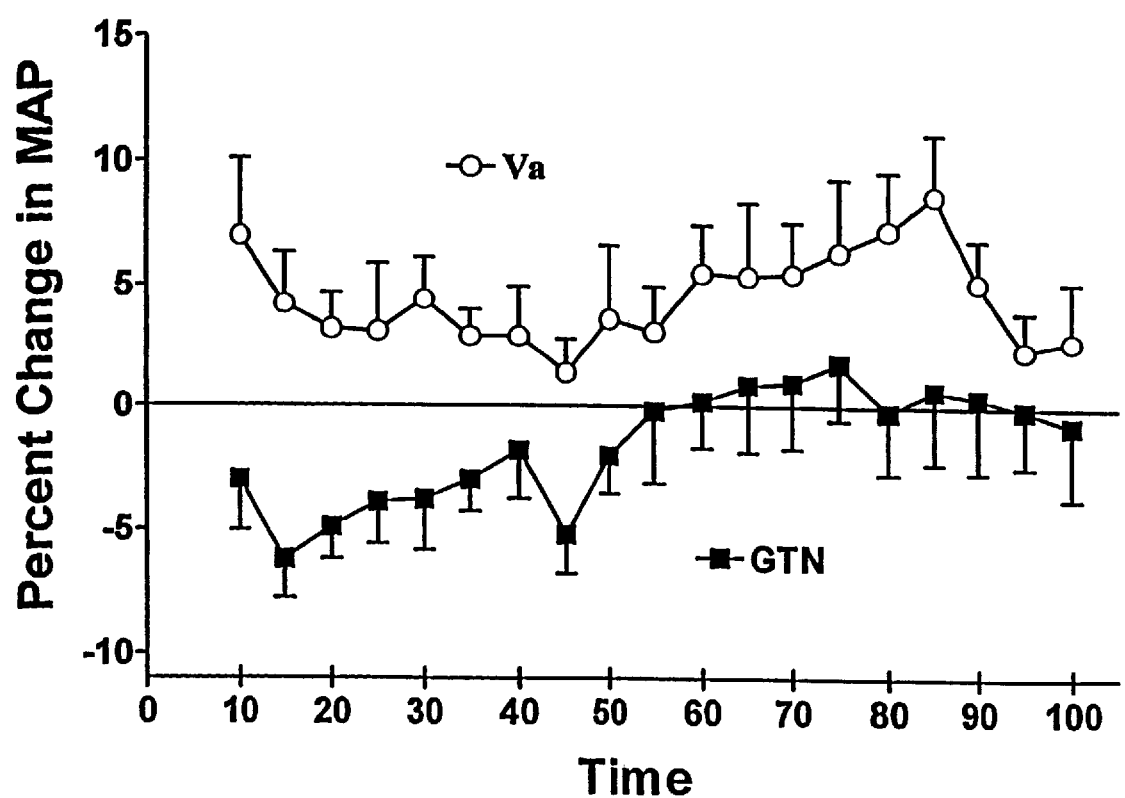
FIG. 18 is a graph showing a comparison of the percent change in mean arterial pressure in conscious unrestrained rats after subcutaneous administration of 400 μmol/kg GTN (squares) or Va (open circles). Data points represent the mean±standard errors (n=6).
Figure 19:
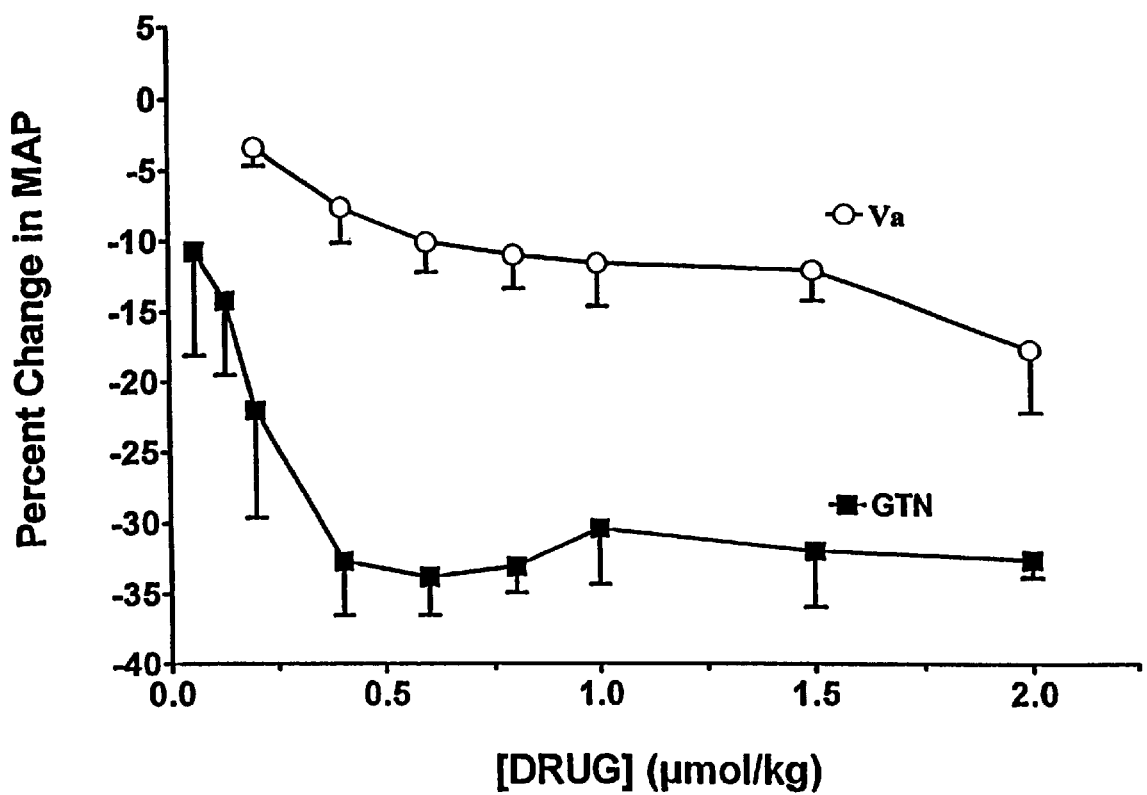
FIG. 19 is a graph showing a comparison of the percent change in mean arterial pressure in Inactin anaesthetized rats after intravenous bolus injection of GTN (squares) or Va (open circles). Data points represent the mean±standard errors (n=4).

To test for differential effects of nitrates on blood pressure responses, Va and GTN were injected into rats in which the abdominal aorta was cannulated for blood pressure recording. In the first experiment, Va and GTN were injected subcutaneously at a dose of 400 $\mu$mol/kg body weight into conscious, freely moving animals. GTN caused a small and transient decrease in blood pressure in these animals, whereas Va had no discernable effect on arterial blood pressure (FIG. 18). Va and GTN were subsequently tested in anesthetized rats in which the abdominal vena cava was also cannulated to allow for bolus intravenous injection of drugs. In this preparation, GTN caused a substantial and dose-dependent decrease in arterial blood pressure. In contrast, Va at equal doses had very modest effects on blood pressure at doses lower than 2 $\mu$mol/kg body weight (FIG. 19). These data are in very good agreement with the results obtained for these two agents using the isolated blood vessel preparation.

Figure 20:
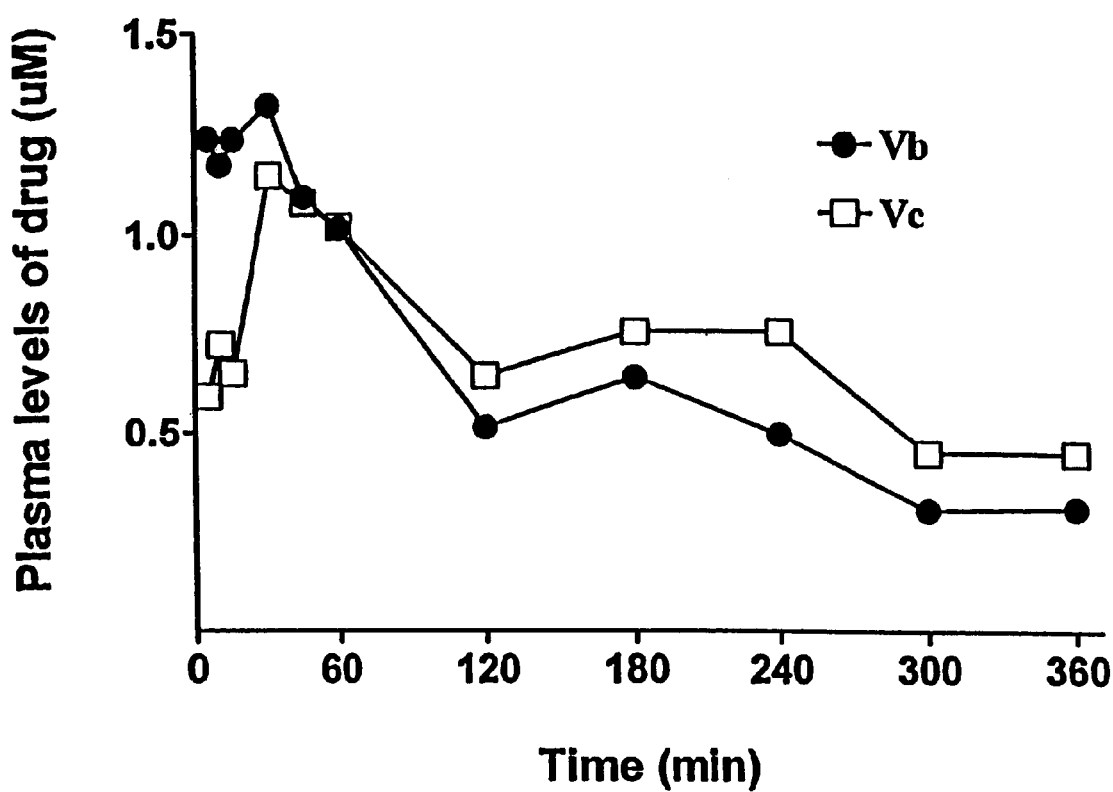
FIG. 20 is a graph showing plasma levels (μM) of Vb (circles) and its mononitrate metabolite Vc (open squares) after subcutaneous administration of 200 μmol/kg Vb in conscious unrestrained rats. Data points represent the mean of two experiments.

The plasma levels of nitrates Vb and Vc (the denitrated metabolite of Vb) were measured to gain insight into the handling of these molecules in the body. Cannulas were placed in the abdominal aorta for blood sampling. After a two-day recovery period, a single subcutaneous dose of Vb (200 $\mu$mol/kg) was administered and blood samples collected over a period of six hours. Samples were centrifuged, the plasma collected, and the concentrations of Vb and Vc determined by gas-liquid chromatography by the method of McDonald and Bennett (1990). The data obtained for Vb and Vc indicate that nitrates achieve maximal plasma levels within 30 minutes after subcutaneous injection, and therafter decline at a steady rate (FIG. 20). These data suggest that nitrates have excellent bioavailability after subcutaneous injection.

Example 5

Characterization of neuroprotection in brain slices

Figure 21:
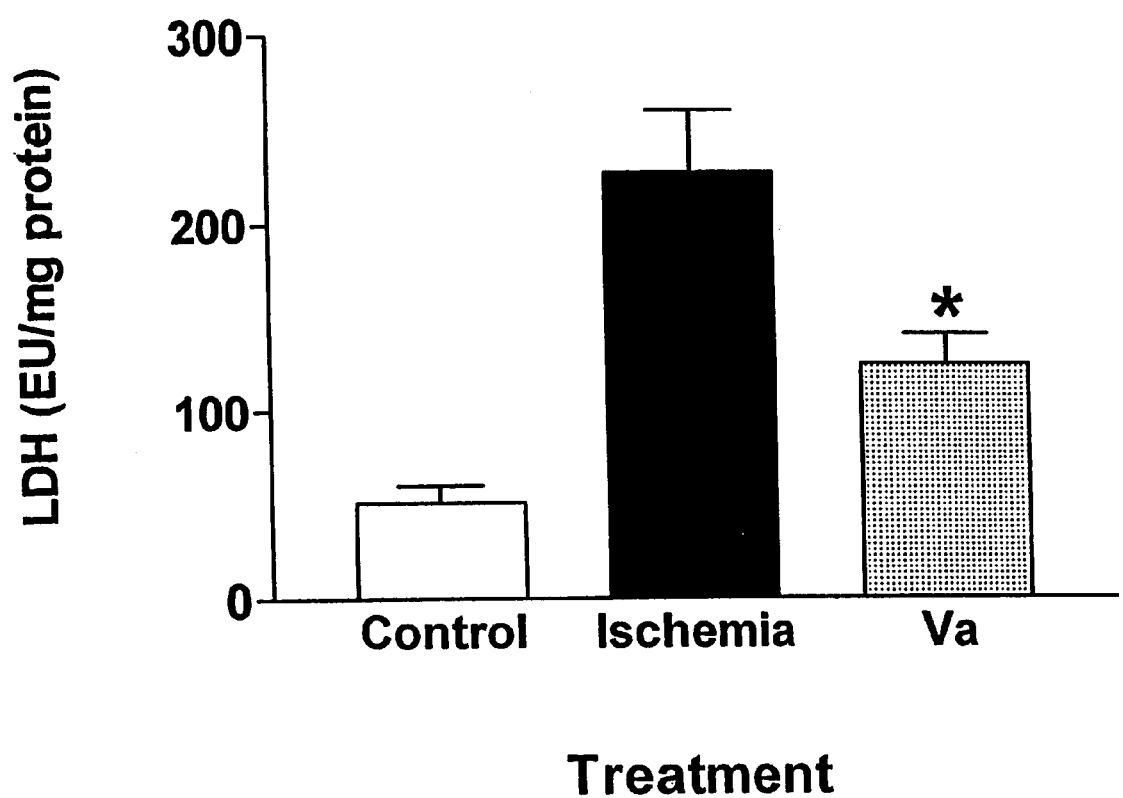
FIG. 21 is a graph showing the effect of compound Va on lactate dehydrogenase (LDH) release from rat hippocampal slices after a 30-min period of in vitro ischemia. Data are the mean±standard errors (n=8). *, P<0.05 compared to ischemia.
Figure 22:
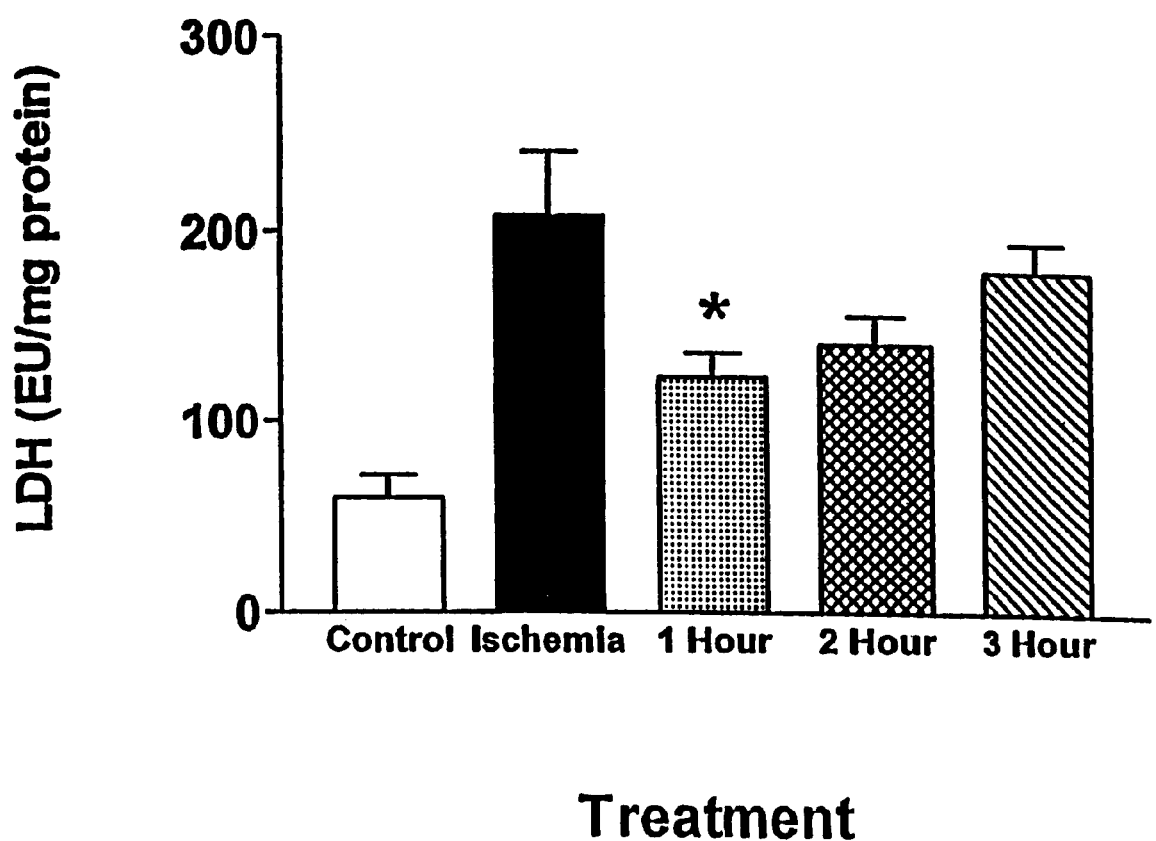
FIG. 22 is a graph showing the effect of delayed administration of Va on lactate dehydrogenase (LDH) release from rat hippocampal slices after a 30-min period of in vitro ischemia. Data are the mean±standard errors (n=6). *, P<0.05 compared to ischemia.

In order to test for potential neuroprotective properties, the effects of Va were tested in an in vitro model of cerebral ischemia. Rat hippocampal slices were subjected to 30 minutes of ischemia by incubation in a buffered salt solution lacking glucose and oxygen. Sections of rat hippocampus (400 $\mu$m) were prepared and incubated in oxygenated Krebs solution at 37° C. Slices were then either untreated or subjected to a 30-minute period of ischemia by incubation in Krebs solution lacking oxygen and glucose. Slices were then incubated for a further 4 hours in oxygenated Krebs solution in the presence of drug vehicle or 200 μM Va. At the end of the 4-hr re-oxygenation period, release of the cytosolic enzyme lactate dehydrogenase (LDH) from the tissue was used an index of neuronal cell injury. Some hippocampal slices were treated with Va (200 μM) after the 30-minute period of ischemia. FIG. 21 shows that Va significantly reduced the release of LDH from ischemic brain slices when administered immediately after the period of ischemia. FIG. 22 shows that Va was still effective at protecting ischemic brain slices in vitro when drug exposure was delayed for up to 1 hour after re-oxygenation of the tissue.

Figure 23:
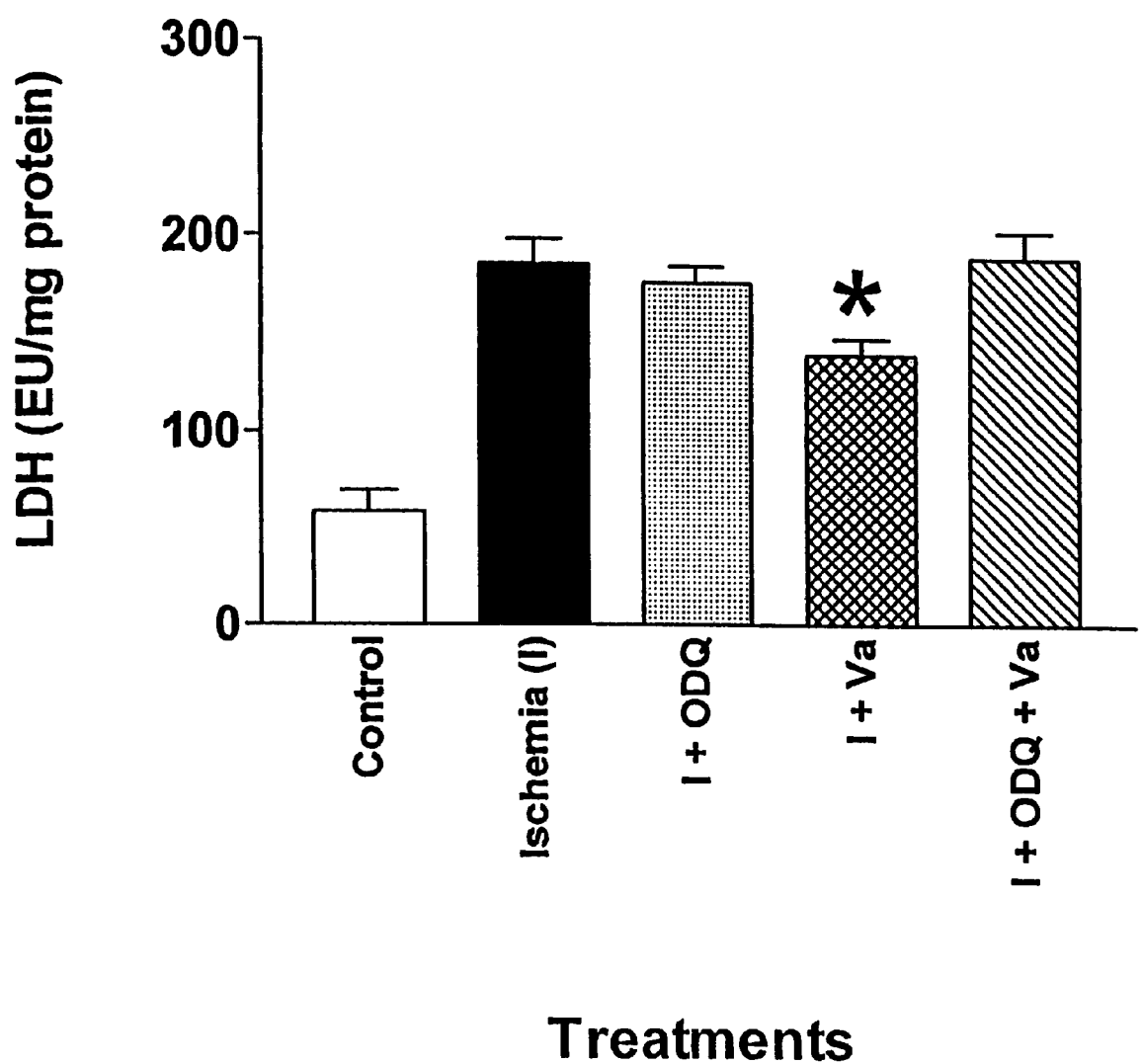
FIG. 23 is a graph showing the effect of blocking guanylyl cyclase with ODQ on the neuroprotective properties of Va in rat hippocampal slices subjected to a 30-min period of in vitro ischemia. Data are the mean±standard errors (n=4).

To test the mechanism of this neuroprotection, rat hippocampal brain slices made ischemic for 30 minutes in vitro were exposed to the guanylyl cyclase inhibitor ODQ 5-min prior to administration of 200 μM Va. The concentration of ODQ used was known to completely block the production of cGMP induced by Va. Blockade of guanylyl cyclase by ODQ completely eliminated the neuroprotective effect of Va in ischemic rat hippocampal slices, showing that elevations in cGMP levels are directly related to the neuroprotective properties of Va in vitro (FIG. 23).

Example 6

Characterization of neuroprotection in the whole animal

Figure 24:
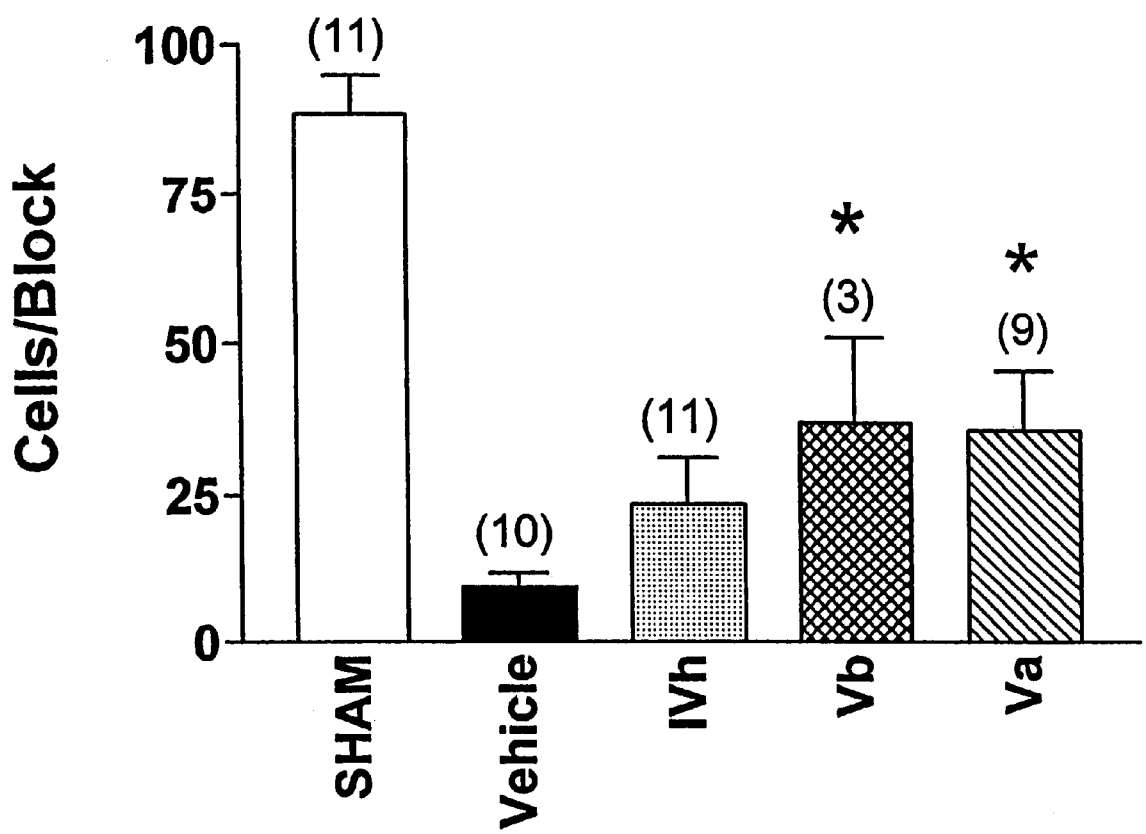
FIG. 24 is a graph showing viable neurons in the CA1 region of the gerbil hippocampus after global cerebral ischemia. Data are the mean±standard error for the number of animals in parentheses. *, P<0.05 compared to vehicle control.

To test the efficacy of nitrates in animal models of cerebral ischemia, two different approaches were taken. In the first, Mongolian gerbils were subjected to 5 minutes of global forebrain ischemia by occlusion of the common carotid arteries under halothane anesthesia. This period of ischemia produces a selective neuronal cell death in the CA1 region of the hippocampus that develops over several days. Surgical procedure, and control of brain and body temperature during the occlusion, were as described in Nurse and Corbett (1996), incorpated herein by reference. Animals were given two subcutaneous injections of drug vehicle, or 400 μmol/kg IVh, Vb or Va at 5-min and 90-min after the occlusion. Sham-treated animals had the carotid arteries exposed but not occluded. Seven days later, the brains were fixed by transcardiac perfusion with 4% paraformaldehyde, dissected out, embedded in paraffin, and 5 μm sections were cut and stained with cresyl violet. Viable neurons in 100 square μm blocks of the CA1 region were counted to obtain an index of neuronal cell damage. The results obtained with nitrates IVh, Vb, and Va are shown in FIG. 24. Both Va and Vb produced a statistically significant neuroprotection against 5 minutes of global forebrain ischemia in the gerbil.

Figure 25:
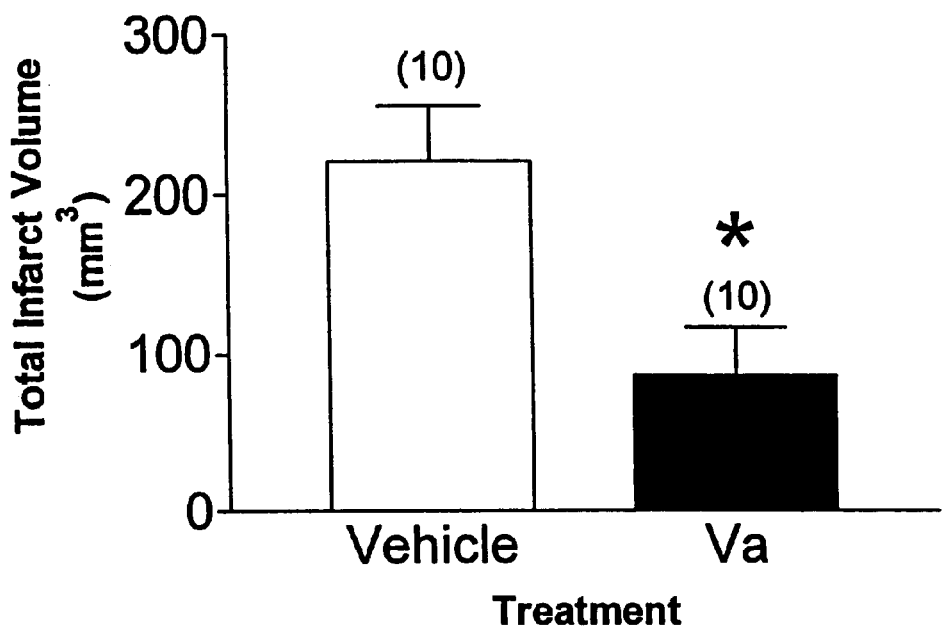
FIG. 25 is a graph showing the total and cerebral cortical infarct volume of rat brain after a 2-hour period of focal cerebral ischemia. Data are the mean±standard errors (n=10).
Figure 25:
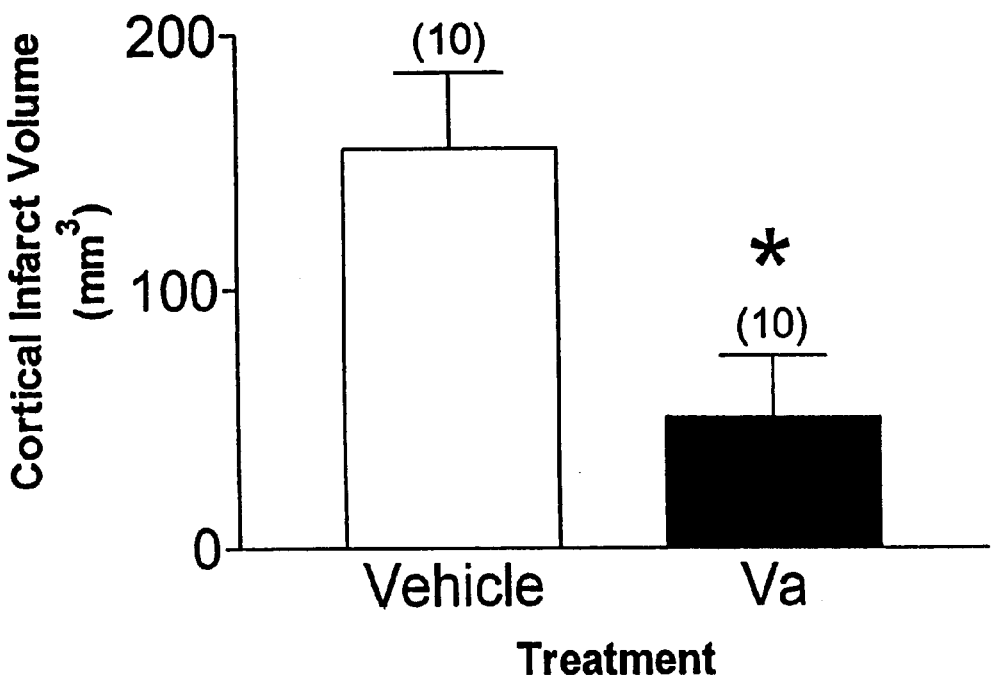

The second animal model tested was transient focal cerebral ischemia in the rat induced by occlusion of the middle cerebral artery. Under halothane anesthesia, a filament was advanced into the right internal carotid artery until the origin of the right middle cerebral artery was occluded. The filament was secured, the animal allowed to regain consciousness, and two hours later the filament was removed under halothane anesthesia. Animals were given five subcutaneous doses of drug vehicle or 200 μmol/kg Va at 2, 3, 4, 6, and 8 hr post-occlusion. At 24 hr post-occlusion the animals were sacrificed, the brain removed, cut into 2-mm coronal sections and stained for viable tissue with 2,3,5-triphenyltetrazolium. Infarct volume of whole brain and cerebral cortex was quantitated by computer-assisted image analysis. A 2-hour episode of cerebral ischemia followed by recirculation produces a large infarct in the cerebral cortex and subcortical structures on the affected side. The volumes of the total and cerebral cortical infarct in the rat brain were very similar to those reported by other groups using the same procedure (e.g., Sydserff et al., 1995; Morikawa et al., 1998). FIG. 25 shows the results obtained with nitrate Va in this model. A series of subcutaneous injections of Va at a dose of 200 μmol/kg body weight at 2, 3, 4, 6, and 8 hours after the onset of cerebral ischemia resulted in a statistically significant neuroprotection when assayed 24 hours after ischemia. Collectively, these data indicate that delayed administration of Va is neuroprotective in two different animal models of cerebral ischemia.

Figure 26:
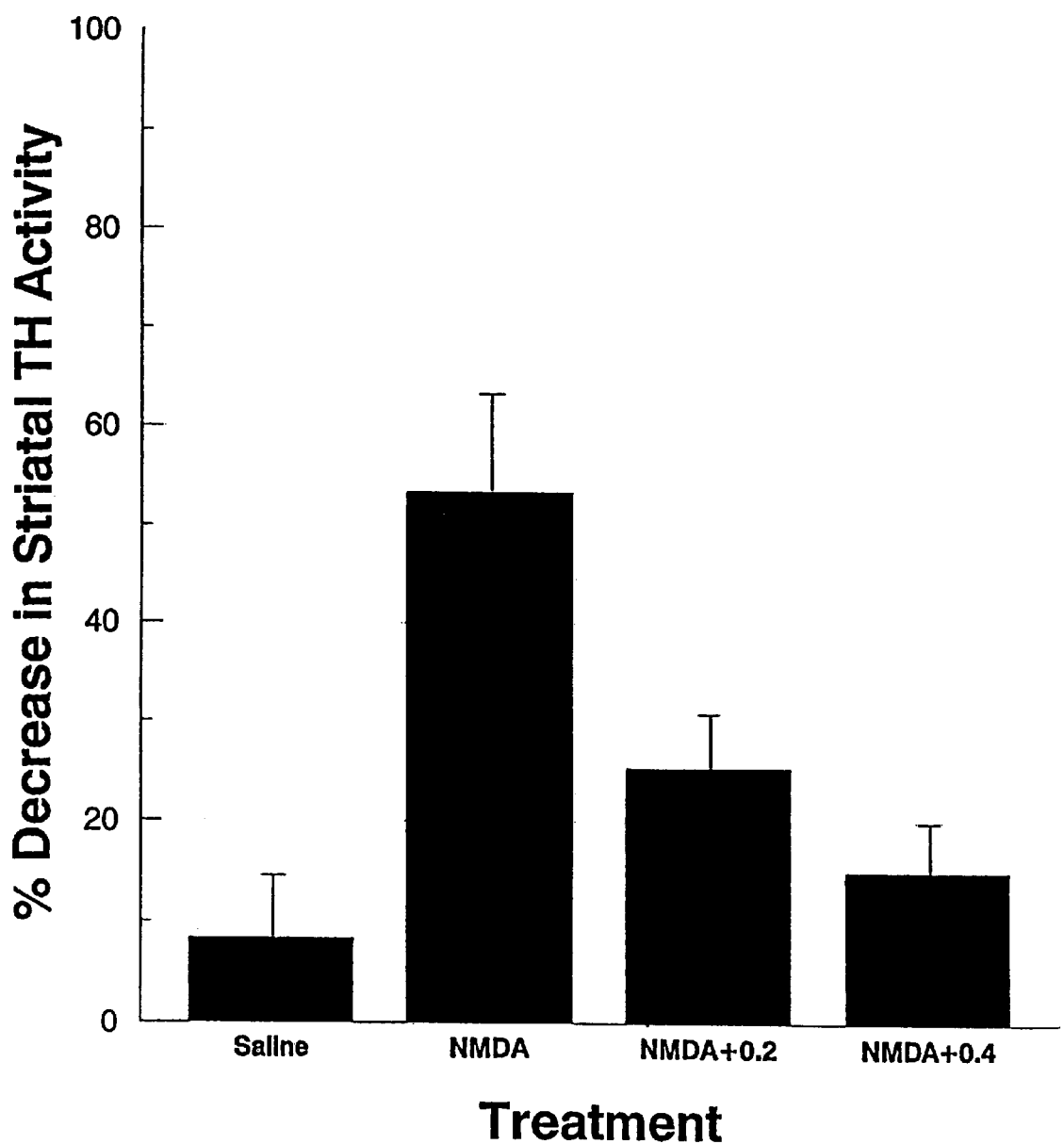
FIG. 26 is a graph showing the effect of GTN (0.2. or 0.4 mg/hr by subcutaneous patch) on NMDA-induced loss of striatal tyrosine hydroxylase (TH) activity in the rat.
Figure 27:
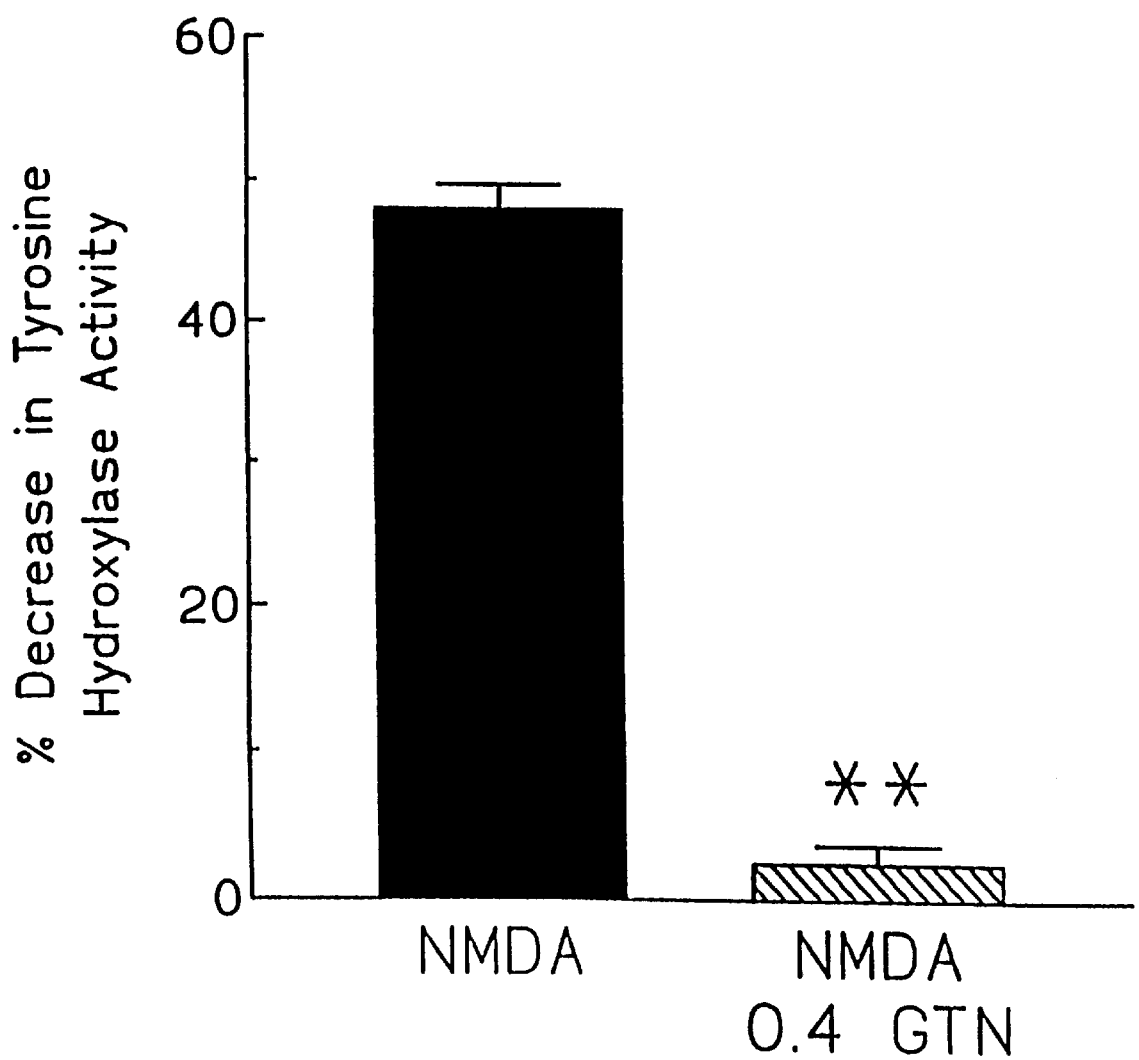
FIG. 27 is a graph showing the effect of GTN (0.4 mg/hr by subcutaneous patch) implanted one hour after an infusion of NMDA into the substantia nigra on striatal TH activity. **P<0.05 compared to animals receiving NMDA alone.
Figure 28:
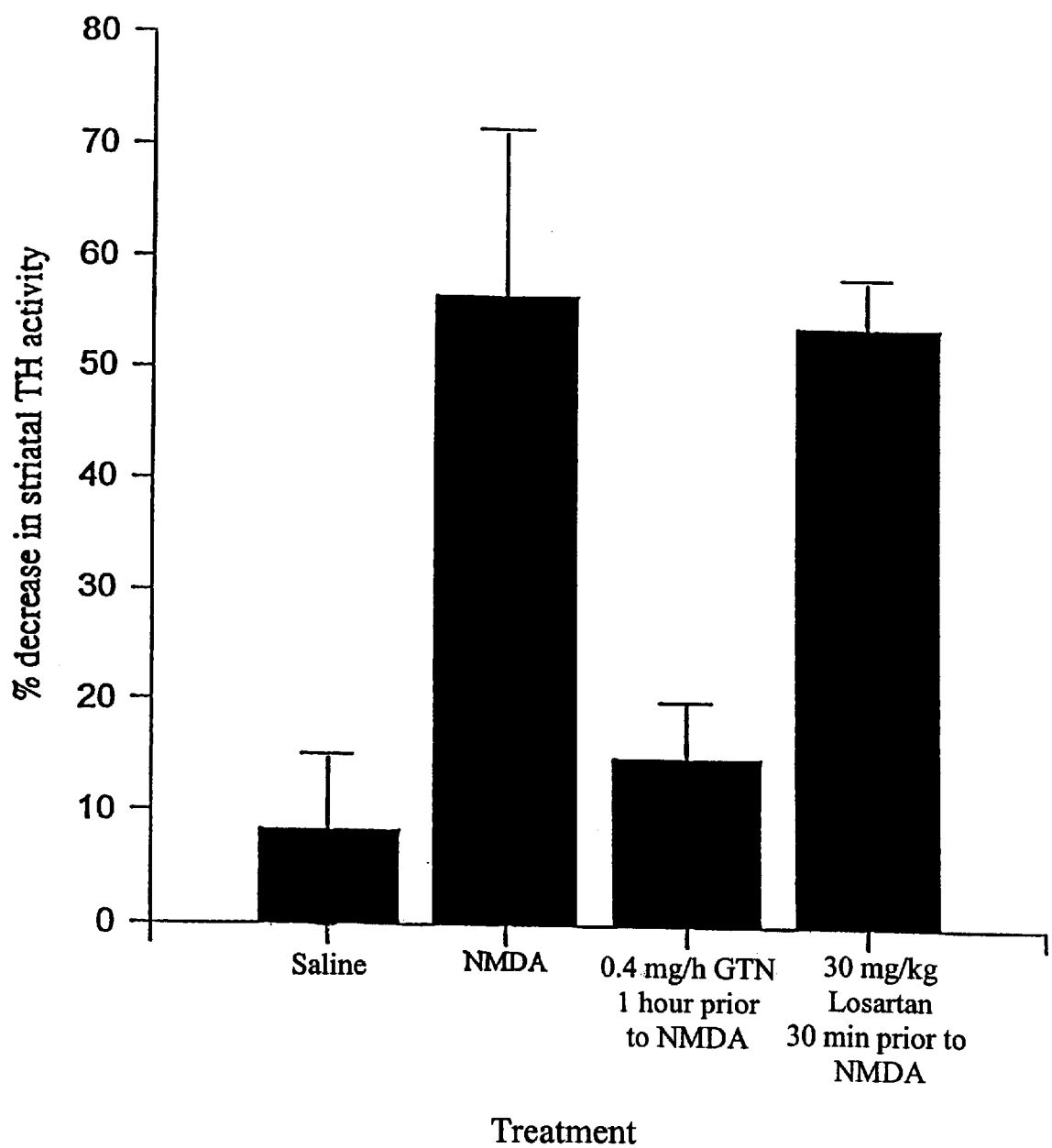
FIG 28 is a graph showing the percent decrease in striatal TH activity in rats pretreated with GTN compared to Losartan, a drug that decreases systemic blood pressure through a mechanism different from that of GTN. Animals pretreated with GTN showed significant amounts of neuroprotection; whereas, animals pretreated with Losartan did not show any evidence of neuroprotection.
Figure 29:
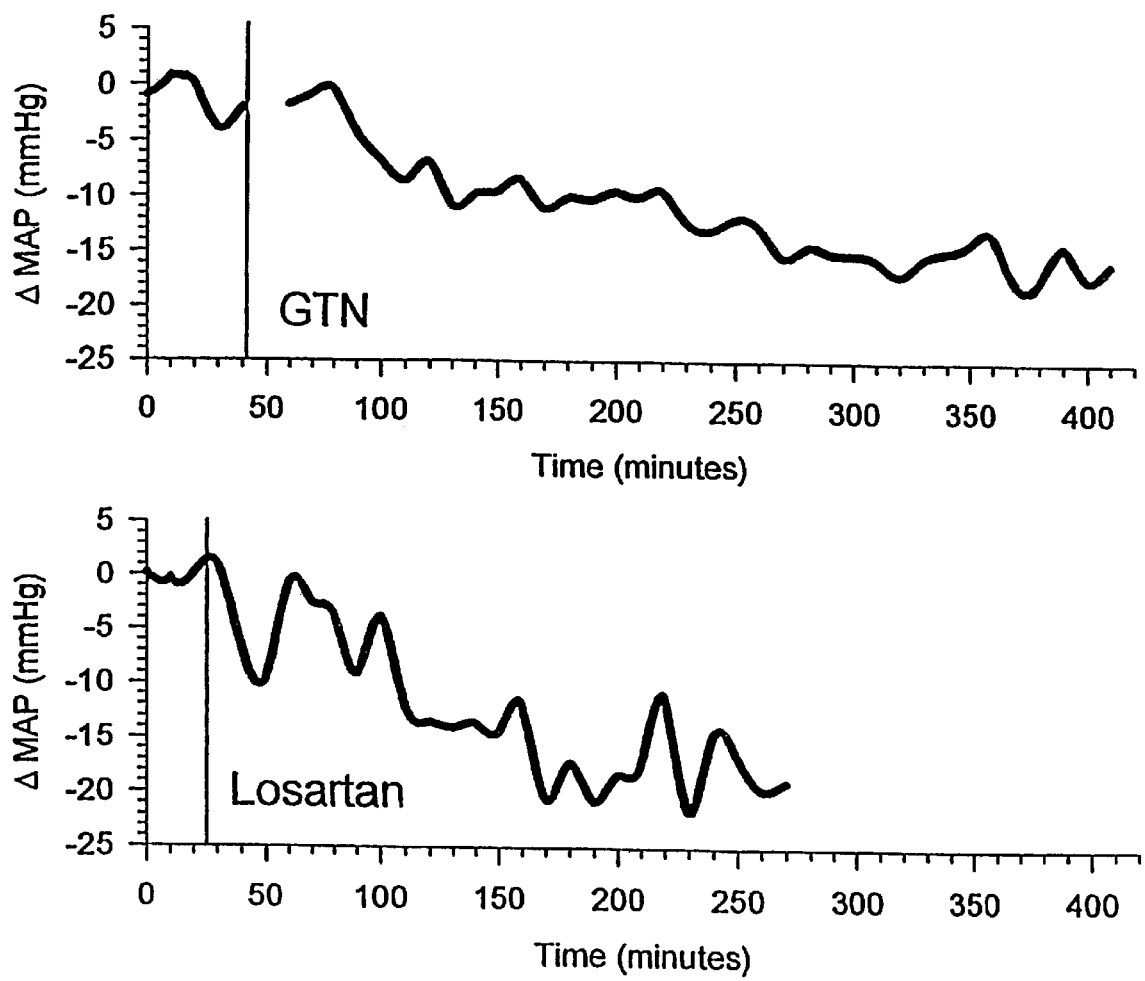
FIG. 29 is a graph showing the blood pressure profiles of animals administered (a) GTN (0.4 mg/hr by subcutaneous patch), or (b) losartan (30 mg/kg by intraperitoneal injection).

In a separate series of experiments, the effects of organic nitrates on focal excitotoxic lesions induced by localized application of NMDA in the rat brain were determined. Male Sprague-Dawley rats were stereotactically infused with NMDA into the right substantia nigra as described in Connop et al. (1995), incorporated herein by reference. Four days later, both striata were dissected and assayed for tyrosine hydroxylase (TH) activity. Loss of TH activity in the striata is a quantitative index of NMDA-induced neuronal cell death in the substantia nigra. The striata of each animal were compared to express neurotoxicity as a percent decrease in TH activity of the ipsilateral striatum as compared to the contralateral striatum. Pretreatment of these animals with GTN (administered as a subcutaneous patch inserted under halothane anesthesia one hour prior to the NMDA infusion) at doses of 0.2 and 0.4 mg/hr produced a dose-dependent reduction in the loss of TH activity from the ipsilateral striatum (FIG. 26). FIG. 27 shows that delaying the administration of GTN until one hour after the NMDA infusion was equally effective at preventing NMDA-induced neuronal cell death in the substantia nigra. Losartan, a drug that decreases systemic blood pressure through a mechanism different from that of GTN, had no neuroprotective effect (FIG. 28). This shows that any vasorelaxation caused by GTN is not the mechanism of the neuroprotection against excitotoxic cell death induced by NMDA. FIG. 29 shows that the doses of losartan and GTN used in these studies caused an equivalent decrease in systemic blood pressure. Male Sprague-Dawley rats with aortic catheters were connected to pressure transducers which recorded blood pressure for 4 to 8 hours. The animals treated with subcutaneous 0.4 mg/hour GTN patches implanted in the dorsal neck region, showed a 15% decrease in MAP 250 minutes post implantation. Animals treated with a single 30 mg/kg intraperitoneal injection of Losartan showed a 20% decrease in MAP 250 minutes after injection. From these data, treatment protocols for the NMDA infusion experiments shown in FIG. 28 were generated.

Example 7

Characterization of neuroreceptor interactions

Figure 30:
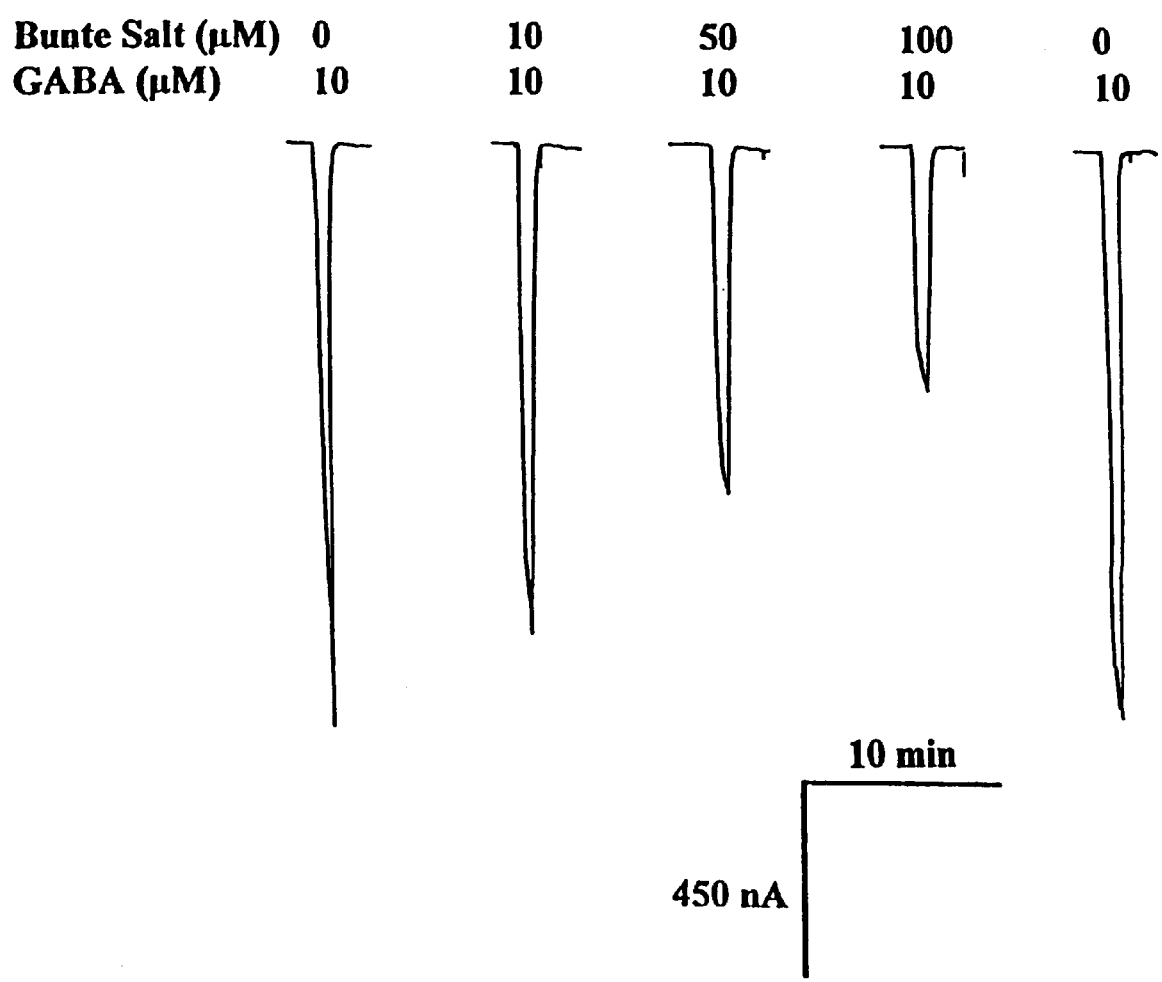
FIG. 30 is a graph showing the effect of compound IVd (Bunte salt, 10–100 μM) on GABA receptor-activated membrane current recorded in an oocyte expressing the α1β2γ2L isoform of the $GABA_A$ receptor.
Figure 31:
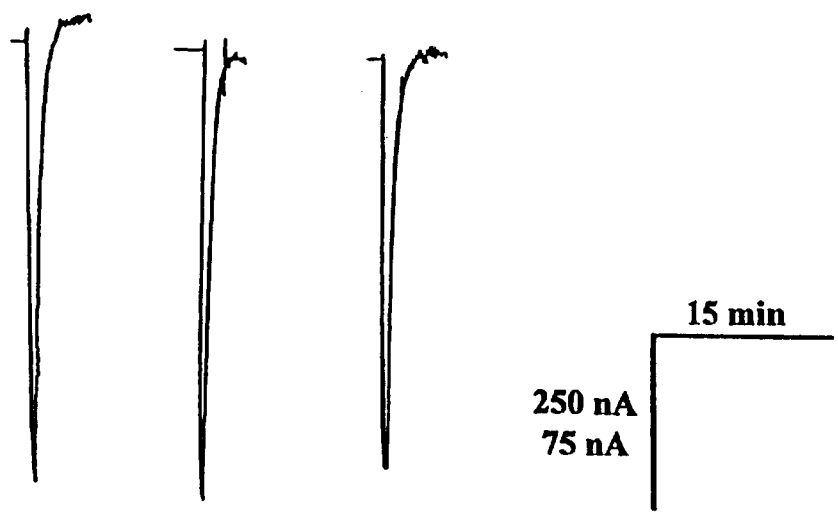
FIG. 31 is a graph showing that nitric oxide donors have no effect on $GABA_A$ receptors expressed in Xenopus oocytes.
Figure 31:
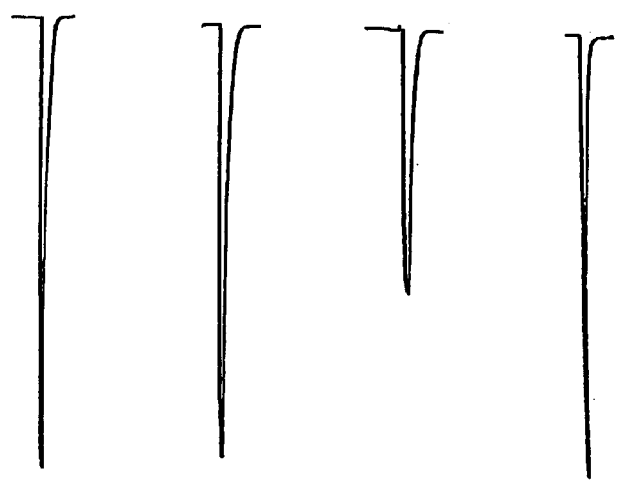
Figure 32:
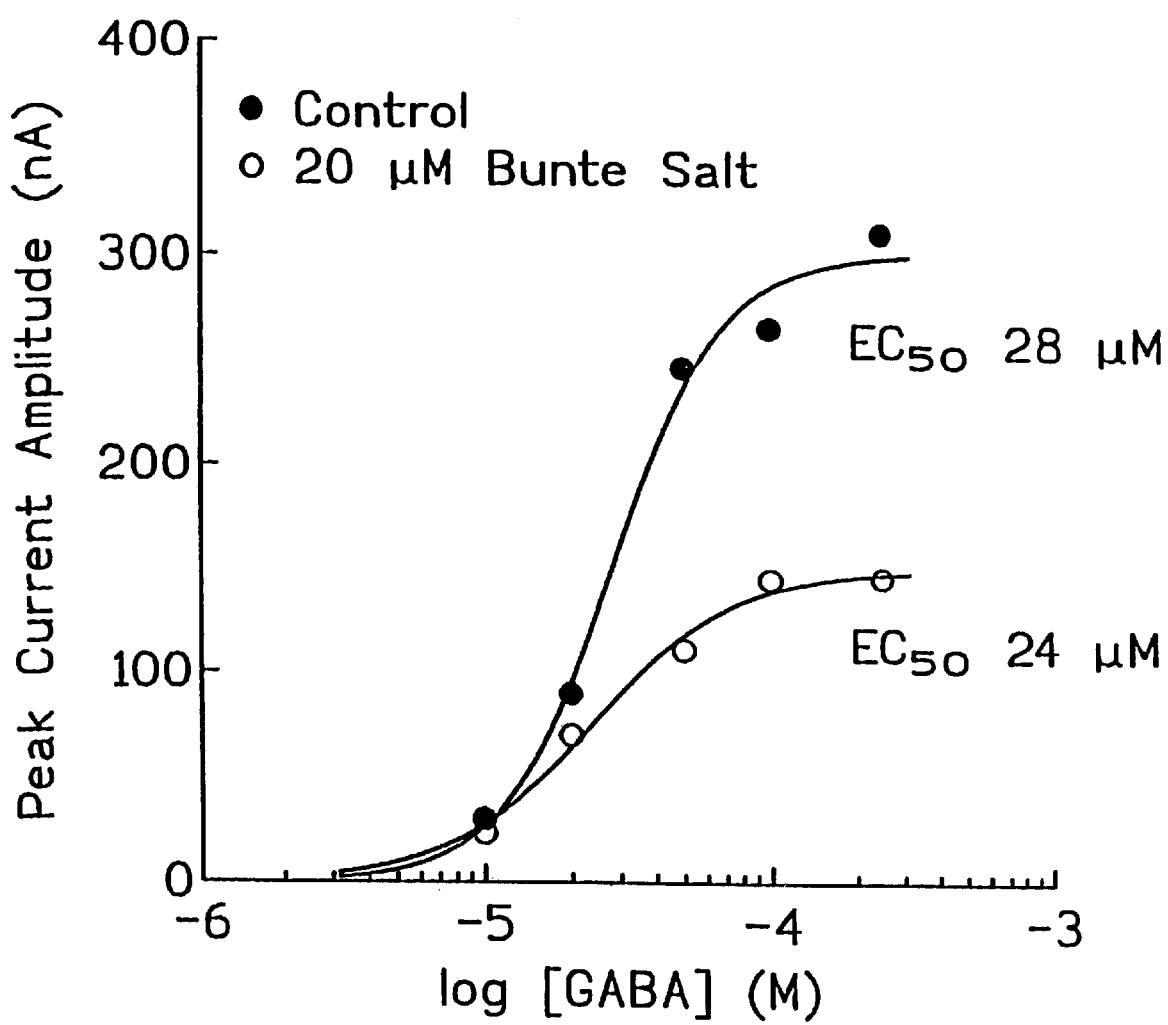
FIG. 32 is a graph showing that the concentration-response relationship for activation of the $GABA_A$ receptor is altered in a non-competitive manner by compound IVd (Bunte salt).

The direct effects of organic nitrates on amino acid neurotransmitter receptors has been tested using the *Xenopus oocyte* expression system and two-electrode voltage-clamp recording methods. Human recombinant γ-aminobutyric acid type A (GABA$_A$) receptors composed of α1β2γ2L subunits were expressed in *Xenopus occytes* as described in Reynolds et al. (1996), incorporated herein by reference. GABA$_A$ receptor-activated membrane current was recorded in individual *oocytes,* and modulation of this current by GTN and organic nitrates described herein was assessed. GABA (10 μM) was applied until the peak steady-state current response was obtained. IVd (Bunte salt) was pre-applied for 30 seconds prior to exposure of the *oocyte* to GABA. At 100 μM, IVd produced a 55% inhibition of the response to 10 μM GABA (FIG. 30). This effect appears to be unrelated to the production or release of nitric oxide, as diethylamine nonoate salt (DEA) and t-butylnitrosonthiol (t-BuSNO) which both spontaneously release nitric oxide in aqueous solution, had no effect on GABA receptor-activated membrane current in an *oocyte* expressing the α1β2γ2L isoform of the $GABA_A$ receptor. In contrast, nitroglycerin (GTN) produced a reversible inhibition of the GABA response (FIG. 31). Organic nitrates such as GTN and IVd do not compete with GABA for binding to the $GABA_A$ receptor. Rather, they are believed to produce an allosteric modulation of the receptor that decreases the maximal current without changing the apparent affinity of the receptor for GABA. For example, compound IVd (Bunte salt, pre-applied for 30 seconds) decreased the peak current amplitude in an *oocyte* from 302 nA to 150 nA. However, the $EC_{50}$ concentration (GABA concentration producing 50% of the maximal response) for GABA was not changed (FIG. 32). Other organic nitrates described herein have been found to have similar inhibitory effects on $GABA_A$ receptor-activated membrane current.

Example 8

Synthesis of IIIe

To acetic anhydride (3 mL) was added gradually, with stirring, 70% nitric acid (0.26 mL), while keeping the temperature between 20–30° by external cooling. With continuous vigorous stirring the mixture was cooled to −30–35° and 2',3'-dideoxy-3-thiocytosine (0.25 g) was added. After 10 min. at −35°, the reaction mixture was heated up to −20° and then stirred at −20–10° for 15 min, and 10 min at 0°. The resulting reaction mixture was poured into ice-water, stirred for 1 hr, then $NaHCO_3$ was added by portions until $CO_2$ evolution ceased. The water solution was extracted with 3×20 mL of ethyl acetate. Combined extracts were dried ($MgSO_4$) and concentrated. 0.38 g of slightly yellowish oil was obtained. The oil crystallized in a day and was recrystallized from $CHCl_3$. Yield 52%. Conversion to the nitrate was evidenced by the significant downfield shift of the C5' proton multiplet from δ 3.6 to 4.85 ppm.

Example 9

Synthesis of nitrate IIIf 0.26 mL (4.15 mmol) conc. $HNO_3$ was added to 2 mL acetic anhydride such that the temperature did not exceed 25–30° C. The mixture was cooled at 0–5° C. and 0.3 g (1.88 mmol) of 5-(1,2-dihydroxyethyl)-4-methylthiazole was added in several portions, the temperature being kept below 5° C. The reaction mixture was stirred at 0–5° C. for 45 min and then 0.45 mL water was added. The mixture was stirred for 30 min and then rotary evaporated. The residue was neutralized by adding 5 mL of saturated $NaHCO_3$ solution and the organic product was extracted with ethyl acetate. The organic layer was concentrated and the dinitrate IIIf was purified through column chromatography (silica gel/ethyl acetate eluant). A slightly yellow solid was obtained. Yield: 0.150 g (32%).

Example 10

Synthesis of nitrate IIIi

Nitrate IIIi was obtained by two routes. Route I proceeded from the elimination reaction of IIIm in basic solution. Route II proceeded from nitration of trans-3-bromo-4-hydroxytetrahydrothiophene-1,1-dioxide, yielding nitrate IIIn, followed by reaction with a weak base, e.g., sodium thiocyanate in 2-butanone. Purification is achieved with silica flash column chromatography using 1:1 hexane:ethyl acetate as eluant.

Example 11

Synthesis of nitrate IIIj 1,4-Dibromo-2,3-butanediol is nitrated: (a) using a nitration mixture prepared from $HNO_3$ and $H_2SO_4$ over 2 days; or (b) using acetyl nitrate reacting for 2 hours. Work-up requires quenching of the reaction mixture in ice-water for an hour, extraction, drying, and evaporation. Successful purification of the title compound by silica gel column chromatography is achieved on a 25 g scale using a mixture of 70% hexane and 30% $CH_2Cl_2$ as eluent.

Example 12

Synthesis of nitrate IIIk and IIIl

Synthesis from dinitrate IIIj proceeded by refluxing with sodium or potassium thiocyanate (2 eq.) in 2-butanone for 8 hr. After cooling, a precipitate was removed by filtration and the filtrate was concentrated. Nitrates IIIk and IIIl were separated by silica flash column chromatography with hexane/dichloromethane as eluent.

Example 13

Synthesis of nitrate IIIm 3,4-Epoxytetrahydrothiophene-1,1-dioxide (250 mg, 1.9 mmol) was refluxed for 24 hrs in 10 mL of water and 25 mg of toluenesulfonic acid. After the first 6 hrs, another 25 mg of the acid was added. The reaction was monitored by thin layer chromatography (5% MeOH in dichloromethane). Purification was by silica flash column chromatography using 5% $MeOH/CH_2Cl_2$ as eluent to afford 200 mg of diol. The diol was nitrated in a cooled solution of conc. sulfuric acid (2 mol eq.), nitric acid (70%, 2 mol eq.) in an ice bath. The temperature was maintained as close to 0° C. as possible. The ice bath was removed and the mixture was allowed to stir for 1 hour (reaction was monitored by thin layer chromatography, 100% $CH_2Cl_2$ eluent). The acid layer was removed and the organic layer washed with: (i) water; (ii) 10% sodium carbonate; (iii) 10% urea; (iv) water. Drying over sodium sulfate, filtration and concentration, yielded crude product which was purified by flash column chromatography, with dichloromethane as eluent. An alternative route involves direct nitration of 3,4-epoxytetrahydrothiophene-1,1-dioxide in a similar nitration mixture.

Example 14

Synthesis of nitrate IVk 1.17 mL (18.2 mmol) concentrated $HNO_3$ was added, under stirring and cooling (0–5° C.), to 1 mL (18.2 mmol) concentrated $H_2SO_4$ and then 2 g (14 mmol) of 4-methyl-5-(2-hydroxyethyl)thiazole was added dropwise into the nitration mixture, the temperature being kept under 10° C. The mixture was stirred for 3 hours at room temperature, diluted with 10 mL of water and neutralized with solid $NaHCO_3$. The organic product was extracted with ethyl acetate and purified by column chromatography (silica gel/ ethyl acetate eluant) to produce a colorless oily product. Yield 1.18 g (45%).

Example 15

Synthesis of nitrate Ivi 0.03 g (0.035 ml) of allyl cyanide was added to a stirred suspension of 0.22 g (0.5 mmol) of Tl (NO$_3$)$_3$.3H$_2$O in 2 mL of pentane. After 20 min of vigorous stirring, the pentane solution was decanted and evaporated to dryness. After evaporation the residual oil (0.44 g) was columned (CH$_2$Cl$_2$, Rf 0.64 (CH$_2$Cl$_2$). Clean oil immediately crystallized during an attempt to dissolve it in CDCl$_3$. Yield 0.065 g (76%). The structure of IVn was confirmed by X-ray analysis. IR (film): 1297.03, 1678.91, 2258.91 (CN). Mass spec. m/z (CI$^+$ 'fragment, %): 191.9 (M+H, 2.44), 129.0(16.41), 81.9 (100). Calculated for C$_4$H$_5$N$_3$O$_6$ 191.02.

Example 16

Synthesis of nitrate IVn 0.9 g (0.75 mL, 4.92 mmol) of allyphenyl sulfone was added dropwise to a stirred suspension of 2.43 g (5.47 mmol) of Tl (NO$_3$)$_3$.3H$_2$O in 10 mL of pentane. The resulting mixture was stirred overnight. The pentane solution was decanted. 2×10 mLl of MeOH (methanol) were added to the reaction mixture, stirred for 10 minutes and extracts were added to the pentane solution. The combined extracts were evaporated to dryness and purified by silica flash column chromatography using CH$_2$Cl$_2$ as eluant. Yield 0.08 g (15%). IR (KBr): 1152.39, 1290.91, 1273.12, 1353.83, 1646.08. Mass spec. m/z (CI$^+$'fragment, %): 307.0 (M+1, 66.5), 244.0 (100%). Calculated for C$_9$H$_{10}$N$_2$O$_8$S 306.02.

Example 17

Synthesis of nitrate Va 2.2 g (7.3 mmol) of nitrate IVd was dissolved in 5 of cold H$_2$O$_2$ (30%, 0° C.) and then 1 g of 10% H$_2$SO$_4$ was added. The mixture was stirred at 0–5° C. until a white oil separated (ca. 30–60 min). The aqueous layer was discarded and the oil was dissolved in dichloromethane, washed successively with water, then NaHCO$_3$ solution and finally water. The organic solution was dried over MgSO$_4$. Removal of the solvent produced 1.3 g of the crude product which was purified by column chromatography (Silicagel, CH$_2$Cl$_2$/hexanes: 70/30). Yield: 0.650 g (45%).

Example 18

Synthesis of nitrate Vc 3 g (8.88 mmol) of 1,4-dibromo-2,3-dinitrobutanediol and 2.81 (18 mmol) of Na$_2$S$_2$O$_3$.5H$_2$O were dissolved in a mixture of 100 mL of MeOH and 45 mL of H$_2$O. The resulting solution was heated during 4 days at 40–45°. After this time the reaction mixture was partially evaporated to reduce the volume of solvents. The resulting mixture was extracted 4×50 mL of ethyl ether. The extracts were combined, washed (H$_2$O), dried (MgSO$_4$) and evaporated to minimum. Column chromatography afforded the title compound in 10% yield, separated from Vb, the major product.

Example 19

Synthesis of nitrate IIIb

The synthetic route employed for synthesis of the hexanitrate IIIh is shown in the Scheme:

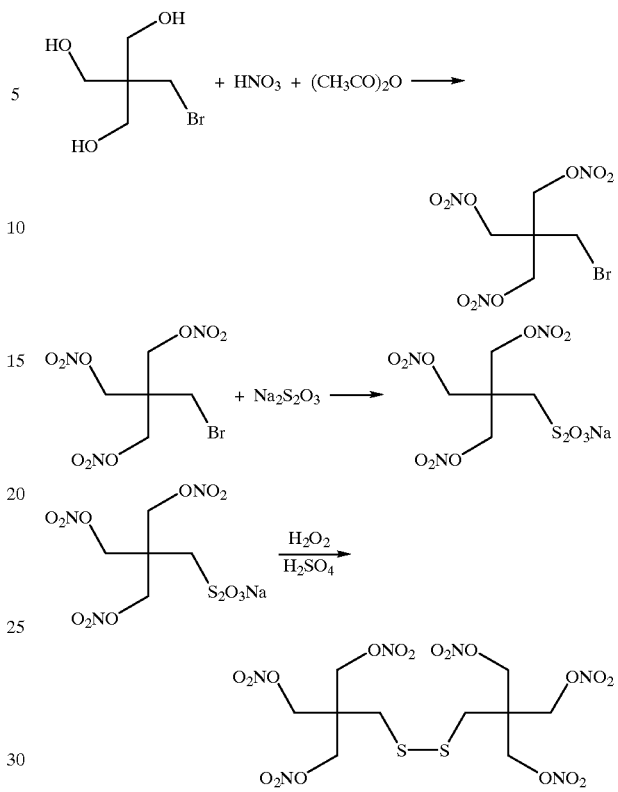

REFERENCES

Abe, K., C. Takeyama, K. Yoshimura, "Effect of S-8510, a novel benzodiazepine receptor partial inverse agonist, on basal forebrain lesioning-induced dysfunction in rats", Eur. J. Pharmacol. 347 (1998) 145–152.

Arancio, O., E. R. Kandel, R. D. Hawkins, "Activity-dependent long-term enhancement of transmitter release by presynaptic 3',5'-cyclic GMP in cultured hippocampal neurons", Nature 376 (1995) 74–80.

Barger, S. W., R. R. Riscus, P. Ruth, F. Hofmann, M. P. Mattson, "Role of cyclic GMP in the regulation of neuronal calcium and survival by secreted forms of β-amyloid precursor protein", J. Neurochem. 64 (1995) 2087–2096.

Bennett et al., Can. J. Physiol. Pharmacol. 70 (1992) 1297.

Berge et al., "Pharmaceutical Salts", J. Pharm. Sci. 66 (1977) 1–19.

Bernabeu, R. N. Schroder, J. Quevedo, M. Cammarota, I. Izquierdo, J. H. Medina, "Further evidence for the involvement of a hippocampal cGMP/cGMP-dependent protein kinase cascade in memory consolidation", NeuroReport 8 (1997) 2221–2224.

Bernabeu, R., P. Schmitz, M., P. Faillace, I. Izquierdo, J. H. Medina, "Hippocampal cGMP and cAMP are differentially invloved in memory processing of inhibitory avoidance learning", NeuroReport 7 (1996) 585–588.

Bloeman, P. G. et al., FEBS Lett., 357 (1995) 140.

Briscoe et al., Am. J Physiol. 1233 (1995) 134.

Bullock, R., A Zauner, J. J. Woodward, J. Nyseros, S. C. Choi, J. D. Ward, A. Marmarou, H. F. Young, "Factors affecting excitatory amino acid release following severe human head injury", J. Neurosurg. 89 (1998) 507–518.

Chan, P. H., M. Kawase, K. Murakami, S. F. Chen, Y, Li, B. Calagui, L. Reola, E. Carlson, C. J. Epstein, "Overexpression of SOD1 in transgenic rats protects vulnerable neurons against ischemic damage after global cerebral ischemia and reperfusion", J. Neurosic. 18 (1998) 8292–8299.

Chen, J., T. Nagayama, K. Jin, R. A. Stetler, R. L. Zhu, S. H. Graham, R. P. Simon, "Induction of caspase-3-like protease may mediate delayed neuronal death in the hippocampus after transient cerebral ischemia", J. Neurosci. 18 (1998) 4914–4928.

Cohen, G. M., "Caspases: the executioners of aopotosis", Biochem. J. 326 (1997) 1–16.

Connop et al., Brain Research 676 (1995) 124–132.

Du, Y., K. R. Bales, R. C. Dodel, E. Hamilton-Byrd, J. W. Horn, D. L. Czilli, L. K. Simmons, B. Ni, S. M. Paul, "Activation of a caspase-3-related cysteine protease is required for glutamate-mediated apoptosis of cultured cerebellar granule neurons", Proc. Natl. Acad. Sci. U.S.A. 94 (1997) 11657–11662.

Endres, M., S. Namura, M. Shimizu-Sasamata, C. Waebar, L. Zhang, T. Gomez-Isla, B. T. Hyman, M. A. Moskowitz, "Attenuation of delayed neuronal death after mild focal ischemia in mice by inhibition of the caspase family", J. Cereb. Blood Flow Metab. 18 (1998) 238–247.

Estevez, A. G., N. Spear, J. A. Thompson, T. L. Cornwell, R. Radi, L. Barbeito, J. S. Beckman, "Nitric oxide-dependent production of cGMP supports the survival of rat embryonic motor neurons cultured with brain-derived neurotrophic factor", J. Neurosci. 18 (1998) 3708–3714.

Farinelli, S. E., D. S. Park, L. A. Greene, "Nitric oxide delays the death of trophic factor-deprived PC12 cells and sympathetic neurons by a cGMP-mediated mechanism", J. Neurosci. 16 (1996) 23–25–2234.

Furukawa, K., S. W. Barger, E. M. Blalock, M. P. Mattson, "Activation of $K^+$ channels and suppression of neuronal activity by secreted β-amyloid precursor protein", Nature 379 (1996) 74–78.

Gaetani, P., A. Pasqualin, R. Rodriguez y Baena, E. Borasio, F. Marzatico, "Oxidative stress in the human brain after subarachnoid hemorrhage", J. Neurosurg. 89 (1998) 748–754.

Goda, H., H. Ooboshi, H. Nakane, S. Ibayashi, S. Sadoshima, M. Fujishima, "Modulation of ischemia-evoked release of excitatory and inhibitory amino acids by adenosine A1 receptor agonist", Eur. J. Pharmacol. 357 (1998) 149–155.

Gottron, F. J., H. S. Ying, D. W. Choi, "Caspase inhibition selectively reduces the apoptotic component of oxygen-glucose deprivation-induced cortical neuronal cell death", Mol. Cell. Neurosci. 9 (1997) 159–169.

Haviv, R., L. Lindenboim, H. Li, J. Yuan, R. Stein, "Need for caspases in apoptosis of trophic factor-deprived PC12 cells", J. Neurosci. Res. 50 (1997) 69–80.

Higashi et al., Neuropathol. Appl. Neurobiol. 21 (1995) 480–483.

Huang, F. P., L. F. Zhou, G. Y. Yang, "Effects of mild hypothermia on the release of regional glutamate and glycine during extended transient focal cerebral ischemia in rats", Neurochem. Res. 23 (1998) 991–996.

Ibarrola, D., H. Seegers, A. Jaillard, M. Hommel, M. Decorps, R. Massarelli, "The effect of eliprodil on the evolution of a focal cerebral ischaemia in vivo", Eur. J. Pharmacol. 352 (1998) 29–35.

Jiang et al., J. Cereb. Blood Flow Metab. 18 (1998) 758–767.

Kesner, NIDA Res. Monographs 97 (1990) 22–36.

Kim, Y. M., R. V. Talanian, T. R. Billiar, "Nitric oxide inhibits apoptosis by preventing increases in caspase-3-like activity via two distinct mechanisms", J. Biol. Chem. 272 (1997) 31138–31148.

Louw, R., H. P. W. Vermeeren, J. J. A. Van Asten, W. J. Ultee, J.Chem.Soc., Chem.Comm. (1976) 496–497

Macdonald, R. L., M. Stoodley, "Pathophysiology of cerebral ischemia", Neurol. Med. Chir. (Tokyo) 38 (1998) 1–11.

Mattson and Scheff, J. Neurotrauma 11(1994) 3–33.

McDonald and Bennett, Can. J. Physiol. Pharmacol 68 (1990) 1552.

McGuire et al., J. Pharmacol. Exp. Ther. 271 (1994) 708.

Mizuno, A., K. Umemura, M. Nakashima, "Inhibitory effect of MCI-186, a free radical scavenger, on cerebral ischemia following rat middle cerebral artery occlusion", Gen. Pharmacol. 30 (1998) 575–578.

Mordenti, "Man versus beast: Pharmacokinetic scaling in mammals", J. Pharm. Sci. 75 (1986) 1028–1040.

Morgan et al., "Approaches to the discovery of non-peptide ligands for peptide receptors and peptidases", In Ann. Rep. Med. Chem. (Virick F. J., et al.) (1989) pp. 243–253, Academic Press, San Diego, Calif.

Morikawa et al., J. Neurosci. 18 (1998) 9727–9732.

Namura, S., J. Zhu, K. Fink, M. Endres, A Srinivasan, K. J. Tomaselli, J. Yuan, M. A. Moskowitz, "Activation and cleavage of caspase-3 in apoptosis induced by experimental cerebral ischemia", J. Neurosci. 18 (1998) 3659–3668.

Ni, B., X. Wu, Y. Su, D. Stephenson, E. B. Smalstig, J. Clemens, S. M. Paul, "Transient global forebrain ischemia induces a prolonged expression of the caspase-3 mRNA in rat hippocampal CA1 pyramidal neurons", J. Cereb. Blood Flow Metab. 18 (1998) 248–256.

Nicholson, D. W., N. A. Thornberry, "Caspases: killer proteases", Trends Biochem. Sci. 22 (1997) 299–306.

Nurse and Corbett, J. Cereb. Blood Flow Metab. 16 (1996) 474–480.

O'Neill, M. J., A. Bond, P. L. Ornstein, M. A. Ward, C. A. Hicks, K. Hoo, D. Bleakman, D. Lodge, "Decahydrosio-quinolines: novel competitive AMPA/kainate antagonists with neuroprotective effects in global cerebral ischaemia", Neuropharmacol. 37 (1998) 1211–1222.

Ouellette, R. J., R. J. Bertsch, J. Org. Chem. 41 (1976) 2782–2783.

Owais, M. et al., Antimicrob. Agents Chemother. 39 (1995) 180.

Pallares, M., M. Darnaudery, J. Day, M. Le Moal, W. Mayo, "The neurosteroid pregnenolone sulfate infused into the nucleus basalis increases both acetylcholine release in the frontal cortex or amygdala and spatial memory", Neurosci. 87 (1998) 551–558.

Ranade, V. V., J. Clin. Pharmacol. 29 (1989) 685.

Reynolds and Maitra, Eur. J. Pharmacol. 314 (1996) 151–156.

Strejan et al., J. Neuroimmunol. 7 (1984) 27.

Stewart et al., Can. J. Physiol. Pharmacol. 67 (1989) 403.

Sydserff et al., Br. J. Pharmacol. 114 (1995) 1631–1635.

Tagami, M. K. Yamagata, K. Ikeda, Y. Nara, H. Fujino, A. Kobota, F. Numano, Y. Yamori, "Vitamin E prevents apoptosis in cortical neurons during hypoxia and oxygen reperfusion", Lab. Invest. 78 (1998) 1415–1429.

Umemura, K., A. Shimakura, M. Nakashima, "Neuroprotective effect of a novel AMPA receptor antagonist, YM90K, in a rat focal cerebral ischaemia", Brain Res. 773 (1997) 61–65.

Umezawa et al., Biochem. Biophys. Res. Commun. 153 (1988) 1038.

Venault, P. G. Chapouthier, L., Prado de Carvalho and Rossier, J., Encephale, 18 (1992) 655.

Wittkowsky, Pharmacotherapy 18 (1998) 945–1005.

Wu, J., Y. Wang, M. J. Rowan, R. Anwyl, "Evidence for involvement of the cGMP-protein kinase G signaling system in the induction of long-term depression, but not long-term potentiation, in the dentate gyrus in vitro", J. Neurosci. 18 (1998) 3589–3596.

Yang, K., J. D. Artz, J. Lock, C. Sanchez, B. M. Bennett, A. B. Fraser, G. R. Thatcher, J. Chem. Soc., Perkin Trans. 1 (1996) 1073–1075.

Yang, Y. L., W. H. Pan, T. H. Chiu, M. T. Lin, "Striatal glutamate release is important for development os ischemic damage to strital neurons during rat heatstroke", Brain Res. 795 (1998) 121–127.

What is claimed is:

1. A method for mitigating cerebral damage due to ischemia in a subject in need thereof comprising administering to said subject an effective amount of a therapeutic compound such that cerebral damage is mitigated, wherein the therapeutic compound has the formula (Formula I):

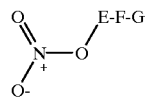

wherein E, F, G are organic radicals which may contain inorganic counterions, wherein F and G are not substituted or unsubstituted pyridyl, and wherein, when E is $C_1$ alkane, F and G are not both $C_1$ to $C_3$ alkyl radicals bearing one or more nitrate groups or an O linkage.

2. The method of claim 1, wherein administering the therapeutic compound to the subject modulates cellular free radical damage.

3. A method of mitigating cerebral damage due to ischemia in a subject, comprising administering to said subject an effective amount of a therapeutic compound such that cerebral damage is mitigated, wherein the therapeutic compound has the formula (Formula II):

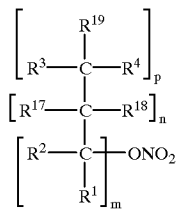

in which:

m, n, p are integers from 0 to 10;

$R^{3,17}$ are each independently hydrogen, a nitrate group, or A;

$R^{1,4}$ are each independently hydrogen or A;

where A is selected from: a substituted or unsubstituted aliphatic group (preferably a branched, or straight-chain aliphatic moiety having from 1 to 24 carbon atoms in the chain), which optionally contains O, S, $NR^6$ and unsaturations in the chain, optionally bearing from 1 to 4 hydroxy, nitrate, amino or aryl, or heterocyclic groups; an unsubstituted or substituted cyclic aliphatic moiety having from 3 to 7 carbon atoms in the aliphatic ring, which optionally contains O, S, $NR^6$ and unsaturations in the ring, optionally bearing from 1 to 4 hydroxy, nitrate, amino or aryl, or heterocyclic groups; an unsubstituted or substituted aliphatic moiety constituting a linkage of from 0 to 5 carbons, between $R^1$ and $R^3$ and/or between $R^{17}$ and $R^4$, which optionally contains O, S, $NR^6$ and unsaturations in the linkage, and optionally bearing from 1 to 5 hydroxy, nitrate, amino or aryl, or heterocyclic groups; a substituted or unsubstituted aliphatic group (preferably a branched, cyclic or straight-chain aliphatic moiety having from 1 to 24 carbon atoms in the chain), containing carbonyl linkages (e.g. C=O, C=S, C=NOH), which optionally contains O, S, $NR^8$ and unsaturations in the chain, optionally bearing from 1 to 4 hydroxy, nitrate, amino or aryl, or heterocyclic groups; a substituted or unsubstituted aryl group; a heterocyclic group; amino (including alkylamino, dialkylamino (including cyclic amino, diamino and triamino moieties), arylamino, diarylamino, and alkylarylamino); hydroxy; alkoxy; a substituted or unsubstituted aryloxy;

$R^2$, $R^5$, $R^{18}$, $R^{19}$ are optionally hydrogen, A, or X-Y;

where X is F, Br, Cl, $NO_2$, $CH_2$, $CF_2$, O, NH, NMe, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$. $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_2HM$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, $C(O)$, $C(O)R^{12}$, $C(O)(OR^{13})$, $PO_2H$, $PO_2M$, $P(O)(OR^{14})$, $P(O)(R^{13})$, SO, $SO_2$, $C(O)(SR^{13})$, $SR^6$, $SSR^7$ or $SSR^5$;

Y is F, Br, Cl, $CH_3$, $CF_2H$, $CF_3$, OH, $NH_2$, $NHR^6$, $NR^6R^7$, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_2HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, $C(O)R^{12}$, $C(O)(OR^{13})$, $C(O)(SR^{13})$, $SR^5$, $SSR^7$ or $SSR^5$, or does not exist;

$R^6$, $R^7$, $R^8$, $R^9$, $R^{11}$, $R^{12}$, $R^{13}$, $R^{14}$, $R^{15}$, $R^{16}$ are the same or different alkyl or acyl groups containing 1–24 carbon atoms which may contain 1–4 $ONO_2$ substituents; or $C_1$–$C_6$ connections to $R^1$–$R^4$ in cyclic derivatives; or are each independently hydrogen, a nitrate group, or A; and M is H, $Na^-$, $K^+$, $NH_4^+$, $N^+H_kR^{11}_{(4-k)}$ where k is 0–3, or other pharmaceutically acceptable counterion;

wherein A is not substituted or unsubstituted pyridyl, and, when m=n=p=1, that $R^1$, $R^2$, $R^{18}$, $R^{19}$ are selected from the group consisting of H, O linkage, and $C_1$–$C_2$ alkyl, wherein said $C_1$–$C_2$ alkyl is optionally substituted with nitrate, that $R^3$, $R^{17}$ are selected from the group consisting of H, nitrate, O linkage, and $C_1$–$C_2$ alkyl, wherein said $C_1$–$C_2$ alkyl is optionally substituted with nitrate, and that $R^4$ is not H or $C_1$–$C_3$ alkyl.

4. The method of claim 3, wherein $R^{19}$ is X-Y.

5. The method of claim 4, wherein:

$R^1$ and $R^3$ are the same or different and selected from H, $C_1$–$C_4$ alkyl chains, which may include one O, linking $R^1$ and $R^3$ to form pentosyl, hexosyl, cyclopentyl, or cyclohexyl rings, which rings optionally bear hydroxyl substituents;

$R^2$ and $R^4$, are the same or different and selected from H, a nitrate group, $C_1$–$C_4$ alkyl optionally bearing 1–3 nitrate group, and acyl groups (—C(O)$R^5$);

$R^7$, $R^{11}$ are the same or different $C_1$–$C_8$, alkyl or acyl;

$R^5$, $R^6$, $R^8$, $R^9$, $R^{12}$, $R^{13}$, $R^{14}$, $R^{15}$, $R^{16}$ are the same or different alkyl groups containing 1–12 carbon atoms which may contain 1–4 $ONO_2$ substituents; or $C_1$ or $C_2$ connections to $R^1$–$R^3$ in cyclic derivatives; and M is H, $Na^+$, $K^+$, $NH_4^+$, $N^+H_kR^{11}_{(4-k)}$ where k is 0–3.

6. The method of claim 5, wherein m=1, n=0, p=1.

7. The method of claim 6, wherein:

X is $CH_2$, O, NH, NMe, CN, NHOH, $N_2H_3$, $N_2H_2R^{13}$, $N_2HR^{13}R^{14}$, $N_3$, S, SCN, $SCN_2H_2(R^{15})_2$, $SCN_2H_3(R^{15})$, $SC(O)N(R^{15})_2$, $SC(O)NHR^{15}$, $SO_3M$, SH, $SR^7$, $SO_2M$, $S(O)R^8$, $S(O)_2R^9$, $S(O)OR^8$, $S(O)_2OR^9$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{15}$, $CO_2M$, $CO_2H$, $CO_2R^{11}$, C(O), $C(O)R^{12}$, $C(O)(OR^{13})$, $PO_2M$, $P(O)(OR^{14})$, $P(O)(R^{13})$, SO, $SO_2$, $C(O)(SR^{13})$, $SSR^5$; and Y is CN, $N_2H_2R^{13}$, $N_2HR^{13}R^{14}$, $N_3$, SCN, $SCN_2H_2(R^{15})_2$, $SC(O)N(R^{15})_2$, $SC(O)NHR^{16}$, $SO_3M$, $SR^4$, $SO_2M$, $PO_3HM$, $PO_3M_2$, $P(O)(OR^{15})(OR^{16})$, $P(O)(OR^{16})(OM)$, $P(O)(R^{15})(OR^8)$, $P(O)(OM)R^{16}$, $CO_2M$, $CO_2H$, $CO_2R^{11}$, $C(O)R^{12}$, $C(O)(SR^{13})$, $SR^5$, $SSR^5$, or does not exist.

8. The method of claim 7, wherein:

$R^5$, $R^6$, $R^8$, $R^9$, $R^{12}$, $R^{13}$, $R^{14}$, $R^{15}$, $R^{16}$ are the same or different alkyls containing 1–12 carbon atoms; or $C_1$ or $C_2$ connections to $R^1$ or $R^3$ in cyclic derivatives;

X is $CH_2$, O, NH, NMe, S, $SO_3M$, SH, $SR^7$, $SO_2M$, $S(O)R^8$, $S(O)_2R^9$, $S(O)OR^8$, $S(O)_2OR^9$, $PO_3M_2$, $P(O)(OR^{15})(OR^{16})$, $P(O)(OR^{16})(OM)$, $P(O)(R^{15})(OR^8)$, $PO_3HM$ or $P(O)(OM)R^{16}$; and Y is $SO_2M$, $SO_3M$, $PO_3HM$, $PO_3M_2$, $P(O)(OR^{15})(OR^{16})$, $P(O)(OR^{16})(OM)$, $SR^5$, $SR^7$ or $SSR^6$, or does not exist.

9. The method of claim 1, wherein the therapeutic compound is administered orally, intravenously, buccally, transdermally or subcutaneously.

10. The method of claim 1, further comprising administering the therapeutic compound in a pharmaceutically acceptable vehicle.

11. The method of claim 1, wherein administering the therapeutic compound to the subject modulates an activity of the glutamate neuroreceptor.

12. The method of claim 1, wherein administering the therapeutic compound to the subject modulates an activity of a non-glutamate neuroreceptor.

13. The method of claim 1, wherein administering the therapeutic compound to the subject modulates cerebral guanylyl cyclase activity.

14. The method of claim 1, wherein administering the therapeutic compound to the subject modulates apoptosis.

15. The method of claim 3, wherein the therapeutic compound is administered orally, intravenously, buccally, transdermally or subcutaneously.

16. The method of claim 3, further comprising administering the therapeutic compound in a pharmaceutically acceptable vehicle.

17. The method of claim 1, wherein administering the therapeutic compound to the subject modulates levels of cyclic nucleotide cGMP and/or cAMP.

18. The method of claim 7, wherein p=1, and $R^6$–$R^{16}$ are the same or different alkyl or acyl groups containing 1–24 carbon atoms which may contain 1–4 $ONO_2$ substituents, or $C_1$–$C_6$ connections to $R^1$–$R^4$ is cyclic derivatives.

19. The method of claim 7, wherein X is $SSR^5$ or $SSR^7$, and Y does not exist.

20. The method of claim 18, wherein $R^{18}$ is A, m=1, and n=0–1.

21. The method of claim 19, wherein m, n, p are integers from 0–2, and $R^5$ is A.

22. The method of claim 21, wherein A is selected from a substituted or unsubstituted aliphatic group (preferably a branched or straight-chain aliphatic moiety having from 1 to 24 carbon atoms in the chain), which optionally may contain O, S, $NR^6$ and unsaturations in the chain, optionally bearing from 1 to 4 hydroxy, nitrate, amino or aryl, or heterocyclic groups; an unsubstituted or substituted cyclic aliphatic moiety having from 3 to 7 carbon atoms in the aliphatic ring, which optionally may contain O, S, $NR^6$ and unsaturations in the ring, optionally bearing from 1 to 4 hydroxy, nitrate, amino or aryl, or heterocyclic groups; a substituted or unsubstituted aliphatic group (preferably a branched, cyclic, or straight-chain aliphatic moiety having from 1 to 24 carbon atoms in the chain), containing carbonyl linkages (e.g., C=O, C=S, C=NOH), which optionally may contain O, S, $NR^6$ and unsaturations in the chain, optionally bearing from 1 to 4 hydroxy, nitrate, amino or aryl, or heterocyclic groups; a substituted or unsubstituted aryl group; a heterocyclic group; amino (including alkylamino, dialkylamino (including cyclic amino, diamino and triamino moieties), arylamino, diarylamino, and alkylarylamino); hydroxy; alkoxy; a substituted or unsubstituted aryloxy.

23. The method of claim 22, wherein m=n=p=1, $R^1$, $R^2$, $R^3$, $R^4$, $R^{18}$ are H, $R^{17}$ is nitrate, and $R^{19}$ is $SSR^5$; where $R^5$ is A, and where A is a heterocyclic group.

24. The method of claim 22, wherein m=n=p=1, $R^1$, $R^2$, $R^3$, $R^4$, $R^{18}$ are H, $R^{17}$ is nitrate, and $R^{19}$ is $SSR^5$; where $R^5$ is A, and where A is a substituted or unsubstituted aryl group.

25. The method of claim 22, wherein m=n=p=1, $R^1$, $R^2$, $R^3$, $R^4$, $R^{18}$ are H, $R^{17}$ is nitrate, and $R^{19}$ is $SSR^5$; where $R^5$ is A, and where A is a substituted or an unsubstituted cyclic aliphatic moiety having from 3 to 7 carbon atoms in the aliphatic ring, which optionally may contain O, S, $NR^6$ and unsaturations in the ring, optionally bearing from 1 to 4 hydroxy, or nitrate, or amino or aryl, or heterocyclic groups; a substituted or unsubstituted aliphatic group (preferably a branched, cyclic or straight-chain aliphatic moiety having from 1 to 24 carbon atoms in the chain), containing carbonyl linkages (e.g. C=O, C=S, C=NOH), which optionally may contain O, S, $NR^8$ and unsaturations in the chain, optionally bearing from 1 to 4 hydroxy, or nitrate, or amino or aryl, or heterocyclic groups.

26. The method of claim 22, wherein m=n=p=1, $R^1$, $R^2$, $R^3$, $R^4$, $R^{18}$ are H, $R^{17}$ is nitrate, $R^{19}$ is $SSR^5$; where $R^5$ is A, and where A is a substituted or unsubstituted aliphatic group (preferably a branched or straight-chain aliphatic moiety having from 1 to 24 carbon atoms in the chain), which optionally may contain O, S, $NR^6$ and unsaturations in the chain, optionally bearing from 1 to 4 hydroxy, or nitrate, or amino or aryl, or heterocyclic groups.

27. The method of claim 20, wherein the therapeutic compound has a formula selected from the group consisting of:

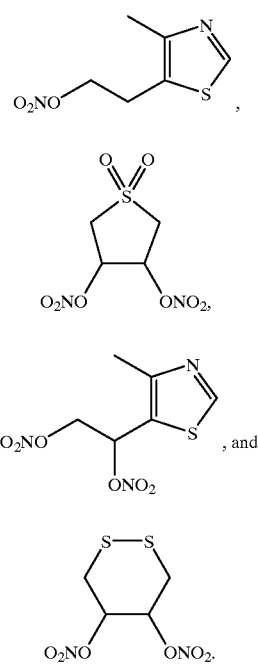

28. The method of claim 26, wherein the therapeutic compound has the formula (Formula Va):

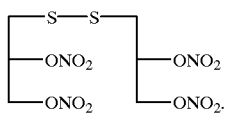

29. The method of claim 26, wherein A is a substituted or unsubstituted aliphatic group (preferably a branched or straight-chain aliphatic moiety having from 1 to 24 carbon atoms in the chain), bearing ary or heterocyclic groups.

30. The method of claim 3, wherein administering the therapeutic compound to the subject modulates cellular free radical damage.

31. The method of claim 22, wherein the therapeutic compound is administered orally, intravenously, buccally, transdermally or subcutaneously.

32. The method of claim 22, further comprising administering the therapeutic compound in a pharmaceutically acceptable vehicle.

33. The method of claim 3, wherein administering the therapeutic compound to the subject modulates an activity of the glutamate neuroreceptor.

34. The method of claim 3, wherein administering the therapeutic compound to the subject modulates an activity of a non-glutamate neuroreceptor.

35. The method of claim 3, wherein administering the therapeutic compound to the subject modulates cerebral guanylyl cyclase activity.

36. The method of claim 3, wherein administering the therapeutic compound to the subject modulates apoptosis.

37. The method of claim 19, wherein administering the therapeutic compound to the subject modulates apoptosis.

38. The method of claim 19, wherein administering the therapeutic compound to the subject modulates cellular free radical damage.

39. The method of claim 19, wherein administering the therapeutic compound to the subject modulates cerebral guanylyl cyclase activity.

40. The method of claim 22, wherein administering the therapeutic compound to the subject modulates levels of the cyclic nucleotides cGMP and/or cAMP.

41. The method of claim 1, wherein said cerebral damage is due to myocardial infarction or a surgical procedure.

42. The method of claim 3, wherein said cerebral damage is due to myocardial infarction or a surgical procedure.

43. The method of claim 27, further comprising administering the therapeutic compound in a pharmaceutically acceptable vehicle.

44. The method of claim 28, further comprising administering the therapeutic compound in a pharmaceutically acceptable vehicle.

* * * * *

UNITED STATES PATENT AND TRADEMARK OFFICE
CERTIFICATE OF CORRECTION

PATENT NO. : 6,310,052 B1
DATED : October 30, 2001
INVENTOR(S) : Gregory R.J. Thatcher, Brian M. Bennett, James N. Reynolds, Roland J. Boegman and Khem Jhamandas It is certified that error appears in the above-identified patent and that said Letters Patent is hereby corrected as shown below:

Column 2,
Line 30, "if" should be -- of --.

Column 4,
Line 33, "$R^1$-$R^4$ cyclic" should be -- $R^1$-$R^4$ in cyclic --.
Line 63, "$P(O)(OR^{16})$" should be -- $P(O)(OR^{14})$ --.

Column 6,
Line 29, "$OHO_2$" should be -- $ONO_2$ --.
Lines 31 to 35, "$R_1$ and $R_3$ are the same or different and selected from H, $C_1$-$C_4$ alkyl and chains, which may rings optionally bear hydroxyl substituents; and
    M is H, $Na^+$, K include one O, linking $R_1$ and $R_3$ to form pentosyl, hexosyl, cyclopentyl or cycohexyl rings, which $^+$," should be
-- $R_1$ and $R_3$ are the same or different and selected from H, $C_1$-$C_4$ alkyl chains, which may include one O, linking $R_1$ and $R_3$ to form pentosyl, hexosyl, cyclopentyl or cyclohexyl rings, which rings optionally bear hydroxyl substituents; and
    M is H, $Na^+$, $K^+$, --.
Line 36, "$N^+H_\Delta R_{17(4-n)}$" should be -- $N^+H_n R_{11(4-n)}$ --.

Column 7,
Line 60, "the ± standard" should be -- the mean ± standard --.

Column 8,
Line 57, "(N=3-8)" should be -- (n=3-8) --.
Line 62, "Ivd" should be -- IVd --.
Line 65, "(N=3-6)" should be -- (n=3-6) --.

Column 10,
Line 19, "aurvival" should be -- survival --.

Column 16,
Formula IIIg, "N⊖" should be -- N⊕ --.

Column 17,
Line 63, "$S(O)_2 R_3$" should be -- $S(O)_2 R_9$ --.

UNITED STATES PATENT AND TRADEMARK OFFICE
CERTIFICATE OF CORRECTION

PATENT NO.   : 6,310,052 B1
DATED        : October 30, 2001
INVENTOR(S)  : Gregory R.J. Thatcher, Brian M. Bennett, James N. Reynolds, Roland J. Boegman and Khem Jhamandas It is certified that error appears in the above-identified patent and that said Letters Patent is hereby corrected as shown below:

Column 24,
Line 2, "IVl" should be -- IV1 --.

Column 31,
Line 4, "t-butylnitrosonthiol" should be -- t-butylnitrosothiol --.

Column 33,
Line 5, "Ivi" should be -- IVi --.
Line 14, "IVn" should be -- IVi --.
Line 20, "IVn" should be -- IVm --.
Line 38, "in 5 of cold" should be -- in 5 g of cold --.

Column 34,
Line 44, "R. R. Riscus" should be -- R. R. Fiscus --.

Column 35,
Line 5, "Neurosic." should be -- Neurosci. --.
Line 35, "23-25" should be -- 2325 --.
Line 35, "2234" should be -- 2334 --.

Column 37,
Formula II, should be

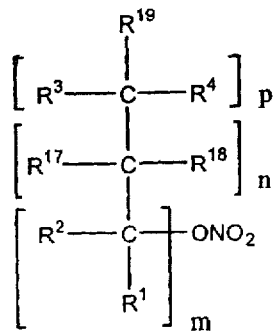

Column 38,
Line 41, "$SR^6$" should be -- $SR^5$ --.
Line 56, "Na'" should be -- $Na^+$ --.

UNITED STATES PATENT AND TRADEMARK OFFICE
CERTIFICATE OF CORRECTION

PATENT NO. : 6,310,052 B1
DATED : October 30, 2001
INVENTOR(S) : Gregory R.J. Thatcher, Brian M. Bennett, James N. Reynolds, Roland J. Boegman and Khem Jhamandas It is certified that error appears in the above-identified patent and that said Letters Patent is hereby corrected as shown below:

Column 39,
Line 27, "SC(O)NHR$^{16}$" should be -- SC(O)NHR$^{15}$ --.
Line 29, "P(O)(OM)R$^{16}$" should be -- P(O)(OM)R$^{15}$ --.
Line 39, "P(O)(OM)R$^{16}$" should be -- P(O)(OM)R$^{15}$ --.
Line 41, "SSR$^{6}$" should be -- SSR$^{5}$ --.

Column 40,
Line 1, "claim 7" should be -- claim 4 --.
Line 4, "is" should be -- in --.
Line 5, "claim 7" should be -- claim 4 --.
Line 53, "NR$^{8}$" should be -- NR$^{6}$ --.

Column 41,
Line 43, "ary" should be -- aryl --.

Signed and Sealed this

Thirtieth Day of April, 2002

Attest:

*Attesting Officer*

JAMES E. ROGAN
*Director of the United States Patent and Trademark Office*